(12) United States Patent
Matsushima et al.

(10) Patent No.: US 8,524,727 B2
(45) Date of Patent: Sep. 3, 2013

(54) PYRIMIDINE COMPOUND

(75) Inventors: Yuji Matsushima, Toyko (JP); Hirokazu Kubota, Tokyo (JP); Hisao Hamaguchi, Tokyo (JP); Yoshinori Okamoto, Tokyo (JP); Takeshi Hondo, Tokyo (JP); Fusako Nishigaki, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 116 days.

(21) Appl. No.: 12/933,137

(22) PCT Filed: Mar. 29, 2010

(86) PCT No.: PCT/JP2010/055506
§ 371 (c)(1),
(2), (4) Date: Sep. 17, 2010

(87) PCT Pub. No.: WO2010/113834
PCT Pub. Date: Oct. 7, 2010

(65) Prior Publication Data
US 2011/0053912 A1 Mar. 3, 2011

(30) Foreign Application Priority Data

Mar. 30, 2009 (JP) .................................. 2009-082282

(51) Int. Cl.
*A01N 43/54* (2006.01)
*A61K 31/505* (2006.01)

(52) U.S. Cl.
USPC ......................................... 514/275; 544/330

(58) Field of Classification Search
USPC .................... 544/297, 315, 316, 318
See application file for complete search history.

(56) References Cited

U.S. PATENT DOCUMENTS

| | | | |
|---|---|---|---|
| 4,539,324 A * | 9/1985 | Benneche et al. ............ | 514/274 |
| 5,811,428 A | 9/1998 | Suto et al. | |
| 5,935,966 A * | 8/1999 | Suto et al. ..................... | 514/275 |
| 6,806,230 B1 * | 10/2004 | Yasuda et al. .................. | 504/239 |
| 2005/0245554 A1 | 11/2005 | Kopka et al. | |
| 2006/0247261 A1 | 11/2006 | Eatherton et al. | |
| 2006/0293354 A1 | 12/2006 | Eatherton | |
| 2008/0261977 A1 | 10/2008 | Eatherton et al. | |
| 2012/0053164 A1 * | 3/2012 | Ebel et al. ................. | 514/210.18 |

FOREIGN PATENT DOCUMENTS

| | | |
|---|---|---|
| EP | 569912 A1 * | 11/1993 |
| JP | 2006 501228 | 1/2006 |
| JP | 2006 510597 | 3/2006 |
| JP | 2007 523207 | 8/2007 |
| WO | 96 25397 | 8/1996 |
| WO | 97 09315 | 3/1997 |
| WO | 97 09325 | 3/1997 |
| WO | 98 38171 | 9/1998 |
| WO | 01 19788 | 3/2001 |
| WO | 2004 018433 | 3/2004 |
| WO | 2004 018434 | 3/2004 |
| WO | 2004 029026 | 4/2004 |
| WO | 2004 029027 | 4/2004 |
| WO | 2004 085385 | 10/2004 |
| WO | 2005 075440 | 8/2005 |
| WO | 2005 075464 | 8/2005 |
| WO | 2005 080342 | 9/2005 |
| WO | 2005 080349 | 9/2005 |
| WO | 2005 080350 | 9/2005 |
| WO | 2005 121140 | 12/2005 |
| WO | 2006 043260 | 4/2006 |
| WO | 2006 050476 | 5/2006 |
| WO | 2007 017237 | 2/2007 |
| WO | 2007 017264 | 2/2007 |
| WO | 2007 088168 | 8/2007 |
| WO | 2007 118859 | 10/2007 |
| WO | 2008 027812 | 3/2008 |
| WO | 2008 116816 | 10/2008 |
| WO | 2009 137081 | 11/2009 |

OTHER PUBLICATIONS

A. Porcheddu et al., 6 Journal of Combinatorial Chemistry, 105-111 (2004).*
R. Urban et al., 41 Helvetica Chimica Acta 1806-1816 (1958).*
Extended Search Report issued Jul. 17, 2012 in European Application No. EP 10 75 8605.9.
International Search Report issued May 25, 2010 in PCT/JP10/55506 filed Mar. 29, 2010.
Sullivan, W. Robert et al., "2-Chloro-4-(trifluoromethyl)pyrimidine-5-N-(3',5'-bis(trifluoromethethyl)phenyl)-carboxamide: A Potent Inhibitor of NF-κB- and AP-1-Mediated Gene Expression Identified Using Solution-Phase Combinatorial Chemistry", Journal of Medicinal Chemistry, vol. 41, No. 4, pp. 413-419, (1998).
Porcheddu, Andrea et al., "A "Catch and Release" Strategy for the Parallel Synthesis of 2,4,5-Trisubstituted Pyrimidines", Journal of Combinatorial Chemistry, vol. 6, No. 1, pp. 105-111, (2004).
Gayo, M. Leah et al., "Traceless Linker: Oxidative Activation and Displacement of a Sulfur-Based Linker", Tetrahedron Letters, vol. 38, No. 2, pp. 211-214, (1997).

* cited by examiner

*Primary Examiner* — James O Wilson
*Assistant Examiner* — Alexander R Pagano
(74) *Attorney, Agent, or Firm* — Oblon, Spivak, McClelland, Maier & Neustadt, L.L.P.

(57) ABSTRACT

A novel and excellent method for preventing and/or treating diseases related to a cannabinoid type 2 receptor, based on an agonistic action on a cannabinoid type 2 receptor. It was found that a hetero ring derivative mainly having two substituents, for example, a pyrimidine-5-carboxamide derivative having a substituent amino group at the 2-position, exhibits a potent agonistic action on a cannabinoid type 2 receptor, and can be an agent for preventing and/or treating diseases related to a cannabinoid type 2 receptor such as inflammatory diseases, pain, and the like.

16 Claims, No Drawings

PYRIMIDINE COMPOUND

CROSS REFERENCES TO RELATED APPLICATIONS

This application is a 371 of International Patent Application No. PCT/JP2010/055506, filed on Mar. 29, 2010, and claims priority to Japanese Patent Application No. 2009-082282, filed on Mar. 30, 2009.

TECHNICAL FIELD

The present invention relates to a pyrimidine compound which is useful as an active ingredient of a pharmaceutical composition, in particular, a pharmaceutical composition for preventing and/or treating a disease related to a cannabinoid type 2 receptor.

BACKGROUND ART

A cannabinoid is a generic name referring to marijuana components contained in *Cannabis sativa*, about 60 kinds or more thereof are known so far, and typical examples thereof include tetrahydrocannabinol, cannabinol, cannabidiol, and the like. Marijuana has been used in pharmaceuticals or the like for thousands of years, and it shows a neuropsychiatric response and causes sensory confusion, euphoria, analgesic action, hallucination, or the like. Cannabinoids have a great variety of pharmacological actions, and have been found to have an immunosuppressive action, an anti-inflammatory action, an analgesic action, or the like, in addition to the actions in the central nervous system.

A cannabinoid receptor is a 7-transmembrane G protein-coupled receptor, and two types thereof, a cannabinoid type 1 receptor (CB1) and a cannabinoid type 2 receptor (CB2), have been hitherto identified and screened (Nature, 1990, 346, 561-564; and Nature, 1993, 365, 61-65). Human CB1 consists of 472 amino acids, and is significantly expressed in the globus pallidus, striatum, substantia nigra, hippocampus, stratum moleculare of cerebellum, cerebral cortex, or the like in the brain. Besides the expression in the brain, it is also expressed in the testis, vas deferens, uterus, small intestine, blood vessels, or the like. CB2 consists of 360 amino acids, has a homology of 44% to CB1, and is significantly expressed in the spleen, tonsils, and lymph nodes, and also in leukocyte cells such as macrophages, monocytes, B lymphocytes, NK cells, eosinophils, and the like. Recently, CB2 has also been reported to be expressed in the brain (Science, 2005, 310, 329-332).

A CB2 agonist has been reported to exhibit a central analgesic action (European Journal of Neuroscience, 2006, 23, 1530-1538) and a peripheral analgesic action (Proceedings of the National Academy of Sciences, 2005, 102, 3093-3098). Also, a CB2 agonist has been reported to exhibit an immunosuppressive action and an anti-inflammatory action since CB2 is significantly expressed in the hematopoietic cells and immune cells (British Journal of Pharmacology, 2003, 139, 775-786). It has been reported that a CB2 agonist has an anti-pruritic action in skin diseases (Science, 2007, 316, 1494-1497), and is expected to be applied to atopic dermatitis or the like. In addition, a CB2 agonist can be expected to be effective in atherosclerosis (Nature, 2005, 434, 782-786), reflux esophagitis (European Journal of Pharmacology, 2007, 573, 206-213), liver disorders (British Journal of Pharmacology, 2008, 153, 286-289), and chronic liver diseases (Expert Opinion of Therapeutic Targets, 2007, 11, 403-409), due to its anti-inflammatory action and immunosuppressive action. Furthermore, CB2 is also expressed in osteoblasts and osteoclasts, and a CB2 agonist has been reported to have an action of inhibiting bone destruction through an action of increasing the osteoblasts and an action of inhibiting the activity of the osteoclasts (Proceedings of the National Academy of Sciences, 2006, 103, 696-701).

As CB2 agonistic compounds, a pyridine derivative (Patent Documents 1 to 4), an indole derivative (Patent Document 5), a pyrrolopyridine derivative (Patent Document 6), an α-pinene derivative (Patent Document 7), an imidazopyridine derivative (Patent Document 8), a pyrrolopyridine derivative (Patent Document 9), a pyrrolopyrazine derivative (Patent Document 10), an imidazopyrimidine derivative (Patent Document 11), and the like have been reported. In addition, as a pyrimidine derivative, the following compounds have been reported. Patent Documents 12 to 15 show that a compound of the formula (A) has a CB2 agonistic activity and Patent Document 16 shows that a compound of the formula (B) has a CB2 agonistic activity. However, there is no disclosure of the compounds described in the present application.

(In the formula, Y represents phenyl which may have a substituent. For the other symbols, refer to the publications.)

[Chem. 1]

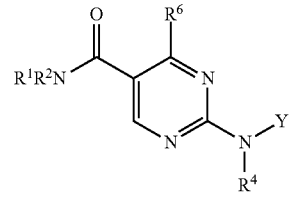

(A)

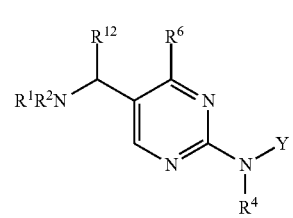

(B)

Further, the following pyrimidine compound has been known.

Patent Documents 17 and 18, and Non-Patent Document 1 show that a compound of the formula (C) is useful in inflammation. However, these documents have neither disclosure of a CB2-related activity nor disclosure of the compound described in the present application.

(For the symbols in the formula, refer to the publications.)

[Chem. 2]

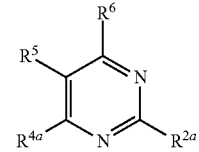

(C)

Patent Document 19 shows that a compound of the formula (D) is useful for pain. However, this document has neither disclosure of a CB2-related activity nor disclosure of the compound described in the present application.

(For the symbols in the formula, refer to the publication.)

[Chem. 3]

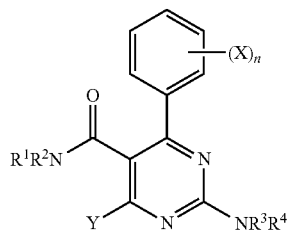
(D)

Patent Documents 20 to 22 describe that a compound of the formula (E), characterized in that the substituent $R^2$ is hydrazine, is useful for inflammation. However, these documents have neither disclosure of a CB2-related activity nor disclosure of the compound described in the present application.

(For the symbols in the formula, refer to the publications.)

[Chem. 4]

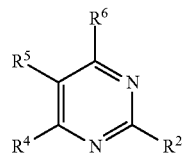
(E)

Patent Document 23 describes that a compound of the formula (F) can be a ligand selective to a dopamine D3 receptor. However, this document has neither disclosure of a CB2-related activity nor disclosure of the compound described in the present application.

(For the symbols in the formula, refer to the publication.)

[Chem. 5]

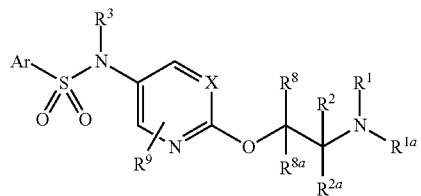
(F)

A compound of the formula (G) is commercially available from Aurora Fine Chemicals Ltd., and the like.

[Chem. 6]

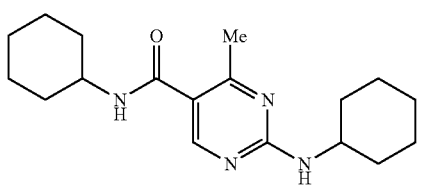
(G)

A compound of the formula (H) is a known compound (Registry Number: 1026643-33-3).

[Chem. 7]

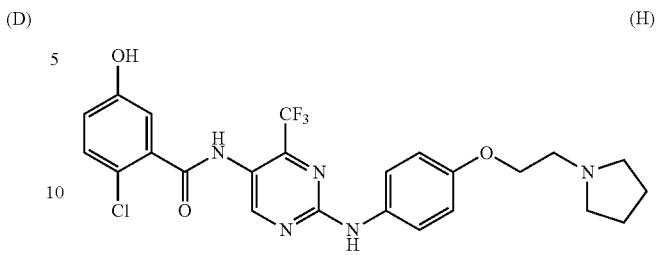
(H)

In documents relating to synthetic organic chemistry, pyrimidine derivatives are disclosed (Non-Patent Document 2 and Non-Patent Document 3).

RELATED ART DOCUMENTS

Patent Documents
Patent Document 1: Pamphlet of International Publication No. 2004/029026
Patent Document 2: Pamphlet of International Publication No. 2004/029027
Patent Document 3: Pamphlet of International Publication No. 2005/075464
Patent Document 4: Pamphlet of International Publication No. 2005/080342
Patent Document 5: Pamphlet of International Publication No. 96/025397
Patent Document 6: Pamphlet of International Publication No. 2005/121140
Patent Document 7: Pamphlet of International Publication No. 2006/043260
Patent Document 8: Pamphlet of International Publication No. 2007/017237
Patent Document 9: Pamphlet of International Publication No. 2007/017264
Patent Document 10: Pamphlet of International Publication No. 2007/088168
Patent Document 11: Pamphlet of International Publication No. 2008/027812
Patent Document 12: Pamphlet of International Publication No. 2004/018433
Patent Document 13: Pamphlet of International Publication No. 2004/018434
Patent Document 14: Pamphlet of International Publication No. 2005/075440
Patent Document 15: Pamphlet of International Publication No. 2005/080349
Patent Document 16: Pamphlet of International Publication No. 2005/080350
Patent Document 17: Pamphlet of International Publication No. 97/09315
Patent Document 18: Specification of U.S. Pat. No. 5,811,428
Patent Document 19: Pamphlet of International Publication No. 2006/050476
Patent Document 20: Pamphlet of International Publication No. 97/09325
Patent Document 21: Pamphlet of International Publication No. 98/38171
Patent Document 22: Specification of U.S. Pat. No. 5,935,966
Patent Document 23: Pamphlet of International Publication No. 2007/118859

Non-Patent Documents
Non-Patent Document 1: Journal of Medicinal Chemistry, 1998, 41, 413-419
Non-Patent Document 2: Journal of Combinatorial Chemistry, 2004, 6, 105-111
Non-Patent Document 3: Tetrahedron Letters, 1997, 38, 211-214

DISCLOSURE OF THE INVENTION

Problem that the Invention is to Solve

It is an object of the present invention to provide a compound which is useful as a pharmaceutical composition, for example, a pharmaceutical having a CB2 agonistic action, and in particular, an agent for preventing and/or treating diseases related to CB2.

Means for Solving the Problem

The present inventors have conducted extensive studies on CB2 agonists, and as a result, and found that a pyrimidine compound shown below has an excellent CB2 agonistic action, and thus can be an agent for preventing and/or an agent for treating diseases related to CB2, thereby completed the present invention.

That is, the present invention relates to a compound of the formula (I) or a salt thereof, and a pharmaceutical composition comprising the compound of the formula (I) or a salt thereof, and an excipient.

[Chem. 8]

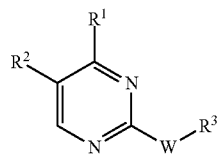

(I)

[wherein
$R^1$: lower alkyl, $C_{3-6}$ cycloalkyl, —O-lower alkyl, halogeno-lower alkyl, -lower alkylene-$C_{3-6}$ cycloalkyl, or -lower alkylene-O-lower alkyl;
$R^2$: —C(O)$R^{20}$, —C(O)N$R^{21}R^{22}$, -lower alkylene-$R^{20}$, -lower alkylene-N$R^{21}R^{22}$, -lower alkylene-N$R^0$C(O)$R^{21}$, -lower alkylene-O$R^{21}$, —N$R^0$C(O)$R^{21}$; —N$R^0$C(O)O$R^{21}$, —N$R^0$C(O)N$R^{21}R^{22}$, —N$R^0$S(O)$_2R^{21}$, or —N$R^0$S(O)$_2$N$R^{21}R^{22}$;
W: —CH$_2$—, —N$R^0$—, —O—, or —S(O)$_m$—;
$R^3$: $C_{3-10}$ alkyl; $C_{2-6}$ alkenyl; $C_{2-6}$ alkynyl; halogeno-$C_{3-6}$ alkyl; $C_{1-10}$ alkyl substituted with 1 to 5 groups selected from Group G$^1$; $R^{30}$; —C$_{1-10}$ alkylene-$R^{30}$; alkylene-O—$R^{30}$; —C$_{1-10}$ alkylene-O-lower alkylene-$R^{30}$; —C$_{1-10}$ alkylene-S(O)$_2$—$R^{30}$; —X—C($R^0$)(phenyl)$_2$; or —CH(phenyl)-CH(OH)-phenyl;
wherein the $C_{1-10}$ alkylene may have 1 to 5 substituents selected from Group G$^1$;
or W and $R^3$ are, combined to each other,

[Chem. 9]

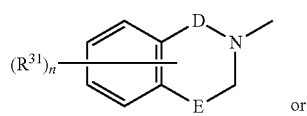

or

[Chem. 10]

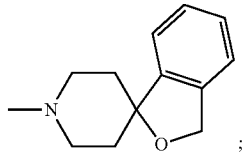

;

$R^0$: the same as or different from each other, each representing H or lower alkyl;
$R^{20}$: a nitrogen-containing saturated hetero ring group which may have 1 to 5 substituents selected from Group G$^2$;
$R^{21}$: lower alkyl, halogeno-lower alkyl, -lower alkylene-O$R^0$, -lower alkylene-O-lower alkylene-O$R^0$, -lower alkylene-O-halogeno-lower alkyl, or, —X—$C_{3-10}$-cycloalkyl, -lower alkylene-O—$C_{3-10}$ cycloalkyl, —X—$C_{3-10}$ cycloalkenyl, -lower alkylene-O—$C_{3-10}$ cycloalkenyl, —X-aryl, -lower alkylene-O—X-aryl, -lower alkylene-S(O)$_m$-aryl, —X-hetero ring group, -lower alkylene-O—X-hetero ring group, or -lower alkylene-S(O)$_m$-hetero ring group, each of which may have 1 to 5 substituents selected from Group G$^3$ on the ring;
$R^{22}$: H, lower alkyl, or -lower alkylene-O$R^0$;
$R^{30}$: $C_{3-10}$ cycloalkyl, $C_{5-10}$ cycloalkenyl, aryl, or a hetero ring group;
wherein $R^{30}$ may have 1 to 5 substituents selected from Group G$^3$;
$R^{31}$: the same as or different from each other, each representing lower alkyl, halogen, —O-lower alkyl, halogeno-lower alkyl, —C(O)O$R^0$, or nitro;
Group G$^1$: halogen, —C(O)O$R^0$, —C(O)N($R^0$)$_2$, —CN, —O$R^0$, —O-lower alkylene-O$R^0$, —O-halogeno-lower alkyl, —N($R^0$)$_2$, —N($R^0$)-phenyl, —N(lower alkylene-O$R^0$)$_2$, —NHC(O)-lower alkyl, —N($R^0$)C(O)N($R^0$)$_2$, —S(O)$_m$-lower alkyl, and —S(O)$_2$N($R^0$)$_2$;
Group G$^2$: lower alkyl, halogen, halogeno-lower alkyl, —C(O)O$R^0$, —C(O)N($R^0$)$_2$, —CN, —X—O$R^0$, —O-lower alkylene-O$R^0$, —O-halogeno-lower alkyl, —OC(O)-lower alkyl, —X—N($R^0$)$_2$, oxo, —X—$C_{3-6}$ cycloalkyl, —X—O—X—$C_{3-6}$ cycloalkyl, —X-phenyl, and —X-morpholinyl;
Group G$^3$: lower alkyl, $C_{2-6}$ alkenyl, $C_{2-6}$ alkynyl, halogen, halogeno-lower alkyl, —X—C(O)O$R^0$, —X—C(O)N($R^0$)$_2$, —CN, —X—C(O)$R^0$, —X—O$R^0$, —O-lower alkylene-O—$R^0$, —O-halogeno-lower alkyl, —OC(O)-lower alkyl, —X—N($R^0$)$_2$, —X—S(O)$_m$-lower alkyl, oxo, —X—$C_{3-10}$ cycloalkyl, —X—O—X—$C_{3-10}$ cycloalkyl, —X-aryl, —X—C(O)-aryl, —X—O—X-aryl, —X—S(O)$_m$-aryl, —X-hetero ring group, —X—O—X-hetero ring group, —X—S(O)$_m$-hetero ring group, and —O—CH$_2$CH$_2$—O— binding to the same carbon;
wherein the aryl and the hetero ring group may be substituted with lower alkyl, halogen, halogeno-lower alkyl, —O-lower alkyl, or oxo;
D: a bond or —C($R^{31}$)$_2$—;
E: a bond, —[C($R^{31}$)$_2$]$_{1-3}$—, or —O—C($R^{31}$)$_2$—;
wherein O binds to the benzene ring;
X: the same as or different from each other, each representing a bond or lower alkylene;
m: the same as or different from each other, each representing 0, 1, or 2;
n: the same as or different from each other, each representing 0, 1, or 2;
provided that
(1) in case $R^2$ is —C(O)$R^{20}$, $R^1$ is a group other than methyl and —W—$R^3$ is a group other than —NH-phenyl which may be substituted;

(2) in case $R^2$ is —C(O)NR$^{21}$R$^{22}$, $R^3$ is $C_{5-10}$ cycloalkyl or -lower alkylene-$C_{5-10}$ cycloalkyl, and the $C_{5-10}$ cycloalkyl may have 1 to 5 substituents selected from Group G$^3$;

(3) in case $R^2$ is -lower alkylene-$R^{20}$ or -lower alkylene-NR$^{21}$R$^{22}$ and W is —CH$_2$—, —NR$^0$—, —O—, or —S(O)$_m$—, $R^3$ is $C_{7-10}$ cycloalkyl or -lower alkylene-$C_{7-10}$ cycloalkyl and the $C_{7-10}$ cycloalkyl may have 1 to 5 substituents selected from Group G$^3$;

(4) in case $R^2$ is -lower alkylene-NR$^0$C(O)R$^{21}$, $R^1$ is a group other than methyl;

(5) in case $R^2$ is —NR$^0$C(O)R$^{21}$, —NR$^0$C(O)OR$^{21}$, —NR$^0$C(O)NR$^{21}$R$^{22}$, —NR$^0$S(O)$_2$R$^{21}$, or —NR$^0$S(O)$_2$NR$^{21}$R$^{22}$, $R^1$ is a group other than methyl and —W—$R^3$ is a group other than —CH$_2$-1H-pyrazol-1-yl which may be substituted, and —CH$_2$-1H-1,2,4-triazol-1-yl which may be substituted; and the following compounds are excluded;

2-(cyclohexylamino)-N-(3,5-dichlorophenyl)-4-(trifluoromethyl)pyrimidine-5-carboxamide, 2-(cyclohexylamino)-N,N-diethyl-4-isopropylpyrimidine-5-carboxamide, N-cyclohexyl-2-(cyclohexylamino)-4-methylpyrimidine-5-carboxamide, tert-butyl({2-[(3-chloro-4-fluorophenyl)amino]-4-(trifluoromethyl)-5-pyrimidinyl}methyl)(cyclopropylmethyl) carbamate, 1-{[5-(methoxymethyl)-4-(trifluoromethyl)-2-pyrimidinyl]amino}-3-methyl-1H-pyrrole-2,5-dione, 1-{[4-ethyl-5-(methoxymethyl)-2-pyrimidinyl](methyl)amino}-3-methyl-1H-pyrrole-2,5-dione, N-butyl-5-(phenoxymethyl)-4-(trifluoromethyl)pyrimidin-2-amine, 2-chloro-5-hydroxy-N-[2-[[4-[2-(1-pyrrolidinyl)ethoxy]phenyl]amino]-4-(trifluoromethyl)-5-pyrimidinyl]benzamide, N-{4-methoxy-2-[2-(propylamino)ethoxy]-5-pyrimidinyl}-4-(trifluoromethoxy)benzenesulfonamide, and N-{4-methoxy-2-[2-(propylamino)ethoxy]-5-pyrimidinyl}-4-isopropylbenzenesulfonamide].

In the present specification, the symbols defined above are used to represent the same meanings, unless otherwise specifically defined.

Further, the present invention relates to a pharmaceutical composition for preventing and/or treating a disease related to CB2, comprising the compound of the formula (I) or a salt thereof, that is, an agent for preventing and/or an agent for treating a disease related to CB2, comprising the compound of the formula (I) or a salt thereof.

Further, the present invention relates to use of the compound of the formula (I) or a salt thereof for the manufacture of a pharmaceutical composition for preventing and/or treating a disease related to CB2, use of the compound of the formula (I) or a salt thereof for preventing and/or treating a disease related to CB2, and a method for preventing and/or treating a disease related to CB2, comprising administering to a patient an effective amount of the compound of the formula (I) or a salt thereof.

Effect of the Invention

The compound of the formula (I) has a CB2 agonistic action, and can be used as an agent for preventing and/or treating diseases related to CB2.

Examples of the diseases related to CB2 include inflammatory diseases (for example, rheumatoid arthritis, osteoarthritis, and the like), pain (for example, acute pain, chronic pain, nociceptive pain, inflammatory pain, rheumatoid arthritis pain, osteoarthritis pain, and the like), cancers and tumors (for example, cancers of the immune system, lung cancer, colon cancer, leukemia, and the like), respiratory diseases (for example, respiratory distress syndrome, phthisis, asthma, chronic obstructive lung diseases, and the like), liver diseases, brain diseases, eye diseases (for example, ocular hypertension, cataracts, glaucoma, retinal diseases, and the like), skin diseases (for example, itching dermatitis, fungal diseases on the skin surface, and the like), cardiovascular diseases (for example, angina, myocardial infarction, arteriosclerosis, hypertension, restenosis after coronary stent, thrombosis, and the like), allergic conditions (for example, anaphylaxis, allergic asthma, atopic asthma, drug allergy, and the like), gastrointestinal diseases (for example, constipation, diarrhea, vomiting, peptic ulcer, irritable bowel syndrome, ulcerative colitis, and the like), immune diseases (for example, immune deficiency, psoriasis, rheumatoid arthritis, osteoporosis, sepsis, systemic lupus erythematosus, and the like), neurological conditions (for example, neurodegenerative diseases, nausea, neuropathy, dementia, Parkinson's disease, schizophrenia, obsessive-compulsive disorder, post-traumatic stress disorder, memory disorders, anorexia, cibophobia, circadian rhythm disorders, sleep apnea, drug addiction, movement disorders, convolsion, paresthesia, and the like), bone formation, bone reconstruction, obesity, and the like.

BEST MODE FOR CARRYING OUT THE INVENTION

Hereinafter, the present invention is described in detail.

In the definitions in the present specification, "alkyl", "alkylene", "alkenyl", and "alkynyl" mean linear or branched hydrocarbon chains, unless otherwise specifically defined.

The "lower alkyl" refers to linear or branched alkyl having 1 to 6 carbon atoms (hereinafter referred to as $C_{1-6}$), for example, methyl, ethyl, n-propyl, isopropyl, n-butyl, isobutyl, sec-butyl, tert-butyl, n-pentyl, n-hexyl, and the like. In another embodiment, it is $C_{1-4}$ alkyl, and in a further embodiment, it is methyl, ethyl, n-propyl, isopropyl, or tert-butyl.

The "lower alkylene" refers to linear or branched $C_{1-6}$ alkylene, for example, methylene, ethylene, trimethylene, tetramethylene, pentamethylene, hexamethylene, propylene, methylmethylene, ethylethylene, 1,2-dimethylethylene, or 1,1,2,2-tetramethylethylene. In another embodiment, it is $C_{1-5}$ alkylene, and in a further embodiment, it is methylene, ethylene, trimethylene, tetramethylene, or pentamethylene.

The "lower alkenyl" refers to linear or branched $C_{2-6}$ alkenyl, for example, vinyl, propenyl, butenyl, pentenyl, 1-methylvinyl, 1-methyl-2-propenyl, 1,3-butadienyl, 1,3-pentadienyl, or the like. In another embodiment, it is $C_{2-4}$ alkenyl.

The "lower alkynyl" refers to linear or branched $C_{2-6}$ alkynyl, for example, ethynyl, propynyl, butynyl, pentynyl, 1-methyl-2-propynyl, 1,3-butadynyl, 1,3-pentadynyl, or the like. In another embodiment, it is $C_{2-4}$ alkynyl.

The "halogen" means F, Cl, Br, or I.

The "halogeno-lower alkyl" refers to lower alkyl substituted with at least one halogen. In another embodiment, it is lower alkyl substituted with one to seven halogen atoms, and in a further embodiment it is trifluoromethyl.

The "cycloalkyl" refers to a $C_{3-10}$ saturated hydrocarbon ring group, which may have a bridge. It is, for example, cyclopropyl, cyclobutyl, cyclopentyl, cyclohexyl, cycloheptyl, cyclooctyl, cyclononyl, cyclodecyl, bicyclo[2.2.1]heptyl, bicyclo[3.1.1]heptyl, bicyclo[2.2.2]octyl, adamantyl, hexahydromethanopentalenyl, or the like. In another embodiment, it is $C_{5-10}$ cycloalkyl, in a further embodiment, it is $C_{7-10}$ cycloalkyl, in a still further embodiment, it is cycloheptyl, cyclooctyl, cyclononyl, cyclodecyl, bicyclo[2.2.1]heptyl, bicyclo[3.1.1]heptyl, bicyclo[2.2.2]octyl, adamantyl, or hexahydromethanopentalenyl, and in a still further embodiment, it is bicyclo[2.2.1]heptyl, bicyclo[3.1.1]heptyl, bicyclo[2.2.2]octyl, or adamantyl.

The "cycloalkenyl" refers to $C_{4-15}$ cycloalkenyl, which may have a bridge. It is, for example, cyclopentenyl, cyclopentadienyl, cyclohexenyl, cyclohexadienyl, bicyclo[2.2.1]heptenyl group, or the like. In another embodiment, it is $C_{5-10}$ cycloalkenyl, and in a further embodiment, it is cyclopentenyl, cyclohexenyl, or bicyclo[2.2.1]heptenyl.

The "aryl" refers to a $C_{6-14}$ monocyclic to tricyclic aromatic hydrocarbon ring group, and includes ring groups which are condensed with $C_{5-8}$ cycloalkene at the double bond site. It is, for example, phenyl, naphthyl, tetrahydronaphthalenyl, indanyl, indenyl, fluorenyl, or the like. In another embodiment, it is phenyl or naphthyl, and in a further embodiment, it is phenyl.

The "hetero ring" group means a ring group selected from i) a 3- to 8-membered, in another embodiment, 5- to 7-membered, monocyclic hetero ring containing 1 to 4 hetero atoms selected from oxygen, sulfur, and nitrogen, and ii) a bi- to tricyclic hetero ring containing 1 to 5 hetero atoms selected from oxygen, sulfur, and nitrogen, formed by condensation of the monocyclic hetero ring with 1 or 2 rings selected from a monocyclic hetero ring, benzene ring, $C_{5-4}$ cycloalkane, and $C_{5-8}$ cycloalkene. It may form a Spiro ring. The ring atom, sulfur or nitrogen, may be oxidized to form an oxide or dioxide.

As the "hetero ring", the following embodiments may be mentioned:

(1) Monocyclic saturated hetero ring (a) those containing 1 to 4 nitrogen atoms, for example, aziridinyl, azetidinyl, pyrrolidinyl, pyrazolidinyl, imidazolidinyl, piperidyl, piperazinyl, azepanyl, diazepanyl, azocanyl, azonanyl, and the like;

(b) those containing 1 to 3 nitrogen atoms and 1 to 2 oxygen atoms and/or 1 to 2 sulfur atoms, for example, oxazolidinyl, isooxazolidinyl, thiazolidinyl, isothiazolidinyl, morpholinyl, thiomorpholinyl, homomorpholinyl, thiazepanyl, and the like;

(c) those containing 1 to 2 oxygen atoms, for example oxiranyl, oxetanyl, tetrahydrofuranyl, tetrahydropyranyl, dioxoranyl, 1,4-dioxanyl, and the like;

(d) those containing 1 to 2 sulfur atoms, for example, tetrahydrothiofuranyl, tetrahydrothiopyranyl, and the like; and (e) those containing 1 to 2 oxygen atoms and 1 to 2 sulfur atoms, for example, oxathiolanyl, and the like;

(2) Monocyclic unsaturated hetero ring group (a) those containing 1 to 4 nitrogen atoms, for example, pyrrolyl, pyrrolinyl, pyrazolyl, pyrazolinyl, imidazolyl, imidazolinyl, triazolyl, tetrazolyl, pyridyl, dihydropyridinyl, tetrahydropyridinyl, pyridazinyl, pyrimidinyl, dihydropyrimidinyl, pyrazinyl, triazinyl, dihydrotriazinyl, azepinyl, and the like;

(b) those containing 1 to 3 nitrogen atoms and 1 to 2 oxygen atoms and/or 1 to 2 sulfur atoms, for example, oxazolyl, isooxazolyl, thiazolyl, isothiazolyl, oxadiazolyl, thiadiazolyl, dihydrothiazinyl, oxadinyl, and the like;

(c) those containing 1 to 2 oxygen atoms, for example, furyl, dioxolyl, pyranyl, oxepinyl, and the like;

(d) those containing 1 to 2 sulfur atoms, for example, thienyl, dihydrothiophenyl, dihydrodithiopyranyl, dihydrodithionyl, thiepinyl, and the like; and (e) those containing 1 to 2 oxygen atoms and 1 to 2 sulfur atoms, for example, dihydrooxathiopyranyl, and the like;

(3) Condensed polycyclic saturated hetero ring group (a) those containing 1 to 5 nitrogen atoms, for example, quinuclidinyl, 7-azabicyclo[2.2.1]heptyl, azabicyclo[3.2.1]octyl, diazabicyclo[3.2.1]octyl, azabicyclo[3.2.2]nonyl, azabicyclo[3.3.1]nonyl, and the like;

(b) those containing 1 to 4 nitrogen atoms and 1 to 3 oxygen atoms and/or 1 to 3 sulfur atoms, for example, 2-oxa-5-azabicyclo[2.2.1]heptyl, trithiadiazaindenyl, dioxoloimidazolidinyl, and the like; and (c) those containing 1 to 3 oxygen atoms and/or 1 to 3 sulfur atoms, for example, oxabicyclo[2.2.1]heptyl, 2,6-dioxabicyclo[3.2.2]octyl, and the like; and (4) Condensed polycyclic unsaturated hetero ring (a) those containing 1 to 5 nitrogen atoms, for example, dihydropyrrolotriazolyl, indolyl, indolinyl, isoindolyl, isoindolinyl, indolidinyl, indazolyl, dihydroindazolyl, benzimidazolyl, dihydrobenzimidazolyl, tetrahydrobenzimidazolyl, dihydropyrrolopyradinyl, pyrazolopyridinyl, tetrahydropyrazolopyridinyl, imidazopyridinyl, tetrahydroimidazopyridinyl, benzotriazolyl, triazolopyridinyl, purinyl, triazolopyrimidinyl, quinolyl, tetrahydroquinolinyl, isoquinolinyl, tetrahydroisoquinolinyl, quinolidinyl, cinnolinyl, phthaladinyl, quinazolinyl, quinoxalinyl, dihydroquinoxalinyl, tetrahydroquinoxalinyl, naphthylidinyl, benzopyrimidinyl, tetrahydrobenzazepinyl, carbazolyl, acridinyl, tetrazolopyridazinyl, and the like;

(b) those containing 1 to 4 nitrogen atoms and 1 to 3 oxygen atoms and/or 1 to 3 sulfur atoms, for example, imidazothiazolyl, benzoxazolyl, dihydrobenzoxazolyl, benzisooxazolyl, benzoxadiazolyl, benzothiazolyl, dihydrobenzothiazolyl, benzisothiazolyl, benzothiadiazolyl, imidazothiazolyl, imidazothiadiazolyl, dihydrothienopyridinyl, dihydrothiazolopyridinyl, dihydrobenzoxadinyl, 3H-spiro[2-benzofuran-1,4'-piperidin]-1'-yl, and the like;

(c) those containing 1 to 3 oxygen atoms, for example benzofuranyl, dihydrobenzofuranyl, isobenzofuranyl, benzodioxolyl, chromenyl, chromanyl, ethylenedioxyphenyl, xanthenyl, dibenzo[b,d]furanyl, and the like;

(d) those containing 1 to 3 sulfur atoms, for example, dihydrocyclopentathiophenyl, thienothiophenyl, benzothiophenyl, dihydrothiochromenyl, benzodithiopyranyl, dibenzo[b,d]thienyl, and the like; and (e) those containing 1 to 3 oxygen atoms and 1 to 3 sulfur atoms, for example, benzoxathiopyranyl, phenoxazinyl, and the like;

and others.

The "nitrogen-containing hetero ring" means those containing at least one nitrogen atom, as (1)-(a), (1)-(b), (2)-(a), (2)-(b), (3)-(a), (3)-(b), (4)-(a), (4)-(b), and the like, among the above-described "hetero ring".

The "nitrogen-containing saturated hetero ring" means those in which the bonds constituting the ring consist of single bonds, as (1)-(a), (1)-(b), (3)-(a), (3)-(b), and the like, among the above-described "nitrogen-containing hetero ring". In a certain embodiment, the "nitrogen-containing saturated hetero ring" is a 5- to 8-membered ring group having one N and further one hetero atom selected from O and S, and having a bond on the nitrogen atom constituting the ring. In another embodiment, it is 1-pyrrolidinyl, 1-piperidyl, 1-azepanyl, 1-azocanyl, morpholin-4-yl, thiomorpholin-4-yl, homomorpholin-4-yl, thiazepan-4-yl, or 2-oxa-5-azabicyclo[2.2.1]hept-5-yl.

The "cyclic amine" means a nitrogen-containing hetero ring having a bond on the N atom of the ring.

"—O—CH$_2$CH$_2$—O— binding to the same carbon" refers to a divalent group which forms an acetal as a protected carbonyl group, for example, it is shown in Example Compound 101.

In the present specification, "which may be substituted" means unsubstituted or substituted with 1 to 5 substituents. Further, if plural substituents are present, the substituents may be the same as or different from each other.

Embodiments of the present invention are presented below.

(1) $R^1$ is, in an embodiment, lower alkyl, $C_{3-6}$ cycloalkyl, or halogeno-lower alkyl, in another embodiment, lower alkyl or $C_{3-6}$ cycloalkyl, in a further embodiment, halogeno-lower alkyl, in a still further embodiment, ethyl, isopropyl, tert-butyl, cyclopropyl, or trifluoromethyl, in a still further embodiment, ethyl, isopropyl, tert-butyl, or cyclopropyl, in a still further embodiment, tert-butyl, and in a still further embodiment, trifluoromethyl.

(2) $R^2$ is, in an embodiment, —C(O)$R^{20}$, —C(O)N$R^{21}R^{22}$, -lower alkylene-$R^{20}$, or -lower alkylene-N$R^{21}R^{22}$, in another embodiment, —C(O)$R^{20}$ or —C(O)N$R^{21}R^{22}$, in a further embodiment, —C(O)$R^{20}$, in a still further embodiment, -lower alkylene-$R^{20}$ or -lower alkylene-N$R^{21}R^{22}$, in a still further embodiment, —CH$_2$—$R^{20}$ or —CH$_2$—N$R^{21}R^{22}$, and in a still further embodiment, —CH$_2$—$R^{20}$.

(3) W is, in an embodiment, —CH$_2$—, —N$R^0$—, —O—, —S—, —S(O)—, or —S(O)$_2$—, in another embodiment, —N$R^0$—, —O—, or —S—, and in a further embodiment, —NH—.

(4) $R^3$ is, in an embodiment, $R^{30}$.

(5) $R^{20}$ is, in an embodiment, 1-pyrrolidyl, 1-piperidyl, morpholin-4-yl, thiomorpholin-4-yl, and 1,1-dioxidothiomorpholin-4-yl, which may have 1 to 5 substituents selected from lower alkyl and halogen, in another embodiment, 3,3,4,4-tetrafluoropyrrolidin-1-yl, 4,4-difluoropiperidin-1-yl, morpholin-4-yl, or 1,1-dioxidothiomorpholin-4-yl, in another embodiment, morpholin-4-yl, or 1,1-dioxidothiomorpholin-4-yl, in a further embodiment, morpholin-4-yl, and in a still further embodiment, 1,1-dioxidothiomorpholin-4-yl.

(6) $R^{21}$ is, in an embodiment, -lower alkylene-O$R^0$ or -lower alkylene-hetero ring group, and in another embodiment, (tetrahydro-2H-pyran-4-yl)methyl.

(7) $R^{30}$ is, in an embodiment, $C_{5-10}$ cycloalkyl, aryl, or a hetero ring group, each of which may have 1 to 5 substituents selected from Group $G^3$ on the ring, in another embodiment, $C_{7-10}$ cycloalkyl which may have 1 to 5 substituents selected from lower alkyl, halogen, and OH on the ring, in a still further embodiment, unsubstituted $C_{7-10}$ cycloalkyl, in a still further embodiment, $C_{7-40}$ cycloalkyl which may have 1 to 5 substituents selected from lower alkyl, halogen, and OH on the ring, and has a bridge, in a still further embodiment, cycloheptyl, cyclooctyl, cyclononyl, or cyclodecyl, in a still further embodiment, bicyclo[2.2.1]heptyl, bicyclo[3.1.1]heptyl, bicyclo[2.2.2]octyl, or adamantyl, each of which may have 1 to 5 substituents selected from lower alkyl, halogen, and OH on the ring, in a still further embodiment, bicyclo[2.2.1]heptyl, in a still further embodiment, exo-bicyclo[2.2.1]hept-2-yl, in a still further embodiment, adamantan-1-yl which may have 1 to 5 substituents selected from lower alkyl, halogen, and OH, in a still further embodiment, adamantan-1-yl which may be substituted with 0 to 3 methyl or ethyl, 0 to 3 fluorine, and 0 to 1 OH, in a still further embodiment, adamantan-1-yl which may be substituted with 0 to 3 methyl or ethyl, 0 to 3 fluorine, and 0 to 1 OH at the 3-, 5- and/or 7-position, and in a still further embodiment, 7-oxabicyclo[2.2.1]hept-2-yl which may be substituted with 1 to 5 lower alkyl.

An embodiment of the compound of the formula (I) of the present invention is a compound comprising combinations of one or more of the embodiments of the groups described in (1) to (7) above, and specifically, for example, the following combinations.

(8) The compound, wherein $R^1$ is lower alkyl, $C_{3-6}$ cycloalkyl, or halogeno-lower alkyl, $R^2$ is —C(O)$R^{20}$, W is —NH—, and $R^3$ is $C_{7-10}$ cycloalkyl which may have 1 to 5 substituents selected from lower alkyl, halogen, and OH on the ring.

(9) The compound as described in (8), wherein $R^1$ is lower alkyl or $C_{3-6}$ cycloalkyl.

(10) The compound as described in (9), wherein $R^1$ is ethyl, isopropyl, tert-butyl, or cyclopropyl.

(11) The compound as described in (10), wherein $R^1$ is tert-butyl.

(12) The compound as described in (8), wherein $R^1$ is halogeno-lower alkyl.

(13) The compound as described in (12), wherein $R^1$ is trifluoromethyl.

(14) The compound as described in (8) to (13), wherein $R^{20}$ is 1-pyrrolidyl, 1-piperidyl, morpholin-4-yl, thiomorpholin-4-yl, or 1,1-dioxidothiomorpholin-4-yl, which may have 1 to 5 substituents selected from lower alkyl and halogen.

(15) The compound as described in (14), wherein $R^{20}$ is morpholin-4-yl or 1,1-dioxidothiomorpholin-4-yl.

(16) The compound as described in (8) to (15), wherein $R^3$ is $C_{7-10}$ cycloalkyl which may have 1 to 5 substituents selected from lower alkyl, halogen, and OH on the ring, and has a bridge.

(17) The compound as described in (16), wherein $R^3$ is bicyclo[2.2.1]heptyl, bicyclo[3.1.1]heptyl, bicyclo[2.2.2]octyl, or adamantyl, each of which may have 1 to 5 substituents selected from lower alkyl, halogen, and OH on the ring.

(18) The compound as described in (17), wherein $R^3$ is exo-bicyclo[2.2.1]hept-2-yl.

(19) The compound as described in (17), wherein $R^3$ is adamantan-1-yl which may have 1 to 5 substituents selected from lower alkyl, halogen, and OH.

(20) The compound as described in (19), wherein $R^3$ is adamantan-1-yl which may be substituted with 0 to 3 methyl or ethyl, 0 to 3 fluorine, and 0 to 1 OH.

(21) The compound as described in (20), wherein $R^3$ is adamantan-1-yl which may be substituted with 0 to 3 methyl or ethyl, 0 to 3 fluorine, and 0 to 1 OH at the 3-, 5-, or 7-position.

(22) The compound, wherein $R^1$ is lower alkyl, $C_{3-6}$ cycloalkyl, or halogeno-lower alkyl, $R^2$ is —CH$_2$—$R^{20}$, W is —NH—, and $R^3$ is $C_{7-10}$ cycloalkyl which may have 1 to 5 substituents selected from lower alkyl, halogen, and OH on the ring.

(23) The compound as described in (22), wherein $R^1$ is ethyl, isopropyl, tert-butyl, or cyclopropyl.

(24) The compound as described in (23), wherein $R^1$ is tert-butyl.

(25) The compound as described in (22), wherein $R^1$ is halogeno-lower alkyl.

(26) The compound, as described in (25), wherein $R^1$ is trifluoromethyl.

(27) The compound as described in (22) to (26), wherein $R^{20}$ is 1-pyrrolidyl, 1-piperidyl, morpholin-4-yl, thiomorpholin-4-yl, or 1,1-dioxidothiomorpholin-4-yl, which may have 1 to 5 substituents selected from lower alkyl and halogen.

(28) The compound as described in (22) to (27), wherein $R^3$ is $C_{7-10}$ cycloalkyl which may have 1 to 5 substituents selected from lower alkyl, halogen, and OH on the ring, and has a bridge.

(29) The compound as described in (28), wherein R³ is bicyclo[2.2.1]heptyl, bicyclo[3.1.1]heptyl, bicyclo[2.2.2]octyl, or adamantyl, each of which may have 1 to 5 substituents selected from lower alkyl, halogen, and OH on the ring.

(30) The compound as described in (29), wherein R³ is exo-bicyclo[2.2.1]hept-2-yl.

(31) The compound as described in (29), wherein R³ is adamantan-1-yl which may have 1 to 5 substituents selected from lower alkyl, halogen, and OH.

(32) The compound as described in (31), wherein R³ is adamantan-1-yl which may be substituted with 0 to 3 methyl or ethyl, 0 to 3 fluorine, and 0 to 1 OH.

(33) The compound as described in (32), wherein R³ is adamantan-1-yl which may be substituted with 0 to 3 methyl or ethyl, 0 to 3 fluorine, and 0 to 1 OH at the 3-, 5-, or 7-position.

Examples of the specific compounds encompassed by the present invention include the following compounds:

5-[(1,1-dioxidothiomorpholin-4-yl)carbonyl]-N-(3-ethyladamantan-1-yl)-4-(trifluoromethyl)pyrimidin-2-amine,
N-(3-fluoroadamantan-1-yl)-5-(morpholin-4-ylcarbonyl)-4-(trifluoromethyl)pyrimidin-2-amine,
2-(adamantan-1-ylamino)-N-(tetrahydro-2H-pyran-4-ylmethyl)-4-(trifluoromethyl)pyrimidine-5-carboxamide,
N-adamantan-1-yl-5-[(1,1-dioxidothiomorpholin-4-yl)carbonyl]-4-(trifluoromethyl)pyrimidin-2-amine,
N-adamantan-1-yl-5-[(4,4-difluoropiperidin-1-yl)carbonyl]-4-(trifluoromethyl)pyrimidin-2-amine,
3-({5-[(1,1-dioxidothiomorpholin-4-yl)carbonyl]-4-(trifluoromethyl)pyrimidin-2-yl}amino)adamantan-1-ol,
4,4-dimethyl-1-[5-(morpholin-4-ylcarbonyl)-4-(trifluoromethyl)pyrimidin-2-yl]-1,2,3,4-tetrahydroquinoline,
1-{5-[(1,1-dioxidothiomorpholin-4-yl)carbonyl]-4-(trifluoromethyl)pyrimidin-2-yl}-4,4-dimethyl-1,2,3,4-tetrahydroquinoline,
3-({5-[(1,1-dioxidothiomorpholin-4-yl)carbonyl]-4-isopropylpyrimidin-2-yl}amino)adamantan-1-ol,
rac-N-[(1R,2R,4S)-bicyclo[2.2.1]hept-2-yl]-4-isopropyl-5-(morpholin-4-ylcarbonyl)pyrimidin-2-amine,
rac-N-[(1R,2R,4S)-bicyclo[2.2.1]hept-2-yl]-5-[(1,1-dioxidothiomorpholin-4-yl)carbonyl]-4-isopropyl pyrimidin-2-amine,
rac-N-[(1R,2R,4S)-bicyclo[2.2.1]hept-2-yl]-4-cyclopropyl-5-(morpholin-4-ylcarbonyl)pyrimidin-2-amine,
rac-N-[(1R,2R,4S)-bicyclo[2.2.1]hept-2-yl]-4-cyclopropyl-5-[(1,1-dioxidothiomorpholin-4-yl)carbonyl]pyrimidin-2-amine,
rac-N-[(1R,2S,4S)-7-oxabicyclo[2.2.1]hept-2-yl]-5-[(3,3,4,4-tetrafluoropyrrolidin-1-yl)carbonyl]-4-(trifluoromethyl)pyrimidin-2-amine,
rac-N-[(1R,2R,4S)-bicyclo[2.2.1]hept-2-yl]-4-tert-butyl-5-(morpholin-4-ylcarbonyl)pyrimidin-2-amine,
rac-N-[(1R,2R,4S)-bicyclo[2.2.1]hept-2-yl]-4-tert-butyl-5-[(1,1-dioxidothiomorpholin-4-yl)carbonyl]pyrimidin-2-amine,
3-({4-tert-butyl-5-[(1,1-dioxidothiomorpholin-4-yl)carbonyl]pyrimidin-2-yl}amino)adamantan-1-ol,
N-[(1S,2S,4R)-bicyclo[2.2.1]hept-2-yl]-4-isopropyl-5-(morpholin-4-ylcarbonyl)pyrimidin-2-amine,
N-[(1S,2S,4R)-bicyclo[2.2.1]hept-2-yl]-5-[(1,1-dioxidothiomorpholin-4-yl)carbonyl]-4-isopropyl pyrimidin-2-amine,
3,5-difluoro-7-{[5-(morpholin-4-ylcarbonyl)-4-(trifluoromethyl)pyrimidin-2-yl]amino}adamantan-1-ol,
3-({5-[(1,1-dioxidothiomorpholin-4-yl)carbonyl]-4-(trifluoromethyl)pyrimidin-2-yl}amino)-5,7-difluoro adamantan-1-ol,
N-[(1R,2R,4S)-bicyclo[2.2.1]hept-2-yl]-4-isopropyl-5-(morpholin-4-ylcarbonyl)pyrimidin-2-amine,
N-[(1R,2R,4S)-bicyclo[2.2.1]hept-2-yl]-5-[(1,1-dioxidothiomorpholin-4-yl)carbonyl]-4-isopropyl pyrimidin-2-amine,
3-({5-[(4,4-difluoropiperidin-1-yl)carbonyl]-4-(trifluoromethyl)pyrimidin-2-yl}amino)adamantan-1-ol,
3-({5-[(3,3,4,4-tetrafluoropyrrolidin-1-yl)carbonyl]-4-(trifluoromethyl)pyrimidin-2-yl}amino)adamantan-1-ol,
rac-N-[(1R,2R,4S)-bicyclo[2.2.1]hept-2-yl]-5-(morpholin-4-ylcarbonyl)-4-(trifluoromethyl)pyrimidin-2-amine,
rac-N-[(1R,2R,4S)-bicyclo[2.2.1]hept-2-yl]-5-[(1,1-dioxidothiomorpholin-4-yl)carbonyl]-4-(trifluoromethyl)pyrimidin-2-amine,
5-[(1,1-dioxidothiomorpholin-4-yl)carbonyl]-4-(trifluoromethyl)-N-[(1R,2S,4R)-1,7,7-trimethylbicyclo[2.2.1]hept-2-yl]pyrimidin-2-amine,
N-(3,5-difluoroadamantan-1-yl)-5-[(1,1-dioxidothiomorpholin-4-yl)carbonyl]-4-(trifluoromethyl)pyrimidin-2-amine,
5-(morpholin-4-ylcarbonyl)-N-(3,5,7-trifluoroadamantan-1-yl)-4-(trifluoromethyl)pyrimidin-2-amine,
5-[(1,1-dioxidothiomorpholin-4-yl)carbonyl]-N-(3,5,7-trifluoroadamantan-1-yl)-4-(trifluoromethyl)pyrimidin-2-amine,
rac-N-[(1R,2S,4S)-bicyclo[2.2.1]hept-2-yl]-5-[(1,1-dioxidothiomorpholin-4-yl)carbonyl]-4-(trifluoromethyl)pyrimidin-2-amine,
N-(3,5-dimethyladamantan-1-yl)-5-(morpholin-4-ylcarbonyl)-4-(trifluoromethyl)pyrimidin-2-amine,
N-(3,5-difluoroadamantan-1-yl)-5-(morpholin-4-ylcarbonyl)-4-(trifluoromethyl)pyrimidin-2-amine,
N-bicyclo[2.2.2]oct-1-yl-5-[(1,1-dioxidothiomorpholin-4-yl)carbonyl]-4-(trifluoromethyl)pyrimidin-2-amine,
N-[(1R,2R,4S)-bicyclo[2.2.1]hept-2-yl]-5-[(1,1-dioxidothiomorpholin-4-yl)carbonyl]-4-(trifluoromethyl)pyrimidin-2-amine,
N-bicyclo[2.2.1]hept-1-yl-5-[(1,1-dioxidothiomorpholin-4-yl)carbonyl]-4-(trifluoromethyl)pyrimidin-2-amine,
N-bicyclo[2.2.1]hept-1-yl-5-(morpholin-4-ylcarbonyl)-4-(trifluoromethyl)pyrimidin-2-amine,
N-[(1S,2S,4R)-bicyclo[2.2.1]hept-2-yl]-5-[(1,1-dioxidothiomorpholin-4-yl)carbonyl]-4-(trifluoromethyl)pyrimidin-2-amine,
N-bicyclo[2.2.2]oct-1-yl-5-[(1,1-dioxidothiomorpholin-4-yl)carbonyl]-4-(trifluoromethyl)pyrimidin-2-amine,
N-adamantan-1-yl-5-(morpholin-4-ylcarbonyl)-4-(trifluoromethyl)pyrimidin-2-amine,
rac-N-[(1R,2R,4S)-bicyclo[2.2.1]hept-2-yl]-5-[(4,4-difluoropiperidin-1-yl)methyl]-4-(trifluoromethyl)pyrimidin-2-amine, and
N-adamantan-1-yl-5-[(1,1-dioxidothiomorpholin-4-yl)methyl]-4-(trifluoromethyl)pyrimidin-2-amine.

The compound of the formula (I) may exist in the form of tautomers or geometrical isomers in some cases, depending on the kinds of the substituents. In the present specification, the compound of the formula (I) may be described to be only in the form of one isomer, but the present invention includes other isomers, isolated forms of the isomers, or a mixture thereof.

Further, the compound of the formula (I) may have asymmetric carbon atoms or axial asymmetries in some cases, and correspondingly, it may exist in the form of optical isomers. The present invention includes an isolated form of the optical isomers of the compound of the formula (I) or a mixture thereof.

Moreover, a pharmaceutically acceptable prodrug of the compound of the formula (I) are also included in the present invention. The pharmaceutically acceptable prodrug refers to a compound having a group which can be converted into an amino group, a hydroxyl group, a carboxyl group, or the like by solvolysis or under a physiological condition. Examples of the group for forming a prodrug include the groups as described in Prog. Med., 5, 2157-2161 (1985) or "Pharmaceutical Research and Development", (Hirokawa Publishing Company, 1990), vol. 7, "Drug Design", pp. 163-198.

Moreover, the salt of the compound of the formula (I) refers to a pharmaceutically acceptable salt of the compound of the formula (I), and in some cases, it forms an acid addition salt or a salt with a base, depending on the kind of substituents. Specifically, examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditoluoyl tartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like, and with organic bases such as methylamine, ethylamine, ethanolamine, lysine, ornithine, and the like, salts with various amino acids such as acetyl leucine and the like, and amino acid derivatives ammonium salts, and others.

Further, the present invention includes various hydrates or solvates, and polymorphic substances of the compound of the formula (I) and a salt thereof. Also, the present invention includes the compounds labeled with various radioactive or non-radioactive isotopes.

(Preparation Processes)

The compound of the formula (I) and a salt thereof can be prepared by applying various known synthetic methods, using the characteristics based on their basic skeletons or the kinds of substituents. At this time, depending on the kinds of functional groups, it is in some cases effective from the viewpoint of the preparation techniques to substitute the functional group with an appropriate protecting group (a group which can easily be converted into the functional group), during the steps from starting materials to intermediates. Examples of such a protecting group include the protecting groups as described in "Greene's Protective Groups in Organic Synthesis (4th Edition, 2006)", edited by P. G. M. Wuts and T. W. Greene, which may be appropriately selected and used depending on the reaction conditions. In these methods, a desired compound can be obtained by introducing the protecting group to carry out the reaction, and then, if desired, removing the protecting group.

In addition, the prodrug of the compound of the formula (I) can be prepared by introducing a specific group during the steps from the starting materials to the intermediates, in a similar manner to the above-mentioned protecting groups, or by further carrying out a reaction using the compound of the formula (I) obtained. The reaction may be carried out by employing a method conventionally known to a person skilled in the art, such as common esterification, amidation, dehydration and the like.

Hereinbelow, representative production process for the compound of the formula (I) are described. Each of the production processes can also be carried out with reference to the reference documents cited in the description. Further, the production processes of the present invention are not limited to examples shown below.

(Production Process 1)

[Chem. 11]

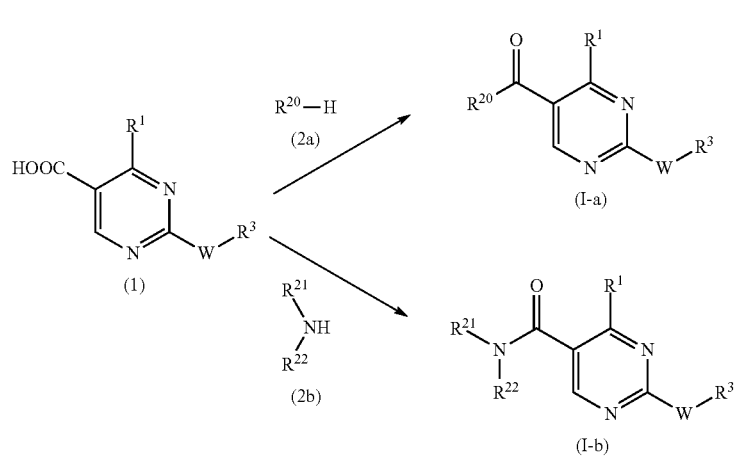

Compounds of the formula (I-a) and the formula (I-b) can be obtained by the reaction of a carboxylic acid (1) with an amine (2).

In this reaction, the carboxylic acid (1) and a cyclic amine (2a) or a non-cyclic amine (2b) are used in equivalent amounts or in an excessive amount of either thereof, and the mixture thereof is stirred from under cooling to under heating, preferably at −20° C. to 60° C., usually for 0.1 hour to 5 days, in a solvent which is inert to the reaction, in the presence of a condensing agent. The solvent as used herein is not particularly limited, but examples thereof include aromatic hydrocarbons such as benzene, toluene, xylene, or the like, halogenated hydrocarbons such as dichloromethane, 1,2-dichloroethane, chloroform, or the like, ethers such as diethyl ether, tetrahydrofuran, dioxane, dimethoxyethane, or the like, N,N-dimethylformamide, N-methyl-2-pyrrolidone, dimethyl sulfoxide, ethyl acetate, acetonitrile, or water, and a mixture thereof. Examples of the condensing agent include 1-(3-dimethylaminopropyl)-3-ethylcarbodiimide, dicyclohexylcarbodiimide, 1,1'-carbonyldiimidazole, diphenyl phosphoryl azide, phosphorous oxychloride, and the like, but are not limited to these. It may be preferable to use an additive (for example, 1-hydroxybenzotriazole) for the reaction in some cases. It may be advantageous for the smooth progress of the reaction to carry out the reaction in the presence of an organic base such as triethylamine, N,N-diisopropylethylamine, N-methylmorpholine, or the like, or an inorganic base such as potassium carbonate, sodium carbonate, potassium hydroxide, or the like, in some cases.

Further, a method, in which the carboxylic acid (1) is converted to its reactive derivative, and then reacted with the amine (2), can also be used. Examples of the reactive derivative of the carboxylic acid include an acid halide obtained by the reaction with a halogenating agent such as phosphorous oxychloride, thionyl chloride and the like, a mixed acid anhydride obtained by the reaction with isobutyl chloroformate and the like, and an active ester obtained by the condensation with 1-hydroxybenzotriazole and the like. The reaction of the reactive derivative with the amine (2) can be carried out from under cooling to under heating, preferably at −78° C. to 60° C., in a solvent which is inert to the reaction, such as halogenated hydrocarbons, aromatic hydrocarbons, ethers, and the like.

Examples of the reference documents include "Organic Functional Group Preparations", edited by S. R. Sandler and W. Karo, 2nd edition, vol. 1, Academic Press Inc., 1991, "Jikken Kagaku Koza (Course in Experimental Chemistry, 5th edition (vol. 16)", edited by The Chemical Society of Japan, Maruzen, 2005, or the like.

(Production Process 2)

[Chem. 12]

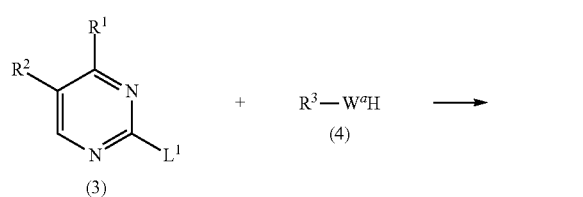

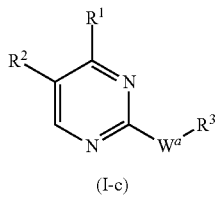

(I-c)

(In the formula, $W^a$ represents —$NR^0$—, —O—, or —S—, or $R^3$—$W^aH$ represents a cyclic amine; and $L^1$ represents a leaving group. The same shall apply hereinafter.)

A compound of the formula (I-c) can be obtained by the reaction of a compound (3) with a compound (4). Examples of the leaving group include halogen, methylsulfinyl, and methylsulfonyl group.

In this reaction, the compound (3) and the compound (4) are used in equivalent amounts or in an excessive amount of either thereof, and the mixture is stirred from under cooling to heating with reflux, preferably at 0° C. to 150° C., usually for 0.1 hour to 5 days, in a solvent which is inert to the reaction or without a solvent. It may be advantageous in some cases for the smooth progress of the reaction to heat the reaction mixture by radiation with microwave. The solvent as used herein is not particularly limited, but examples thereof include aromatic hydrocarbons such as benzene, toluene, xylene, and the like, ethers such as diethyl ether, tetrahydrofuran, dioxane, dimethoxyethane, and the like, halogenated hydrocarbons, such as dichloromethane, 1,2-dichloroethane, chloroform, and the like, N,N-dimethylformamide, N,N-dimethylacetamide, N-methyl-2-pyrrolidone, dimethylsulfoxide, ethyl acetate, acetonitrile, and a mixture thereof. It may be advantageous for the smooth progress of the reaction to carry out the reaction in the presence of an organic base such as triethylamine, N,N-diisopropylethylamine, N-methylmorpholine, or the like, or an inorganic base such as potassium carbonate, sodium carbonate, cesium carbonate, potassium hydroxide, or the like, in some cases.

Examples of the reference documents include "Organic Functional Group Preparations", edited by S. R. Sandler and W. Karo, 2nd edition, vol. 1, Academic Press Inc., 1991, "Jikken Kagaku Koza (Experimental Chemistry Course, 5th edition (vol. 14)", edited by The Chemical Society of Japan, Maruzen, 2005, or the like.

(Production Process 3)

[Chem. 13]

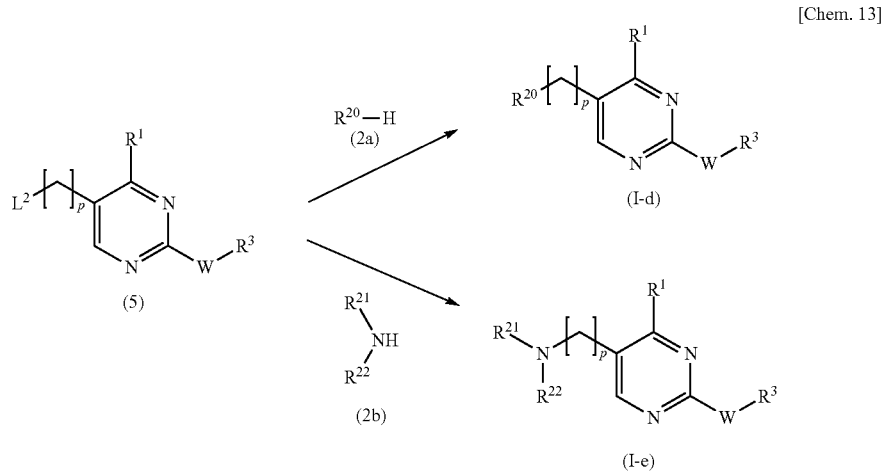

(In the formula, $L^2$ represents a leaving group and p represents 1 to 6. The same shall apply hereinafter.)

Compounds of the formula (I-d) and the formula (I-e) can be obtained by the reaction of a compound (5) with the compound (2). Examples of the leaving group include halogen, methanesulfonyloxy, and p-toluenesulfonyloxy group. The reaction condition is the same as for Production Process 2.

(Production Process 4)

[Chem. 14]

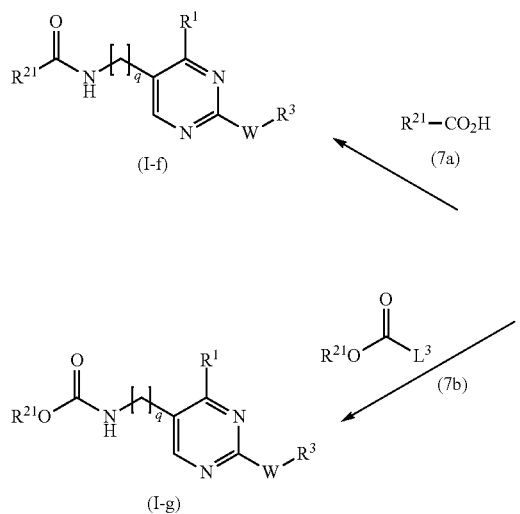

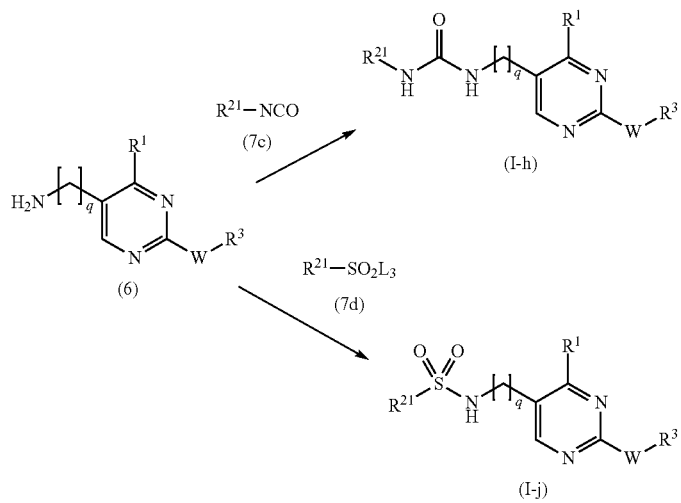

(In the formula, $L^3$ represents a leaving group and q represents 0 to 6. The same shall apply hereinafter.)

An amide compound (I-f), a carbamate compound (I-g), a urea compound (I-h), and a sulfonamide compound (I-j) can be obtained by using a compound (6) as a starting material. Examples of the leaving group for $L^3$ include halogen and the like. Alternatively, various acid anhydrides can be used.

The amide compound (I-f) is obtained by the reaction of the compound (6) with a carboxylic acid (7a) in the presence of a condensing agent in the similar manner to Production Process 1. Further, it is also obtained by converting the carboxylic acid (7a) into its reactive derivative in the similar manner to Production Process 1, and then reacting with the compound (6). The compounds (I-g) to (I-j) are obtained by reacting the compound (6) with each corresponding carbonic ester derivative (7b), isocyanate (7c), and sulfonyl halide (7d) under the same condition as described for the reactive derivative of the carboxylic acid above.

(Production Process 5)

[Chem. 15]

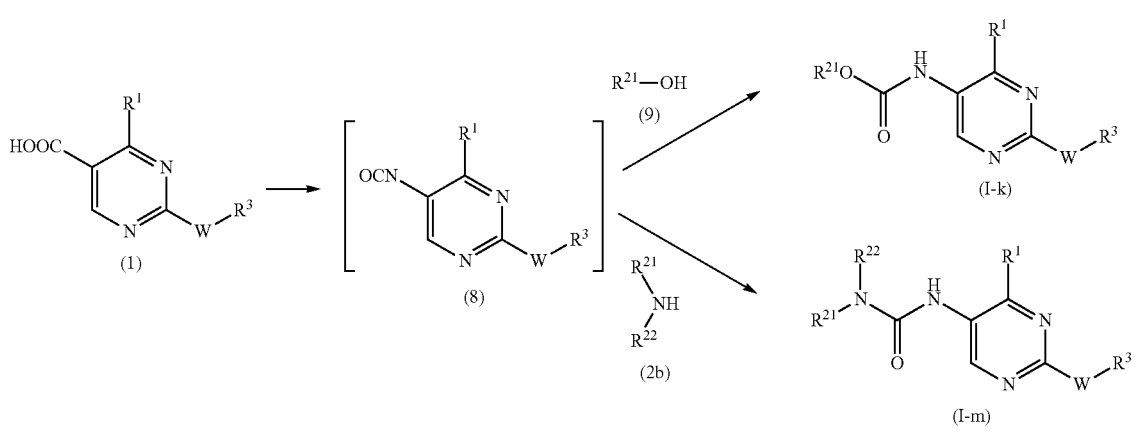

Compounds of the formula (I-k) and the formula (I-m) can be obtained by converting the carboxylic acid (1) to a corresponding isocyanate (8) and then reacting with an alcohol or phenol (9), or the amine (2b).

The isocyanate (8) can be obtained and isolated by Curtius rearrangement of a corresponding acid azide compound, Hoffmann rearrangement of a primary amide compound, or the like. The acid azide can be obtained by reacting the carboxylic acid (1) with an azide salt such as sodium azide and the like in the presence of an activating agent, or by reacting a carboxylic acid with diphenylphosphoric acid azide.

(Production Process 6)

This reaction is carried out by using the compounds (3) and (13) in equivalent amounts or in an excessive amount of either thereof, and stirring the mixture thereof from at room temperature to under heating with reflux, usually for 0.1 hour to 5 days, in the presence of a nickel catalyst in a solvent which is inert to the reaction. The present reaction is preferably carried out under an inert gas atmosphere. The solvent as used herein is not particularly limited, but examples thereof include aromatic hydrocarbons such as benzene, toluene, xylene, and the like, ethers such as diethylether, tetrahydrofuran, dioxane, dimethoxyethane, and the like, and a mixed

[Chem. 16]

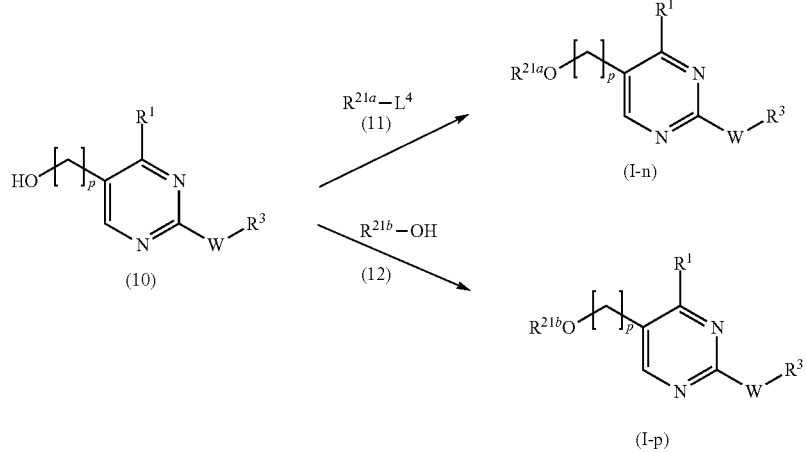
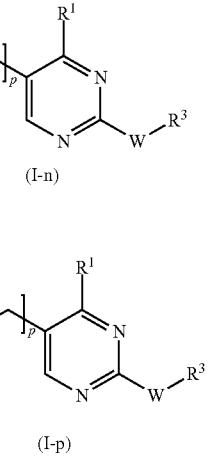

(In the formula, $R^{21a}$ represents alkyl, cycloalkyl or the like which may be substituted, $R^{21b}$ represents aryl or the like which may be substituted, and $L^4$ represents a leaving group. The same shall apply hereinafter.)

A compound of the formula (I-n) can be obtained by the reaction of a compound (10) with a compound (11). Examples of the leaving group include halogen, methanesulfonyloxy, and p-toluenesulfonyloxy group. The reaction condition is similar to Production Process 2.

A compound of the formula (I-p) can be obtained by the Mitsunobu reaction of the compound (10) and a compound (12).

(Production Process 7)

[Chem. 17]

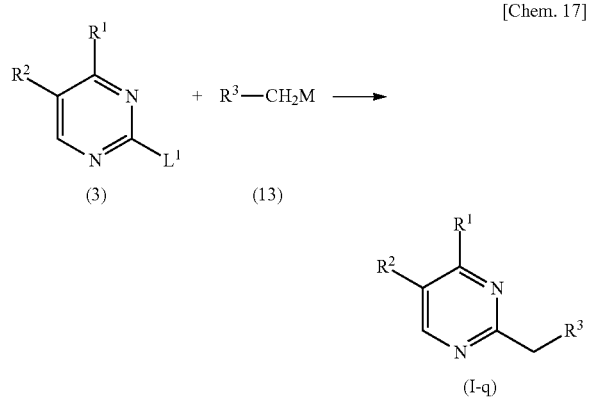

(In the formula, M represents metals such as zinc and the like. The same shall apply hereinafter.)

A compound of formula (I-q) can be obtained by the reaction of the compound (3) with a compound (13). Examples of the leaving group include halogen methanesulfonyloxy, p-toluenesulfonyloxy, and trifluoromethanesulfonyloxy group.

solvent thereof. As the nickel catalyst, dichlorobis(triphenylphosphine)nickel (II) and the like are preferable.

Various substituents on $R^1$, $R^2$, and $R^3$ in the compound of the formula (I) can be easily converted to other functional groups by using the compound of the formula (I) as a starting material by the methods described in Examples to be described later, a method apparent to a skilled person in the art, or a modified method thereof. For example, any combination of the processes that can be usually employed by a skilled person in the art, such as O-alkylation, N-alkylation, reduction, hydrolysis, amidation, and the like, can be carried out.

(Preparation of Starting Compounds)

The starting compounds in the above production processes can be prepared, for example, by the methods as below, the methods as described in Preparative Examples to be described later, the known methods, or a modified method thereof.

(Starting Material Synthesis 1)

[Chem. 18]

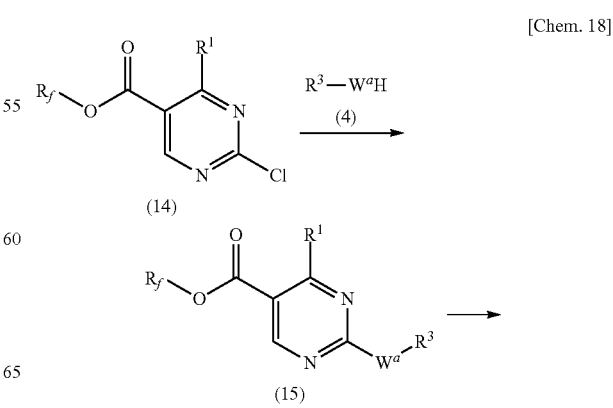

-continued

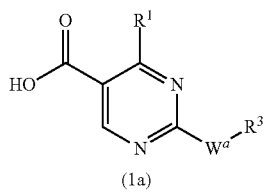

(1a)

(In the formula, $R_f$ represents a lower alkyl group).

A compound (15) can be obtained by the reaction of a compound (14) with the compound (4). The reaction condition is similar to Production Process 2 above. The compound (1a) can be obtained by a usual hydrolysis method from the compound (15).

(Starting Material Synthesis 2)

[Chem. 19]

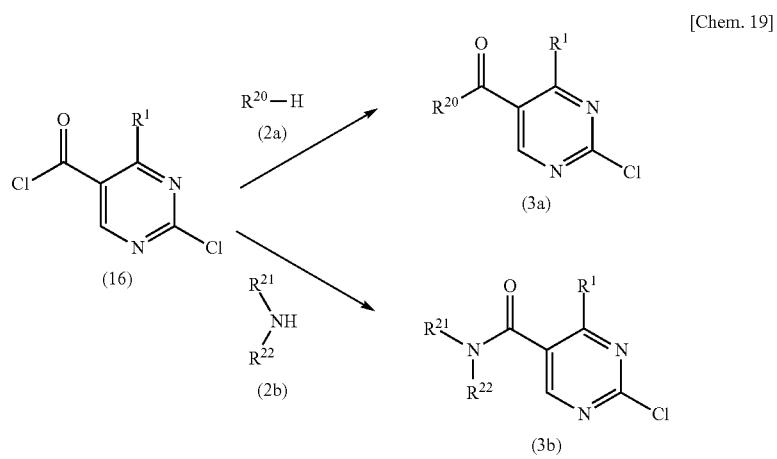

Compounds (3a) and (3b) can be obtained by the reaction of a compound (16) with the compound (2). The reaction condition is similar to the condition as described for the reactive derivative of the carboxylic acid in Production Process 1 above. The reaction temperature is preferably from −78° C. to −20° C.

(Starting Material Synthesis 3)

[Chem. 20]

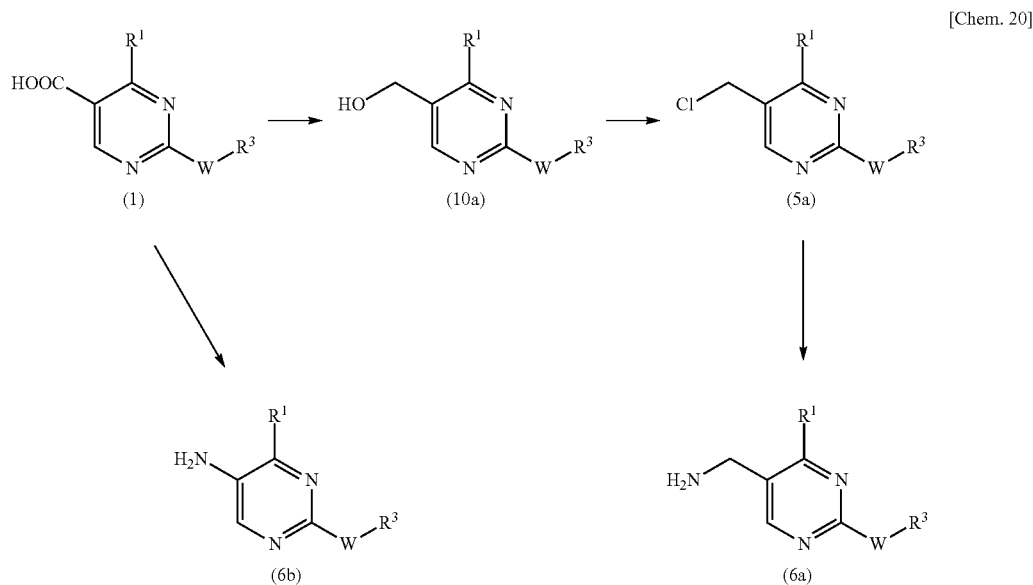

A compound (10a) can be obtained by subjecting the compound (1) to a reduction reaction. For example, the compound (10a) can be obtained by reacting the compound (1) with isobutyl chloroformate, followed by reduction using sodium borohydride.

A compound (5a) can be obtained by reacting the compound (10a) with a chlorinating agent such as thionyl chloride and the like.

A compound (6a) can be obtained by converting the functional group of the compound (5a), for example, by reacting the compound (5a) with potassium phthalimide, followed by decomposition using hydrazine.

A compound (6b) can be obtained by the rearrangement reaction of the compound (1). For example, the compound (6b) can be obtained by reacting the compound (1) with diphenyl phosphoric acid azide, followed by heating in the presence of tert-butyl alcohol and then deprotection.

The compounds of the formula (I) can be isolated and purified as their free compounds, salts, hydrates, solvates, or polymorphic substances thereof. The salts of the compound of the formula (I) can also be prepared by carrying out a conventional salt formation reaction.

Isolation and purification are carried out by employing general chemical operations such as extraction, fractional crystallization, various types of fractionation chromatography, and the like.

Various isomers can be prepared by selecting an appropriate starting compound or separated by making use of the difference in the physicochemical properties between the isomers. For example, the optical isomers are obtained by means of general optical resolution methods of racemic products (for example, fractional crystallization for inducing diastereomer salts with optically active bases or acids, chromatography using a chiral column or the like, and others), and further, the isomers can also be prepared from an appropriate optically active starting compound.

The pharmacological activity of the compound of the formula (I) was confirmed by the following tests.

Test Example 1

Human CB2-Mediated Cyclic AMP (cAMP) Production Inhibition Assay

The present test was performed using CHO cells expressing human CB2 ("Molecular Pharmacology", 1995, vol. 48, p. 443-450).

A suspension of human CB2-expressing CHO cells (2.5× $10^3$/mL), and an assay medium added with a test substance and forskolin (final concentration 0.5 μM) were mixed in the equivalent amounts, and incubated at room temperature for 30 minutes. Then, the cAMP concentration in the cell lysis solution obtained by the addition of a 0.6% Triton X-100 solution was measured using a cAMP kit (manufactured by Cisbio international). The assay medium includes an α-MEM medium manufactured by Invitrogen, supplemented with 0.02% CHAPS, 1 mM isobutylmethyl xanthine, and 0.5 mg/mL bovine serum albumin. As the cAMP concentration in the cell suspension without the addition of forskolin was set as a cAMP increase rate of 0% and the cAMP concentration in the cell suspension with the addition of forskolin was set as a cAMP increase rate of 100%, the inhibitory rate of the intracellular cAMP increase at 30 nM test substance was determined.

The results are shown in Table 1. In the table, Ex indicates Example Compound number below, and Inh indicates an inhibitory rate of cAMP increase.

TABLE 1

| Ex | Inh (%) |
|---|---|
| 45 | 79 |
| 55 | 63 |
| 64 | 85 |
| 67 | 76 |
| 72 | 99 |
| 79 | 74 |
| 83 | 84 |
| 88 | 76 |
| 103 | 67 |
| 106 | 74 |
| 109 | 80 |
| 122 | 70 |
| 133 | 80 |
| 138 | 49 |
| 143 | 70 |
| 161 | 75 |
| 166 | 70 |

Test Example 2

Inhibitory Effect on Hind Paw Weight Distribution in Adjuvant-Induced Arthritis Rats For the experiment, female Lewis rats (7-8 week old) were used. 50 μL of inactivated *Mycobacterium tuberculosis* H37 Ra (manufactured by DIFCO) suspended with liquid paraffin to 10 mg/mL was administered subcutaneously into the right hindlimb footpad. The test substance was orally administered next day, the weights of the left and right hind paws after an arbitrary time were measured using Incapasitance Tester (manufactured by Columbus Instruments), and the weight distribution between left and right was calculated. As the weight distribution of the group administered with the vehicle was set as the inhibitory rate of 0% and the weight distribution of the normal group was set as the inhibitory rate of 100%, the inhibitory rate of the test substance was calculated.

The results are shown in Table 2. In the table, Ex indicates Example Compound number below, Inh indicates an inhibitory rate of the weight distribution, and the description after to @ means the administration amount.

TABLE 2

| Ex | Inh (%) |
|---|---|
| 64 | 52@0.1 mpk |
| 72 | 40@0.1 mpk |
| 103 | 41@0.3 mpk |
| 109 | 35@0.3 mpk |
| 122 | 45@0.1 mpk |
| 166 | 66@0.3 mpk |

As a result of the test above, it was demonstrated that the compound of the formula (I) has an excellent CB2 agonistic action and can be used for preventing and/or treating diseases related to CB2 shown below, or the like.

Inflammatory diseases, for example, diseases such as, dermatitis such as dermatitis, contact dermatitis, allergic dermatitis, atopic dermatitis, poison ivy dermatitis/cosmetic poisoning, allergic rhinitis, seasonal allergic rhinitis, chronic bronchitis, bronchitis, pneumonia, idiopathic interstitial pneumonia, reflux esophagitis, gastritis, atopic gastritis, pancreatitis, myocarditis, pericarditis, endocarditis, hepatitis, inflammatory bowel disease, colitis, refractory colitis, ulcerative colitis, inflammatory enteritis, regional ileitis, nephritis, glomerulonephritis, nephritic syndrome, vasculitis, allergic granulomatous vasculitis, ulcerative vasculitis, angiitis, rheumatoid spondylitis, arthritis, osteoarthritis, psoriatic arthritis, gouty arthritis, juvenile arthritis, reactive arthritis, undifferentiated spondylarthritis, retinitis, uveitis, retinal meningitis, conjunctivitis, allergic conjunctivitis, keratoconjunctivitis, infective conjunctivitis, polydrteritis nodosa, thyroiditis, polymyositis, gingivitis, fever, tendinitis, bursitis, cystitis, ankylosing spondylitis, encephalitis, meningitis, malignant meningitis, bacterial cerebro spinal meningitis, cytomegalovirus meningitis, neuritis, sunburn, burns, rheumatic fever, vulvar vestibulitis, stomatitis, acute vaginitis, balanitis, balanoposthitis, chronic inflammation of mucous membranes, dermatomyositis, Hashimoto's thyroiditis, chronic inflammatory diseases (rheumatoid arthritis, osteoarthritis, rheumatoid spondylitis, gouty arthritis, juvenile arthritis, pain associated with multiple sclerosis), and the like.

Pain, for example, diseases such as, rheumatoid arthritis pain, osteoarthritis pain, chronic pain, inflammatory chronic pain, acute pain, acute peripheral pain, low back pain, chronic low back pain, back pain, headaches, migraines, toothache, inflammatory pain, nociceptive pain, neurogenic pain, neuropathic pain, muscle pain, fibromyalgia syndrome, visceral pain, pelvic pain, neuralgia, sciatica, postherpetic neuralgia, diabetic pain, HIV-related pain, cancer pain, trigeminal neuralgia, neurogenic low back pain, fibromuscular skeltal pain, psychogenic pain, menstrual pain, pain illusion, hyperalgesia, hypoalgesia, toothache, neck pain, pain associated with viral infection, pain associated with influenza virus infection, functional abdominal pain (nonulcer gastrointestinal disorders, noncardiac pain, irritable bowel syndrome, and the like), pain associated with myocardial ischemia, multiple sclerosis pain, pain caused by trauma/toxin, allodynia, post-stroke pain, sprains, muscle strain, and the like.

Cancers and tumors, for example, diseases such as, cancer of the immune system, lung cancer, colon cancer, malignant brain tumors, skin cancer, uterine cancer, breast cancer, prostate cancer, leukemia, benign skin tumors, cancerous tumors and papillomas, small cell lung cancer, glioblastoma, medulloepithelioma, medulloblastoma, neuroblastoma, tumors caused in embryo, astrocytoma, astroblastoma, ependymoma, oligodendroglioma, plexus tumor, neuroepithelial tumor, epiphyseal tumor, ependymoblastoma, neuroectodermal tumor, sarcomatosis, malignant melanoma, schwannoma, lymphoma, glioma, thyroid epithelioma, neuroblastoma, cutaneous T-cell lymphoma, glioma, tumor, pineal body tumors, malignant myeloma, and the like.

Respiratory diseases, for example, diseases such as, respiratory distress syndrome, acute respiratory distress syndrome, pulmonary tuberculosis, cough, bronchial asthma, cough based on increased airway hyperreactivity (bronchitis, flu syndrome, asthma, obstructive pulmonary disease, and the like), flu syndrome, anti-cough, airway hyperreactivity, tuberculosis disease, asthma (airway inflammatory cell infiltration, increased airway hyperresponsiveness, bronchoconstriction, mucus hypersecretion, and the like), chronic obstructive pulmonary disease, emphysema, pulmonary fibrosis, idiopathic pulmonary fibrosis, cough, reversible airway obstruction, adult respiratory disease syndrome, pigeon fancier's disease, farmer's lung, bronchopulmonary dysplasia, airway disorder, emphysema, and the like.

Liver diseases, for example, diseases such as liver fibrosis, liver cirrhosis, chronic liver cirrhosis, and the like.

Brain diseases, for example, diseases such as brain damage, cerebral infarction, stroke, brain tumor therapeutics, cerebral ischemia, acute cerebral ischemia, cerebrovascular ischemia, and the like.

Eye diseases, for example, diseases such as ocular hypertension, cataract, glaucoma, retinal detachment, retinopathy, retinal disease, eye globe disorders, corneal ulcer, and the like.

Skin diseases, for example, diseases such as pruritus, scleroderma, senile xerosis, sclerema, and the like.

Cardiovascular disease, for example, diseases such as angina pectoris, unstable angina, myocardial infarction, heart failure, multiple sclerosis, arteriosclerosis, atherosclerosis, arrhythmia, hypertension, ischemic heart disease, heart attack, cardiac ischemia, cardioplegic, telangiectasia, hypertension, hypotension, restenosis after coronary stent, thrombosis, vascular disease, cardiovascular symptoms associated with vascular vessel remodeling, and the like.

Allergic diseases, for example, diseases such as anaphylaxis, gastrointestinal allergy, allergic gastroenteritis, allergic asthma, atopic asthma, allergic bronchopulmonary aspergillosis, pollen allergy, drug allergy, and the like.

Digestive diseases, for example, diseases such as gastrointestinal diseases, constipation, diarrhea, secretory diarrhea, vomiting (cancer chemotherapy-induced vomiting), nausea, nausea especially associated with chemotherapy, nausea associated with AIDS wasting syndrome, gastroesophageal reflux disease, peptic ulcer, irritable bowel syndrome, functional gastrointestinal disorder, inflammatory bowel disease, ulcerative colitis, and the like.

Genitourinary diseases, for example, diseases such as dysmenorrhea and the like.

Immune diseases, for example, diseases such as immunodeficiency, immune regulation, autoimmune diseases, T cell lymphoma, psoriasis, plaque psoriasis, rheumatoid arthritis, osteoporosis, sepsis, septic shock, systemic lupus erythematosus, autoimmune hemolytic anemia, AIDS, and the like.

Complications associated with transplant, for example, diseases such as rejection after organ transplantation, graft-versus-host disease, and the like.

Neurological diseases, for example, diseases such as neurodegenerative disease, depressive illness, manic depression, nausea, dizziness, phantom limb, nerve disorder, peripheral neuropathy, nerve damage, traumatic neurosis, dementia, senile dementia, dementia, senile dementia, Alzheimer's disease, psychosis, schizophrenia, Pick's disease, Huntington's chorea, chorea, Parkinson's disease, Creutzfeldt-Jakob disease, motor neuron disease, multi-infarct dementia, anoxia, vitamin deficiency, age-related memory impairment, schizophrenia, depression, anxiety, panic disorder, agoraphobia, social phobia, obsessive-compulsive disorder, post-traumatic stress disorder, memory impairment, amnesia, appetite regulation, anorexia, anorexia nervosa, bulimia nervosa, functional disorders, circadian rhythm disorders, sleep disorders, sleep abnormalities, insomnia, hypersomnia, sleep apnea, drug addiction, heartburn, dysphagia, pelvic hypersensitivity, neurodegeneration (associated with stroke, cardiac arrest, traumatic brain injury, spinal problems), movement disorders, convulsions, muscle cramps, tremor, paresthesia, hypersensitivity, and the like.

Besides, diseases such as Guillain-Barre syndrome, Paget's disease, chronicfrailty, aversion, myasthenia gravis, diabetes, type I diabete, ischemic, spontaneous pneumothorax, neural retraction, urticaria, Sjogren's syndrome, spinal cord injury, traumatic cartilage injury, epilepsy, transient ischemic attack, opportunistic infections (HIV and the like), lichen planus, pemphigus, epidermolysis bullosa, excessive formation scar, keloids, arthritis, cardiac ischemia, infarction, serum sickness, renal ischemia, aphthous ulcer, Crohn's disease, celiac disease, aplastic anemia, Hodgkin's disease, nephrotic syndrome, endotoxic shock, hypotension shock, reduction in fertility, Tourette's syndrome, suppression of memory, eczema, sarcoidosis, adult respiratory distress syndrome, coronary artery disease, melanoma, Graves' disease, Goodpasture's syndrome, amylosis, diseases affecting the plasma cell lines, delayed or immediate hypersensitivity, parasitic/viral or bacterial infection, spine injuries, dizziness, obesity diseases, connective tissue diseases, diseases affecting lymphoid hematopoietic, amyotrophic lateral sclerosis, associated cachexia syndrome, associated muscle cramps, bacterial meningitis, and the like.

A pharmaceutical composition containing one or two or more kinds of the compound of the formula (I) or a salt thereof as an active ingredient can be prepared in accordance with a generally used method, using an excipient, that is, a pharmaceutical excipient, a pharmaceutical carrier, or the like, that is usually used in the art.

Administration may be carried out in any form of oral administration via tablets, pills, capsules, granules, powders, liquid preparations, or the like, or of parenteral administration via injections such as intraarticular, intravenous, intramuscular, or others, suppositories, eye drops, eye ointments, percutaneous liquid preparations, ointments, percutaneous patches, transmucosal liquid preparations, transmucosal patches, inhalations, and the like.

Regarding the solid composition for oral administration, tablets, powders, granules, or the like are used. In such a solid composition, one or more active ingredients are mixed with at least one inactive excipient. According to the conventional methods, the composition may contain inactive additives, for example, a lubricant, a disintegrator, a stabilizer, and a solubilizing aid. As occasion demands, tablets or pills may be coated with a sugar coating, or a film of a gastric or enteric material.

The liquid composition for oral administration includes pharmaceutically acceptable emulsions, solutions, suspensions, syrups, elixirs, or the like, and contains a generally used inert diluent, for example, purified water or ethanol. In addition to the inert diluent, the liquid composition may contain adjuvants such as a solubilizing agent, a moisturizing agent, and a suspending agent, a sweetener, a flavor, an aroma, and an antiseptic.

Injections for parenteral administration include sterile, aqueous or non-aqueous solutions, suspensions, or emulsions. As the aqueous solvent, for example, distilled water for injection or physiological saline is included. Examples of the non-aqueous solvent include alcohols such as ethanol and the like. Such a composition may further contain a tonicity agent, an antiseptic, a moisturizing agent, an emulsifying agent, a dispersing agent, a stabilizer, or a solubilizing aid. These are sterilized, for example, by filtration through a bacteria-retaining filter, blending with bactericides, or irradiation. In addition, these can also be used by producing a sterile solid composition, and dissolving or suspending it in sterile water or a sterile solvent for injection prior to its use.

The agent for external use includes ointments, plasters, creams, jellies, cataplasms, sprays, lotions, eye drops, eye ointments, and the like. The agents contain generally used ointment bases, lotion bases, aqueous or non-aqueous liquid preparations, suspensions, emulsions, and the like.

As the transmucosal agents such as an inhalation, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate propellant, for example, a suitable gas such as chlorofluoroalkane, hydrofluoroalkane, carbon dioxide, and the like.

In oral administration, the daily dose is generally from about 0.001 to 100 mg/kg, preferably from 0.1 to 30 mg/kg, and more preferably 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided, depending on the individual case by taking symptoms, ages, and genders and the like into consideration.

The compound of the formula (I) can be used in combination with various agents for treating or preventing the above-described diseases for which the compound of the formula (I) is considered to be effective. The combined preparation may be administered simultaneously, or separately and continuously, or at a desired time interval. The preparations to be co-administered may be prepared individually, or may be a pharmaceutical composition containing various agents for treating or preventing the above-described diseases for which the compound of the formula (I) is considered to be effective, and the compound of the formula (I).

EXAMPLES

Hereinbelow, the production processes of the compound of the formula (I) and starting compounds therefor are described in more detail with reference to Examples. The present invention is not limited to the compounds as described in Examples below. In addition, production processes of the starting compounds are shown in the Preparative Examples. Further, the production processes for the compound of the formula (I) is not limited only to the production processes of specific Examples below, and the compound of the formula (I) can be prepared in accordance with a combination of these production processes, or a method apparent to a person skilled in the art.

The following abbreviations are sometimes used in Preparative Examples, Examples, and Tables below.

PEx: Preparative Example number, Ex: Example number, Syn: Example number in which the corresponding compound was produced using the same method, PSyn: Preparative Example number in which the corresponding compound was produced using the same method, Str: Structural Formula, DAT: Physicochemical data, EI+: m/z value in the mass spectrometry (ionization EI, unless otherwise mentioned, representing $(M)^+$), ESI+: m/z value in the mass spectrometry (ionization ESI, unless otherwise mentioned, representing $(M+H)^+$), ESI−: m/z value in the mass spectrometry (ionization ESI, unless otherwise mentioned, representing $(M-H)^-$), NMR1: δ (ppm) in $^1$H NMR in DMSO-$d_6$, NMR2: δ (ppm) in $^1$H NMR in CDCl$_3$, s: singlet line (spectrum), d: double line (spectrum), t: triplet line (spectrum), q: quartet line (spectrum), br: broad line (spectrum) (ex.: br-s), RT: retention time (min) in HPLC, MeOH: methanol, $[\alpha]_D^t$: specific optical rotation at a temperature t° C., as measured with a sodium-D line. HCl in the structural formula represents hydrochloride, the number before HCl means a molar ratio. For example, 2HCl means dihydrochloride. In addition, Chiral in the structural formula indicates that it is an optically active product.

Preparative Example 1

A mixture of methyl 4,4-dimethyl-3-oxopentanoate (10 g) and N,N-dimethyl formamide dimethyl acetal (9.5 mL) was stirred at 75° C. for 2 hours. To the reaction mixture were added N,N-dimethyl formamide (100 mL), S-methylisothiourea sulfate (2:1) (9.7 g), and sodium acetate (11.4 g), followed by stirring at 90° C. for 15 hours. The reaction mixture was cooled to room temperature, and water was added thereto. The aqueous layer was extracted with ethyl acetate and the organic layer was washed with water and saturated brine. The organic layer was dried over anhydrous magnesium sulfate, then filtered, and concentrated. The obtained residue was purified by silica gel column chromatography (eluent: hexane-ethyl acetate) to obtain methyl 4-tert-butyl-2-(methylsulfanyl)pyrimidine-5-carboxylate (8.4 g) as a colorless oily substance.

Preparative Example 2

To a mixture of 3-chloroperbenzoic acid (20 g) and dichloromethane (120 mL) was added dropwise a solution of methyl 4-tert-butyl-2-(methylsulfanyl)pyrimidine-5-carboxylate (8.4 g) in dichloromethane (100 mL) under ice-cooling. The reaction mixture was stirred at room temperature for 5 hours, and then a saturated aqueous sodium carbonate solution was added thereto. The aqueous layer was extracted with chloroform and the organic layer was washed with water. The organic layer was dried over anhydrous magnesium sulfate, then filtered, and concentrated. The obtained residue was purified by silica gel column chromatography (eluent: hexane-ethyl acetate) to obtain methyl 4-tert-butyl-2-(methylsulfonyl)pyrimidine-5-carboxylate (4.2 g) as a white solid.

Preparative Example 3

To a mixture of ethyl 4-isopropyl-2-(methylsulfonyl)pyrimidine-5-carboxylate (500 mg) and 1,4-dioxane (10 mL) was added exo-2-aminonorbornane (612 mg) at room temperature, and the mixture was stirred at the same temperature for 2 hours. To the reaction mixture was added water, and the aqueous layer was extracted with ethyl acetate. The organic layer was washed with water and saturated brine, and dried over anhydrous magnesium sulfate, and then the solvent was evaporated under reduced pressure. The residue was purified by silica gel column chromatography (eluent: hexane-ethyl acetate) to obtain ethyl rac-2-[(1R,2R,4S)-bicyclo[2.2.1]hept-2-ylamino]-4-isopropylpyrimidine-5-carboxylate (470 mg) as a white solid.

Preparative Example 4

To a mixture of ethyl 4-isopropyl-2-(methylsulfonyl)pyrimidine-5-carboxylate (400 mg), (1S,2S,4R)-bicyclo[2.2.1] heptan-2-aminehydrochloride (347 mg), and 1,4-dioxane (8 mL) was added N,N-diisopropyl ethylamine (1 mL) at room temperature, followed by stirring at the same temperature for 16 hours. To the reaction mixture was added water, and the aqueous layer was extracted with ethyl acetate. The organic layer was washed with water and saturated brine, and dried over anhydrous magnesium sulfate, and then the solvent was evaporated under reduced pressure. The residue was purified by silica gel column chromatography (eluent: hexane-ethyl acetate) to obtain ethyl 2-[(1S,2S,4R)-bicyclo[2.2.1]hept-2-ylamino]-4-isopropylpyrimidine-5-carboxylate (417 mg) as a pale yellow solid.

Preparative Example 5

To a mixture of methyl 2-chloro-4-(trifluoromethyl)pyrimidine-5-carboxylate (4.0 g), rac-(1R,2R,4S)-bicyclo[2.2.1] heptan-2-amine (3.7 g), and 1,4-dioxane (60 mL) was added N,N-diisopropyl ethylamine (4.3 mL) at room temperature, and the mixture was stirred at the same temperature for 19 hours. To the reaction mixture were added water and 1 M hydrochloric acid, followed by extraction with ethyl acetate. The organic layer was washed with water and saturated brine, and dried over anhydrous magnesium sulfate, and then the solvent was evaporated under reduced pressure to obtain methyl rac-2-[(1R,2R,4S)-bicyclo[2.2.1]hept-2-ylamino]-4-(trifluoromethyl)pyrimidine-5-carboxylate (5.2 g) as a yellowish white solid.

Preparative Example 6

A mixture of methyl 2-chloro-4-(trifluoromethyl)pyrimidine-5-carboxylate (0.30 g), 2,4-dichlorobenzyl amine (818 µL), and 1,4-dioxane (3 mL) was stirred at room temperature for 21 hours. To the reaction liquid was added ethyl acetate (30 mL), washed with saturated brine (10 mL), and dried over anhydrous magnesium sulfate, and then the solvent was evaporated under reduced pressure. The residue was purified by silica gel column chromatography (eluent: hexane-ethyl acetate) to obtain methyl 2-(2,4-dichlorobenzylamino)-4-(trifluoromethyl)pyrimidine-5-carboxylate (446 mg) as a colorless solid.

Preparative Example 7

To a mixture of methyl rac-2-[(1R,2R,4S)-bicyclo[2.2.1] hept-2-ylamino]-4-(trifluoromethyl)pyrimidine-5-carboxylate (5.2 g), methanol (25 mL), and tetrahydrofuran (25 mL) was added a 1 M aqueous sodium hydroxide solution (33 mL) at room temperature, followed by stirring at 60° C. for 2 hours. To the reaction mixture was added 1 M hydrochloric acid, followed by stirring at room temperature for 30 minutes, and then the precipitate was collected by filtration and washed with water to obtain rac-2-[(1R,2R,4S)-bicyclo[2.2.1]hept-2-ylamino]-4-(trifluoromethyl)pyrimidine-5-carboxylic acid (4.9 g) as a white powder.

Preparative Example 8

To a mixture of methyl 2-(2,4-dichlorobenzylamino)-4-(trifluoromethyl)pyrimidine-5-carboxylate (443 mg) and ethanol (7 mL) was added a solution of potassium hydroxide (200 mg) in ethanol (4 mL), and the mixture was stirred under heating with reflux for 5 hours. The reaction liquid was concentrated under reduced pressure, water (70 mL) was added to the residue, and the liquid property was made acidic (pH 1) with concentrated hydrochloric acid. The product was extracted with ethyl acetate (200 mL) twice, and then the organic layer was dried over anhydrous magnesium sulfate. The solvent was evaporated under reduced pressure to obtain 2-(2,4-dichlorobenzylamino)-4-(trifluoromethyl)pyrimidine-5-carboxylic acid (411 mg) as a colorless powder.

Preparative Example 9

A mixture of methyl 2-[(1-methylpiperidin-4-yl)amino]-4-(trifluoromethyl)pyrimidine-5-carboxylate (322 mg) and 6

M hydrochloric acid (3 mL) was stirred for 31.5 hours under heating with reflux. The reaction liquid was concentrated under reduced pressure, and the residue was solidified from a mixed solvent of diisopropyl ether and ethyl acetate, and then the obtained solid was washed with ethyl acetate to obtain 2-[(1-methylpiperidin-4-yl)-amino]-4-(trifluoromethyl)pyrimidine-5-carboxylic acid hydrochloride (297 mg) as a colorless powder.

Preparative Example 10

A mixture of 2-chloro-4-(trifluoromethyl)pyrimidine-5-carbonyl chloride (2.8 g) and dichloromethane (56 mL) was cooled in a dry ice-acetone bath, and morpholine (990 μL) and triethylamine (1.9 mL) were added dropwise thereto while keeping the temperature at −50° C. or lower. The reaction mixture was stirred at −70° C. for 2.5 hours, and then ethyl acetate and water were added thereto. The aqueous layer was extracted with ethyl acetate, and the organic layer was washed with water and saturated brine. After drying over anhydrous magnesium sulfate, the solvent was evaporated under reduced pressure and the obtained residue was purified by silica gel column chromatography (eluent: hexane-ethyl acetate) to obtain 4-{[2-chloro-4-(trifluoromethyl)pyrimidin-5-yl]carbonyl}morpholine (2.8 g) as a white solid.

Preparative Example 11

A mixture of rac-2-[(1R,2R,4S)-bicyclo[2.2.1]hept-2-ylamino]-4-(trifluoromethyl)pyrimidine-5-carboxylic acid (2.0 g), 4-methyl morpholine (1.1 mL) and 1,2-dimethoxyethane (40 mL) was cooled to −10° C., isobutyl chloroformate (1.1 mL) was added thereto, and the mixture was stirred at the same temperature for 1 hour. The insoluble materials in the reaction mixture were filtered and washed with 1,2-dimethoxyethane. The filtrate was cooled to −60° C. and a solution of sodium borohydride (377 mg) in water (4.0 mL) was added thereto, followed by stirring as it is for 1 hour. To the reaction mixture was added water, followed by extraction with ethyl acetate. The organic layer was washed with water and saturated brine, and dried over anhydrous magnesium sulfate. The solvent was evaporated under reduced pressure, and then the residue was purified by silica gel column chromatography (eluent: hexane-ethyl acetate=10:90 to 20:80) to obtain rac-{2-[(1R,2R,4S)-bicyclo[2.2.1]hept-2-ylamino]-4-(trifluoromethyl)pyrimidin-5-yl}methanol (1.05 g) as a colorless oily substance.

Preparative Example 12

To a mixture of rac-{2-[(1R,2R,4S)-bicyclo[2.2.1]hept-2-ylamino]-4-(trifluoromethyl)pyrimidin-5-yl}methanol (1.05 g) and dichloromethane (21 mL) was added thionyl chloride (0.8 mL) under ice-cooling, followed by stirring under ice-cooling for 30 minutes and at room temperature for 1 hour. To the reaction mixture was added a saturated aqueous sodium hydrogen carbonate solution under ice-cooling, followed by stirring for 10 minutes. The reaction mixture was extracted with chloroform and the obtained organic layer was dried over anhydrous magnesium sulfate. The solvent was evaporated to obtain rac-N-[(1R,2R,4S)-bicyclo[2.2.1]hept-2-yl]-5-(chloromethyl)-4-(trifluoromethyl)pyrimidin-2-amine (1.06 g) as a pale yellow solid.

Preparative Example 13

A mixture of 5-(chloromethyl)-N-(3-chlorophenyl)-4-(trifluoromethyl)pyrimidin-2-amine (544 mg), potassium phthalimide (626 mg), and N,N-dimethylformamide (5.44 mL) was stirred at room temperature for 20 hours. The reaction liquid was concentrated under reduced pressure, and then to the residue was added ethyl acetate (150 mL), followed by washing with water (50 mL) three times, and then with saturated brine (30 mL). The organic layer was dried over anhydrous magnesium sulfate, and then concentrated under reduced pressure to obtain crude 2-({2-[(3-chlorophenyl)amino]-4-(trifluoromethyl)pyrimidin-5-yl}methyl)-1H-isoindole-1,3(2H)-dione as a pale yellow powder.

Preparative Example 14

To the crude 2-({2-[(3-chlorophenyl)amino]-4-(trifluoromethyl)pyrimidin-5-yl}methyl)-1H-isoindole-1,3(2H)-dione obtained in Preparative Example 13 were added methanol (15 mL) and hydrazine monohydrate (0.125 mL) at room temperature, followed by stirring at 60° C. for 4.5 hours. The resulting precipitate was removed by filtration and the filtrate was concentrated, and then, the obtained residue was purified by silica gel column chromatography (eluent: chloroform-methanol) to obtain 5-(aminomethyl)-N-(3-chlorophenyl)-4-(trifluoromethyl)pyrimidin-2-amine (105 mg) as a pale yellow powder.

Preparative Example 15

To a mixture of tert-butyl{2-[(3-chlorophenyl)amino]-4-(trifluoromethyl)pyrimidin-5-yl}carbamate (267 mg) and 1,4-dioxane (3 mL) was added a 4 M hydrogen chloride-1,4-dioxane solution (3 mL), followed by stirring at room temperature for 4 hours. The reaction mixture was concentrated under reduced pressure, and to the obtained residue was added a saturated aqueous sodium hydrogen carbonate solution (20 mL), followed by extraction with ethyl acetate (50 mL). The extract was washed with saturated brine (20 mL), and the organic layer was dried over anhydrous magnesium sulfate, and then concentrated under reduced pressure. The obtained residue was purified by silica gel column chromatography (eluent: chloroform-methanol) to obtain $N^2$-(3-chlorophenyl)-4-(trifluoromethyl)pyrimidine-2,5-diamine (180 mg) as a yellow solid.

Preparative Example 16

To a solution of rac-(1R,2R,4S)-bicyclo[2.2.1]heptan-2-ol (1.12 g) in tetrahydrofuran (10 mL) was added 60% sodium hydride (400 mg) under ice-cooling, and the mixture was stirred at room temperature for 10 minutes. The reaction mixture was further stirred at an external temperature of 60° C. for 30 minutes, and then ice-cooled, and a mixture of methyl 2-chloro-4-(trifluoromethyl)pyrimidine-5-carboxylate (481 mg) and tetrahydrofuran (2 mL) was added thereto, followed by stirring at room temperature for 3 hours. To the reaction mixture were added water and saturated brine, followed by extraction with ethyl acetate. The obtained organic layer was washed with saturated brine and dried over anhydrous magnesium sulfate, and the solvent was evaporated under reduced pressure. The obtained residue was purified by silica gel column chromatography (eluent: hexane-ethyl acetate=100:0 to 97:3) to obtain a mixture (351 mg) of rac-(1R,2R,4S)-bicyclo[2.2.1]hept-2-yl2-[(1R,2R,4S)-bicyclo[2.2.1]hept-2-yloxy]-4-(trifluoromethyl)pyrimidine-5-carboxylate and rac-(1R,2R,4S)-bicyclo[2.2.1]hept-2-yl2-[(1S,2S,4R)-bicyclo[2.2.1]hept-2-yloxy]-4-(trifluoromethyl)pyrimidine-5-carboxylate as a colorless oily substance.

Preparative Example 17

To a solution of a mixture (110 mg) of rac-(1R,2R,4S)-bicyclo[2.2.1]hept-2-yl2-[(1R,2R,4S)-bicyclo[2.2.1]hept-2-yloxy]-4-(trifluoromethyl)pyrimidine-5-carboxylate and rac-(1R,2R,4S)-bicyclo[2.2.1]hept-2-yl2-[(1S,2S,4R)-bicyclo[2.2.1]hept-2-yloxy]-4-(trifluoromethyl)pyrimidine-5-carboxylate in ethanol (3 mL) was added a 1 M aqueous sodium hydroxide solution (1 mL) at room temperature, and the mixture was stirred at the same temperature for 1 hour. To the reaction mixture was added 1 M hydrochloric acid (1 mL), and then the solvent was evaporated under reduced pressure. To the residue was added water, followed by extraction with ethyl acetate. The extracted organic layer was washed with saturated brine and dried over anhydrous magnesium sulfate. The solvent was evaporated, and then the obtained residue was purified by silica gel column chromatography (eluent: chloroform-methanol=98:2 to 90:10) to obtain rac-2-[(1R,2R,4S)-bicyclo[2.2.1]hept-2-yloxy]-4-(trifluoromethyl)pyrimidine-5-carboxylic acid (109 mg) as a colorless solid.

Preparative Example 18

To a mixture of 4-one-ethyleneketal-1-adamantane carboxylic acid (2 g) and toluene (30 mL) were added triethylamine (1.35 mL) and diphenylphosphorylazide (2.0 mL) at room temperature, followed by stirring at the same temperature for 15 minutes. The reaction mixture was stirred at 90° C. for 20 minutes, and then benzyl alcohol (1.8 g) was added thereto, followed by heating with reflux for 5 hours. The mixture was cooled to room temperature, a saturated aqueous sodium hydrogen carbonate solution was added thereto, and the aqueous layer was extracted with ethyl acetate. The organic layer was washed with water and saturated brine, and dried over anhydrous magnesium sulfate, and then the solvent was evaporated under reduced pressure. The residue was purified by silica gel column chromatography (eluent: hexane-ethyl acetate) to obtain benzyl 4-one-ethyleneketal-1-adamantane carbamate (2.3 g) as a colorless oily substance.

Preparative Example 19

To a mixture of benzyl 4-one-ethyleneketal-1-adamantane carbamate (2.0 g) and methanol (20 mL) was added 10% palladium-carbon (50% wet, 350 mg) at room temperature, followed by stirring for 7 hours under a hydrogen atmosphere. The reaction mixture was filtered using Celite and washed with methanol. The solvent was evaporated under reduced pressure and the obtained residue was purified by silica gel column chromatography (eluent: chloroform-methanol-10% aqueous ammonia) to obtain 4-one-ethyleneketal-1-adamantane amine (1.15 g) as a colorless solid.

Preparative Example 20

To a mixture of 3,5-difluoro-7-hydroxy adamantane-1-carboxylic acid (1.04 g) and acetone (10 mL) were added triethylamine (1.25 mL) and ethyl chloroformate (860 µL) under ice-cooling, followed by stirring at the same temperature for 30 minutes. To the reaction mixture was added a solution of sodium azide (437 mg) in water (5 mL) under ice-cooling, followed by stirring at the same temperature for 80 minutes. To the reaction mixture was added water and the aqueous layer was extracted with ethyl acetate. The organic layer was washed with 1 M hydrochloric acid, water, and saturated brine in this order, and dried over anhydrous magnesium sulfate, and then the solvent was evaporated under reduced pressure. To the residue were added toluene (12 mL) and 1,4-dioxane (6 mL), followed by stirring at 85° C. for 15 minutes, and then benzyl alcohol (581 mg) and triethylamine (750 µL) were added thereto, followed by stirring at 95° C. for 4 hours. The mixture was cooled to room temperature, and then water was added thereto, and the aqueous layer was extracted with ethyl acetate. The organic layer was washed with 1 M hydrochloric acid, water, and saturated brine in this order, and dried over anhydrous magnesium sulfate, and then the solvent was evaporated under reduced pressure. The residue was purified by silica gel column chromatography (eluent: hexane-ethyl acetate) to obtain benzyl (3,5-difluoro-7-hydroxyadamantan-1-yl)carbamate (1.15 g) as a white powder.

Preparative Example 21

To a mixture of benzyl[rac-(1S,2S,4R)-1,4-dimethyl-7-oxabicyclo[2.2.1]hept-2-yl]carbamate (1.82 g) and ethanol (40 mL) was added 10% palladium-carbon (50% wet, 200 mg) at room temperature, followed by stirring under a hydrogen atmosphere for 4 hours. The reaction mixture was filtered using Celite and washed with ethanol, and then the filtrate was concentrated under reduced pressure. To the obtained residue were added ethyl acetate (50 mL) and a 4 M hydrogen chloride-1,4-dioxane solution (5 mL), followed by concentration under reduced pressure, and the obtained pale yellow solid was washed with ethyl acetate to obtain [rac-(1S,2S,4R)-1,4-dimethyl-7-oxabicyclo[2.2.1]heptan-2-amine hydrochloride (682 mg) as a colorless powder.

The compounds of Preparative Examples 22 to 80 shown in Tables below were prepared in the same manner as the methods of Preparative Examples 1 to 21. The structure, production process, and physicochemical data of each of Preparative Example Compounds are shown in Tables 4 to 16, respectively.

Example 1

To a mixture of rac-2-[(1R,2R,4S)-bicyclo[2.2.1]hept-2-ylamino]-4-(trifluoromethyl)pyrimidine-5-carboxylic acid (150 mg) and N,N-dimethyl formamide (3.0 mL) were added 1-(tetrahydro-2H-pyran-4-yl)methylamine (69 mg), 1-hydroxybenzotriazole (81 mg), and 1-ethyl-(3-dimethylaminopropyl)carbodiimide hydrochloride (115 mg) in this order at room temperature, and then the mixture was stirred at room temperature for 5 hours. To the reaction mixture was added water, followed by extraction with ethyl acetate. The organic layer was washed with water, a saturated aqueous sodium hydrogen carbonate solution, and saturated brine in this order, and then dried over anhydrous magnesium sulfate. The solvent was evaporated under reduced pressure and then the obtained residue was purified by silica gel column chromatography (eluent: hexane-ethyl acetate). The obtained colorless oily substance was solidified using ethanol-water to obtain rac-2-[(1R,2R,4S)-bicyclo[2.2.1]hept-2-ylamino]-N-(tetrahydro-2H-pyran-4-ylmethyl)-4-(trifluoromethyl)pyrimidine-5-carboxamide (173 mg) as a white solid.

Example 2

To a mixture of 2-(adamantan-1-ylamino)-4-(trifluoromethyl)pyrimidine-5-carboxylic acid (120 mg) and N,N-dimethyl formamide (2.4 mL) were added 4-(trifluoromethyl) piperidine hydrochloride (87 mg), 1-hydroxybenzotriazole (62 mg), 1-ethyl-(3-dimethylaminopropyl)carbodiimide hydrochloride (88 mg), and N,N-diisopropyl ethylamine (0.12 mL) in this order at room temperature, and then the mixture was stirred at room temperature for 16 hours. To the reaction mixture were added a saturated aqueous sodium hydrogen carbonate solution and water, and the aqueous layer was extracted with ethyl acetate. The organic layer was washed with water and saturated brine, and dried over anhydrous magnesium sulfate, and then the solvent was evaporated under reduced pressure. The obtained residue was purified by silica gel column chromatography (eluent: hexane-ethyl acetate), and the obtained white solid was first dissolved in a mixed solvent of hexane and ethyl acetate, and then solidified again to obtain N-adamantan-1-yl-4-(trifluoromethyl)-5-{[4-(trifluoromethyl)piperidin-1-yl]carbonyl}pyrimidin-2-amine (81 mg) as a white powder.

Example 3

A mixture of 4-{[2-chloro-4-(trifluoromethyl)pyrimidin-5-yl]carbonyl}morpholine (100 mg), (1R,2S,4R)-1,7,7-trimethylbicyclo[2.2.1]heptan-2-amine (207 mg), and 1,4-dioxane (2 mL) was stirred at room temperature for 3 hours. To the reaction mixture was added water and the aqueous layer was extracted with ethyl acetate. The organic layer was washed with water and saturated brine, and dried over anhydrous magnesium sulfate, and then the solvent was evaporated under reduced pressure. The residue was purified by silica gel column chromatography (eluent: hexane-ethyl acetate), and the obtained colorless oily substance was solidified from hexane-ethyl acetate to obtain 5-(morpholin-4-ylcarbonyl)-4-(trifluoromethyl)-N-[(1R,2S,4R)-1,7,7-trimethylbicyclo[2.2.1]hept-2-yl]pyrimidin-2-amine (98 mg) as a white solid.

Example 4

A mixture of 4-{[2-chloro-4-(trifluoromethyl)pyrimidin-5-yl]carbonyl}morpholine (150 mg), rac-(1S,2R,4R)-bicyclo[2.2.1]heptan-2-amine hydrochloride (300 mg), triethylamine (354 µL), and 1,4-dioxane (1.5 mL) was stirred at room temperature for 3 hours. To the reaction mixture was added water and the aqueous layer was extracted with ethyl acetate. The organic layer was washed with water and saturated brine, and dried over anhydrous magnesium sulfate, and then the solvent was evaporated under reduced pressure. The residue was purified by silica gel column chromatography (eluent: hexane-ethyl acetate), and the obtained colorless oil was solidified from hexane-ethyl acetate to obtain rac-N-[(1R,2S,4S)-bicyclo[2.2.1]hept-2-yl]-5-(morpholin-4-ylcarbonyl)-4-(trifluoromethyl)pyrimidin-2-amine (132 mg) as a white solid.

Example 5

To a mixture of 4-{[2-chloro-4-(trifluoromethyl)pyrimidin-5-yl]carbonyl}thiomorpholin-1,1-dioxide (130 mg), 1-amino-3-ethyl adamantane hydrochloride (245 mg), and N,N-dimethylformamide (3 mL) was added potassium carbonate (209 mg) at room temperature, followed by stirring at 80° C. for 3 hours. To the reaction mixture was added water and the aqueous layer was extracted with ethyl acetate. The organic layer was washed with saturated brine and dried over anhydrous magnesium sulfate, and then the solvent was evaporated under reduced pressure. The residue was purified by silica gel column chromatography (eluent: hexane-ethyl acetate), and the obtained residue was solidified from ethanol to obtain 5-[(1,1-dioxidothiomorpholin-4-yecarbonyl]-N-(3-ethyladamantan-1-yl)-4-(trifluoromethyl)pyrimidin-2-amine (154 mg) as a white solid.

Example 6

To a mixture of 4-{[2-chloro-4-(trifluoromethyl)pyrimidin-5-yl]carbonyl}thiomorpholin-1,1-dioxide (100 mg), 3-exo-hydroxymethylbicyclo[2.2.1]heptyl-2-exo-amine hydrochloride (129 mg), and 1,4-dioxane (3 mL) was added N,N-diisopropyl ethylamine (0.20 mL) at room temperature, and the mixture was stirred at 80° C. for 2 hours. To the reaction mixture was added water and the aqueous layer was extracted with ethyl acetate. The organic layer was washed with saturated brine and dried over anhydrous magnesium sulfate, and then the solvent was evaporated under reduced pressure. The obtained residue was purified by silica gel column chromatography (eluent: hexane-ethyl acetate) to obtain rac-[(1R,2S,3R,4S)-3-({5-[(1,1-dioxidothiomorpholin-4-yl)carbonyl]-4-(trifluoromethyl)pyrimidin-2-yl}amino)bicyclo[2.2.1]hept-2-yl]methanol (72 mg) as a white solid.

Example 7

A mixture of 4-{[2-chloro-4-(trifluoromethyl)pyrimidin-5-yl]carbonyl}morpholine (150 mg), 6-nitro-1,2,3,4-tetrahydroquinoline (136 mg), tris(dibenzylideneacetone)dipalladium(0) (14 mg), (R)-(+)-2,2'-bis(diphenylphosphino)-1,1'-binaphthyl (19 mg), sodium tert-butoxide (98 mg), and toluene (2 mL) was stirred at 110° C. for 30 minutes under radiation with microwave. To the reaction mixture was added water and the aqueous layer was extracted with ethyl acetate. The organic layer was washed with saturated brine and dried over anhydrous magnesium sulfate, and then the solvent was evaporated under reduced pressure. The residue was purified by silica gel column chromatography (eluent: hexane-ethyl acetate), and the obtained residue was solidified from a mixed solvent of hexane and ethyl acetate to obtain 1-[5-(morpholin-4-ylcarbonyl)-4-(trifluoromethyl)pyrimidin-2-yl]-6-nitro-1,2,3,4-tetrahydroquinoline (62 mg) as a yellow powder.

Example 8

A mixture of 4-{[2-chloro-4-(trifluoromethyl)pyrimidin-5-yl]carbonyl}morpholine (200 mg), methyl 1,2,3,4-tetrahydroquinoline-6-carboxylate (323 mg), tris(dibenzylideneacetone)dipalladium(0) (19 mg), (R)-(+)-2,2'-bis(diphenylphosphino)-1,1'-binaphthyl (25 mg), cesium carbonate (661 mg), and toluene (3 mL) was heated with reflux for 1 hour. To the reaction mixture was added water and the aqueous layer was extracted with ethyl acetate. The organic layer was washed with saturated brine and dried over anhydrous magnesium sulfate, and then the solvent was evaporated under reduced pressure. The obtained residue was purified by silica gel column chromatography (eluent: hexane-ethyl acetate) to obtain methyl 1-[5-(morpholin-4-ylcarbonyl)-4-(trifluoromethyl)pyrimidin-2-yl]-1,2,3,4-tetrahydroquinoline-6-carboxylate (170 mg) as a yellowish white solid.

Example 9

A mixture of 4-{[2-chloro-4-(trifluoromethyl)pyrimidin-5-yl]carbonyl}morpholine (150 mg), adamantan-2-amine hydrochloride (476 mg), triethylamine (0.50 mL), and N-methyl-2-pyrrolidone (3 mL) was stirred at 150° C. for 1 hour under radiation with microwave. To the reaction mixture was added water and the aqueous layer was extracted with ethyl acetate. The organic layer was washed with saturated brine and dried over anhydrous magnesium sulfate, and then the solvent was evaporated under reduced pressure. The obtained residue was purified by silica gel column chromatography (eluent: hexane-ethyl acetate) to obtain N-adamantan-2-yl-5-(morpholin-4-ylcarbonyl)-4-(trifluoromethyl)pyrimidin-2-yl-2-amine (200 mg) as a colorless solid.

Example 10

To a mixture of rac-N-[(1R,2R,4S)-bicyclo[2.2.1]hept-2-yl]-5-(chloromethyl)-4-(trifluoromethyl)pyrimidin-2-amine (200 mg) and N,N-dimethyl formamide (3 mL) was added morpholine (0.57 mL), and the mixture was stirred at room temperature for 15 hours. The solvent was evaporated under reduced pressure from the reaction mixture, and water was added to the residue, followed by extraction with ethyl acetate. The organic layer was washed with water and saturated brine, and dried over anhydrous magnesium sulfate, and then the solvent was evaporated under reduced pressure. The residue was purified by silica gel column chromatography (eluent: hexane-ethyl acetate). The obtained colorless oil was dissolved in 1,4-dioxane (5 mL), and a 4 M hydrogen chloride/1,4-dioxane solution (1 mL) was added thereto, followed by stirring at room temperature for 1 hour. The precipitated solid was collected by filtration and washed with 1,4-dioxane to obtain rac-N-[(1R,2R,4S)-bicyclo[2.2.1]hept-2-yl]-5-(morpholin-4-ylmethyl)-4-(trifluoromethyl)pyrimidin-2-amine hydrochloride (187 mg) as a white solid.

Example 11

To a mixture of N-adamantan-1-yl-5-(chloromethyl)-4-(trifluoromethyl)pyrimidin-2-amine (170 mg) and N,N-dimethyl formamide (4 mL) were added morpholine (0.21 mL) and potassium carbonate (136 mg) under ice-cooling, and the mixture was stirred at room temperature for 1.5 hours. To the reaction mixture was added water, and the aqueous layer was extracted with ethyl acetate. The organic layer was washed with water and saturated brine, and dried over anhydrous magnesium sulfate, and then the solvent was evaporated under reduced pressure. The obtained residue was purified by silica gel column chromatography (eluent: hexane-ethyl acetate) to obtain N-adamantan-1-yl-5-(morpholin-4-ylmethyl)-4-(trifluoromethyl)pyrimidin-2-amine (160 mg) as a white solid.

Example 12

To a mixture of 5-(aminomethyl)-N-(3-chlorophenyl)-4-(trifluoromethyl)pyrimidin-2-amine (103 mg) and dichloromethane (2 mL) were added tetrahydro-2H-pyran-4-carboxylic acid (53 mg), 1-hydroxybenzotriazole (69 mg), and 1-ethyl-(3-dimethylaminopropyl)carbodiimide hydrochloride (98 mg) in this order at room temperature, and the mixture was stirred at room temperature for 3 days. To the reaction mixture was added ethyl acetate (50 mL), the organic layer was washed with a saturated aqueous sodium hydrogen carbonate solution and saturated brine in this order, and then dried over anhydrous magnesium sulfate, and the solvent was evaporated under reduced pressure. The obtained residue was purified by silica gel column chromatography (eluent: chloroform-methanol), and the obtained product was solidified from a mixed solvent of ethanol and ethyl acetate to obtain N-({2-[(3-chlorophenyl)amino]-4-(trifluoromethyl)pyrimidin-5-yl}methyl)tetrahydro-2H-pyran-4-carboxamide (41 mg) as a colorless powder.

Example 13

To a mixture of tetrahydro-2H-pyran-4-ylacetic acid (89 mg), N,N-dimethyl formamide (1 μL), and dichloromethane (1 mL) was added oxalylchloride (54 μL), and the mixture was stirred at room temperature for 2 hours. The reaction liquid was concentrated under reduced pressure, and then toluene (1 mL) was added thereto, followed by further concentration under reduced pressure, to obtain crude tetrahydro-2H-pyran-4-yl acetyl chloride.

To a mixture of $N^2$-(3-chlorophenyl)-4-(trifluoromethyl)pyrimidine-2,5-diamine (147 mg), pyridine (62 μL), and dichloromethane (1 mL) was added a solution of the above crude tetrahydro-2H-pyran-4-ylacetyl chloride in dichloromethane (2 mL) under ice-cooling, followed by stirring at room temperature for 6 hours. To the reaction mixture was added ethyl acetate (50 mL), the organic layer was washed with a 10% aqueous citric acid solution, and then the solvent was evaporated under reduced pressure. The obtained residue was washed with warmed ethyl acetate to obtain N-{2-[(3-chlorophenyl)amino]-4-(trifluoromethyl)pyrimidin-5-yl}-2-(tetrahydro-2H-pyran-4-yl)acetamide (176 mg) as a colorless powder.

Example 14

To a mixture of $N^2$-(3-chlorophenyl)-4-(trifluoromethyl)pyrimidine-2,5-diamine (150 mg), pyridine (84 μL) and dichloromethane (3 mL) was added benzoyl chloride (72 μL) under ice-cooling, followed by stirring at room temperature for 3 hours. To the reaction mixture was added a saturated aqueous sodium hydrogen carbonate solution and the aqueous layer was extracted with ethyl acetate. The organic layer was washed with water and saturated brine, and dried over anhydrous magnesium sulfate, and then the solvent was evaporated under reduced pressure. The residue was purified by silica gel column chromatography (eluent: hexane-ethyl acetate), and the obtained residue was solidified from a mixed solvent of hexane and ethyl acetate to obtain N-{2-[(3-chlorophenyl)amino]-4-(trifluoromethyl)pyrimidin-5-yl}benzamide (166 mg) as a white powder.

Example 15

To a mixture of $N^2$-(3-chlorophenyl)-4-(trifluoromethyl)pyrimidine-2,5-diamine (150 mg), pyridine (84 μL) and dichloromethane (3 mL) was added benzenesulfonylchloride (129 mg) under ice-cooling, followed by stirring at room temperature for 6 hours. To the reaction mixture was added a saturated aqueous sodium hydrogen carbonate solution and the aqueous layer was extracted with ethyl acetate. The organic layer was washed with water and saturated brine, and dried over anhydrous magnesium sulfate, and then the solvent was evaporated under reduced pressure. The residue was purified by silica gel column chromatography (eluent: hexane-ethyl acetate), and the obtained residue was solidified from a mixed solvent of hexane and ethyl acetate to obtain N-{2-[(3-chlorophenyl)amino]-4-(trifluoromethyl)pyrimidin-5-yl}benzenesulfonamide (174 mg) as a white powder.

Example 16

To a mixture of 2-[(3-chlorophenyl)amino]-4-(trifluoromethyl)pyrimidine-5-carboxylic acid (307 mg), triethylamine (162 μL), and tert-butyl alcohol (9 mL) was added diphenylphosphorylazide (250 μL), followed by stirring at 90° C. for 7 hours. To the reaction mixture was added a saturated aqueous sodium hydrogen carbonate solution (50 mL), followed by extraction with ethyl acetate (50 mL), and then the extract was washed with saturated brine (30 mL). The organic layer was dried over anhydrous magnesium sulfate and then concentrated under reduced pressure, and the obtained residue was purified by silica gel column chromatography (eluent: hexane-ethyl acetate) to obtain tert-butyl {2-[(3-chlorophenyl)amino]-4-(trifluoromethyl)pyrimidin-5-yl}carbamate (270 mg) as a pale yellow powder.

Example 17

To a mixture of 2-[(3-chlorophenyl)amino]-4-(trifluoromethyl)pyrimidine-5-carboxylic acid (300 mg), triethylamine (197 μL), and toluene (6 mL) was added dropwise diphenyl phosphoric acid azide (265 μL), followed by stirring at room temperature for 30 minutes. Then, the mixture was stirred at 90° C. for 10 minutes, and a solution of tetrahydro-2H-pyran-4-yl methanol (131 mg) in toluene was added thereto, followed by heating with reflux for 2 hours. To the reaction mixture was added water and the aqueous layer was extracted with ethyl acetate. The organic layer was washed with water and saturated brine, then dried over anhydrous magnesium sulfate, filtered, and concentrated. The obtained residue was purified by silica gel column chromatography (eluent: hexane-ethyl acetate). The obtained pale yellow solid was washed with ethyl acetate-hexane to obtain tetrahydro-2H-pyran-4-ylmethyl {2-[(3-chlorophenyl)amino]-4-(trifluoromethyl)pyrimidin-5-yl}carboxamide (178 mg) as a white solid.

Example 18

To a mixture of 2-[(3-chlorophenyl)amino]-4-(trifluoromethyl)pyrimidine-5-carboxylic acid (300 mg), triethylamine (197 μL), and toluene (6 mL) was added dropwise diphenyl phosphoric acid azide (265 μL), followed by stirring at room temperature for 30 minutes. Then, the mixture was stirred at 90° C. for 10 minutes and a solution of tetrahydro-2H-pyran-4-amine (115 mg) in toluene was added thereto, followed by heating with reflux for 2 hours. The reaction mixture was left to be cool to room temperature, and the precipitated solid was filtered and washed with toluene. The obtained white solid was washed with ethanol to obtain 1-{2-[(3-chlorophenyl)amino]-4-(trifluoromethyl)pyrimidin-5-yl}-3-(tetrahydro-2H-pyran-4-yl)urea (138 mg) as a white solid.

Example 19

To a mixture of {2-[(3-chlorophenyl)amino]-4-(trifluoromethyl)pyrimidin-5-yl}methanol (200 mg), phenol (70 μL), triphenyl phosphine (190 mg) and dichloromethane (4 mL) was added diethyl azodicarboxylate (330 pt), and the mixture was stirred at room temperature overnight. The reaction mixture was concentrated and the obtained residue was purified by silica gel column chromatography (eluent: hexane-ethyl acetate). The obtained pale yellow solid was washed with ethanol-water to obtain N-(3-chlorophenyl)-5-(phenoxymethyl)-4-(trifluoromethyl)pyrimidin-2-amine (55 mg) as a white solid.

Example 20

To a mixture of 60% sodium hydride (26 mg) and N,N-dimethylformamide (4 mL) was added {2-[(3-chlorophenyl) amino]-4-(trifluoromethyl)pyrimidin-5-yl}methanol (200 mg), followed by stirring at room temperature for 30 minutes. Thereafter, bromomethyl cyclohexane (139 μL) was added thereto, followed by stirring at room temperature for 2 hours. 60% Sodium hydride (26 mg) and bromomethyl cyclohexane (139 μL) were added thereto again, followed by stirring at room temperature overnight. To the reaction mixture was added water and the aqueous layer was extracted with ethyl acetate. The organic layer was washed with water and saturated brine, then dried over anhydrous magnesium sulfate, filtered, and concentrated. The obtained residue was purified by silica gel column chromatography (eluent: hexane-ethyl acetate) to obtain N-(3-chlorophenyl)-5-[(cyclohexylmethoxy)methyl]-4-(trifluoromethyl)pyrimidin-2-amine (100 mg) as a white solid.

Example 21

To a solution of rac-2-[(1R,2R,4S)-bicyclo[2.2.1]hept-2-yloxy]-4-(trifluoromethyl)pyrimidine-5-carboxylic acid (55 mg) in N,N-dimethylformamide (5 mL) were added 1-ethyl-(3-dimethylaminopropyl)carbodiimide hydrochloride (70 mg) and 1-hydroxybenzotriazole (49 mg), followed by stirring at room temperature for 30 minutes. To the reaction mixture was added thiomorpholine 1,1-dioxide (49 mg), followed by stirring at room temperature for 15 hours. The reaction mixture was concentrated under reduced pressure, and to the obtained residue was added water, followed by extraction with ethyl acetate. The obtained organic layer was washed with saturated brine and dried over anhydrous magnesium sulfate, and then the solvent was evaporated under reduced pressure. The obtained residue was purified by silica gel column chromatography (eluent: chloroform-methanol=100:0 to 95:5). To the obtained residue was added ethanol (3 mL), followed by heating and dissolving, and then stirring at room temperature for 1 hour. The precipitated colorless solid was collected by filtration, washed with a small amount of ethanol, and then dried to obtain rac-4-({2-[(1R,2R,4S)-bicyclo[2.2.1]hept-2-yloxy]-4-(trifluoromethyl)pyrimidin-5-yl}carbonyl)thiomorpholine 1,1-dioxide (45 mg).

Example 22

To a solution of quinuclidin-3-ol (127 mg) in N,N-dimethylformamide (5 mL) was added 60% sodium hydride (60 mg), and the mixture was stirred at room temperature for 20 minutes. To the reaction mixture was added 4-{[2-chloro-4-(trifluoromethyl)pyrimidin-5-yl]carbonyl}thiomorpholine 1,1-dioxide (344 mg), followed by stirring at room temperature for 1 hour, and then at 80° C. for 3 hours. To the reaction mixture were added water and saturated brine, followed by stirring and then extracting with a mixed solvent of chloroform:2-propanol=3:1. The obtained organic layer was dried over anhydrous magnesium sulfate, and then the solvent was evaporated. The obtained residue was purified by silica gel column chromatography (eluent: chloroform:methanol:28% aqueous ammonia=10:1:0.1) to obtain a colorless oily substance (207 mg). This oily substance was dissolved in ethanol (5 mL) and then fumaric acid (58 mg) was added thereto, followed by stirring at an external temperature of 80° C. for 1 hour. The reaction mixture was cooled to room temperature under stirring, and further stirred at room temperature for 1 hour, and then the obtained colorless solid was collected by filtration, washed with ethanol, and dried to obtain 3-({5-[(1, 1-dioxidothiomorpholin-4-yl)carbonyl]-4-(trifluoromethyl) pyrimidin-2-yl}oxy)quinuclidine fumarate (138 mg).

Example 23

A mixture of 4-{[2-chloro-4-(trifluoromethyl)pyrimidin-5-yl]carbonyl}morpholine (170 mg), 2,4-dichlorophenol (112 mg), cesium carbonate (225 mg), and N,N-dimethyl formamide (2 mL) was stirred at room temperature for 15 hours, and then at 100° C. for 10 hours. To the reaction liquid was added ethyl acetate (30 mL), followed by washing with saturated brine (20 mL) and a saturated aqueous ammonium chloride solution (20 mL) in this order, the organic layer was dried over anhydrous magnesium sulfate, and then the solvent was evaporated under reduced pressure. The residue was purified by silica gel column chromatography (eluent: chloroform-ethyl acetate) to obtain 4-{[2-(2,4-dichlorophenoxy)-4-(trifluoromethyl)pyrimidin-5-yl]carbonyl}morpholine (36 mg) as a brown oily substance.

Example 24

A mixture of 4-{[2-chloro-4-(trifluoromethyl)pyrimidin-5-yl]carbonyl}morpholine (167 mg), 3-chlorobenzenethiol (98 mg), cesium carbonate (221 mg), and N,N-dimethyl formamide (2 mL) was stirred at room temperature for 15 hours, and then at 70° C. for 10 hours. To the reaction liquid was added ethyl acetate (30 mL), followed by washing with saturated brine (20 mL) and a saturated aqueous ammonium chloride solution (20 mL) in this order, the organic layer was dried over anhydrous magnesium sulfate, and then the solvent was evaporated under reduced pressure. The residue was purified by silica gel column chromatography (eluent: chloroform-ethyl acetate) to obtain 4-({2-[(3-chlorophenyl)sulfanyl]-4-(trifluoromethyl)pyrimidin-5-yl}carbonyl)morpholine (183 mg) as a colorless solid.

Example 25

To a mixture of methyl 1-[5-(morpholin-4-ylcarbonyl)-4-(trifluoromethyl)pyrimidin-2-yl]-1,2,3,4-tetrahydroquinoline-6-carboxylate (100 mg) and methanol (2 mL) was added a 1 M aqueous sodium hydroxide solution (670 µL) at room temperature, followed by stirring at 60° C. for 3 hours. To the reaction mixture were added 1 M hydrochloric acid and water, followed by stirring at room temperature for 30 minutes, and then the resulting precipitate was filtered and washed with water to obtain 1-[5-(morpholin-4-ylcarbonyl)-4-(trifluoromethyl)pyrimidin-2-yl]-1,2,3,4-tetrahydroquinoline-6-carboxylic acid (95 mg) as a white powder.

Example 26

To a mixture of 3-{[5-(morpholin-4-ylcarbonyl)-4-(trifluoromethyl)pyrimidin-2-yl]amino}adamantan-1-ol (150 mg) and dichloromethane (3 mL) was added diethylaminosulfur trifluoride (70 µL) under ice-cooling, followed by stirring at room temperature for 30 minutes. The reaction mixture was alkalified by adding a saturated aqueous sodium hydrogen carbonate solution, and the aqueous layer was extracted with ethyl acetate. The organic layer was washed with water and saturated brine, and dried over anhydrous magnesium sulfate. The solvent was evaporated under reduced pressure and the obtained residue was purified by silica gel column chromatography (eluent: hexane-ethyl acetate) to obtain N-(3-fluoroadamantan-1-yl)-5-(morpholin-4-ylcarbonyl)-4-(trifluoromethyl)pyrimidin-2-amine (115 mg) as a white solid.

Example 27

To a mixture of (3-exo)-8-benzyl-N-[5-(morpholin-4-ylcarbonyl)-4-(trifluoromethyl)pyrimidin-2-yl]-8-azabicyclo [3.2.1]octan-3-amine (340 mg) and ethanol (5 mL), water (0.5 mL) were added ammonium formate (135 mg) and 10% palladium-carbon (50% wet, 100 mg) at room temperature, followed by heating with reflux for 2 hours. The reaction mixture was filtered using Celite and washed with methanol. The solvent was evaporated under reduced pressure and the obtained residue was purified by silica gel column chromatography (eluent: chloroform-methanol-10% aqueous ammonia) to obtain (3-exo)-N-[5-(morpholin-4-ylcarbonyl)-4-(trifluoromethyl)pyrimidin-2-yl]-8-azabicyclo[3.2.1]octan-3-amine (270 mg) as a colorless solid.

Example 28

To a mixture of (3-exo)-N-[5-(morpholin-4-ylcarbonyl)-4-(trifluoromethyl)pyrimidin-2-yl]-8-azabicyclo[3.2.1]octan-3-amine (120 mg) and dichloromethane (3 mL) were added triethylamine (87 µl) and acetyl chloride (24 µL) under ice-cooling, followed by stirring at the same temperature for 2 hours. To the reaction mixture was added a saturated aqueous sodium hydrogen carbonate solution, and the aqueous layer was extracted with ethyl acetate. The organic layer was washed with water and saturated brine, and dried over anhydrous magnesium sulfate. The solvent was evaporated under reduced pressure, and the obtained residue was purified by silica gel column chromatography (eluent: chloroform-methanol) to obtain (3-exo)-8-acetyl-N-[5-(morpholin-4-ylcarbonyl)-4-(trifluoromethyl)pyrimidin-2-yl]-8-azabicyclo [3.2.1]octan-3-amine (90 mg) as a white solid.

Example 29

To a mixture of 5-(morpholin-4-ylcarbonyl)-N-5'H-spiro [1,3-dioxolane-2,2'-tricyclo[3.3.1.1$^{3,7}$]decan]-5'-yl-4-(trifluoromethyl)pyrimidin-2-amine (200 mg) and tetrahydrofuran (3 mL) was added 1 M hydrochloric acid (3 mL) at room temperature, followed by stirring at 60° C. for 4 hours. The reaction mixture was alkalified by adding a saturated aqueous sodium hydrogen carbonate solution, and the aqueous layer was extracted with ethyl acetate. The organic layer was washed with saturated brine and dried over anhydrous magnesium sulfate, then the solvent was evaporated under reduced pressure, and the obtained residue was purified by silica gel column chromatography (eluent: hexane-ethyl acetate) to obtain 5-{[5-(morpholin-4-ylcarbonyl)-4-(trifluoromethyl)pyrimidin-2-yl]amino}adamantan-2-one (100 mg) as a white solid.

Example 30

To a mixture of 5-{[5-(morpholin-4-ylcarbonyl)-4-(trifluoromethyl)pyrimidin-2-yl]amino}adamantan-2-one (50 mg) and dichloromethane (2 mL) was added diethylaminosulfur trifluoride (0.12 mL) at room temperature, followed by stirring at the same temperature for 4 hours. The reaction mixture was alkalified by adding a saturated aqueous sodium hydrogen carbonate solution, and the aqueous layer was extracted with ethyl acetate. The organic layer was washed with water and saturated brine, and dried over anhydrous magnesium sulfate. The solvent was evaporated under reduced pressure, and the obtained residue was purified by silica gel column chromatography (eluent: hexane-ethyl acetate) to obtain N-(4,4-difluoroadamantan-1-yl)-5-(morpholin-4-ylcarbonyl)-4-(trifluoromethyl)pyrimidin-2-amine (40 mg) as a white solid.

Example 31

To a mixture of ethyl 1-{[2-(adamantan-1-ylamino)-4-(trifluoromethyl)pyrimidin-5-yl]carbonyl}piperidine-4-carboxylate (220 mg), methanol (3 mL) and tetrahydrofuran (3 mL) was added a 1 M aqueous sodium hydroxide solution (1.37 mL) at room temperature, followed by stirring at 60° C. for 2 hours. To the reaction mixture were added 1 M hydrochloric acid and water, followed by stirring at room temperature for 30 minutes. The solvent was evaporated under reduced pressure, to the obtained residue was added water, followed by stirring for 30 minutes, and then the precipitate was collected by filtration and washed with water to obtain 1-{[2-(adamantan-1-ylamino)-4-(trifluoromethyl)pyrimidin-5-yl]carbonyl}piperidine-4-carboxylic acid (190 mg) as a white powder.

Example 32

To a mixture of 1-{[2-(adamantan-1-ylamino)-4-(trifluoromethyl)pyrimidin-5-yl]carbonyl}piperidine-4-carboxylic acid (100 mg) and N,N-dimethyl formamide (2 mL) were added 2-(1H-benzotriazol-1-yl)-1,1,3,3-tetramethyluronium hexafluorophosphate (HBTU) (84 mg) and N,N-diisopropyl ethylamine (77 µL) at room temperature, followed by stirring at the same temperature for 1.5 hours. To the reaction mixture was added 28% aqueous ammonia (2 mL) at room temperature, followed by stirring at the same temperature for 3 hours. To the reaction mixture was added water and the aqueous layer was extracted with ethyl acetate. The organic layer was washed with saturated brine and dried over anhydrous magnesium sulfate, and then the solvent was evaporated under reduced pressure. The obtained residue was purified by silica gel column chromatography (eluent: chloroform-methanol), and the obtained crude product was solidified from a mixed solvent of ethanol and water to obtain 1-{[2-(adamantan-1-ylamino)-4-(trifluoromethyl)pyrimidin-5-yl]carbonyl}piperidine-4-carboxamide (68 mg) as a white powder.

Example 33

To a mixture of methyl 3-({5-[(1,1-dioxidothiomorpholin-4-yl)carbonyl]-4-(trifluoromethyl)pyrimidin-2-yl}amino)adamantane-1-carboxylate (500 mg) and methanol (2 mL), and tetrahydrofuran (2 mL) was added a 1 M aqueous sodium hydroxide solution (1.9 mL) at room temperature, followed by stirring at 60° C. for 3 hours. The solvent was evaporated under reduced pressure, and to the obtained residue were added water and 1 M hydrochloric acid, followed by stirring at room temperature for 30 minutes. The obtained precipitate was filtered and washed with water to obtain 3-({5-[(1,1-dioxidothiomorpholin-4-yl)carbonyl]-4-(trifluoromethyl)pyrimidin-2-yl}amino)adamantane-1-carboxylic acid (446 mg) as a white powder.

Example 34

To a mixture of 3-({5-[(1,1-dioxidothiomorpholin-4-yl)carbonyl]-4-(trifluoromethyl)pyrimidin-2-yl}amino)adamantane-1-carboxylic acid (120 mg) and N,N-dimethyl formamide (3 mL) was added 1,1'-carbonyldiimidazole (97 mg) at room temperature, followed by stirring at the same temperature for 30 minutes. To the reaction mixture was added 28% aqueous ammonia (3 mL) at room temperature, followed by stirring at the same temperature for 30 minutes. To the reaction mixture was added water, followed by stirring at room temperature for 30 minutes, and then the resulting precipitate was filtered and washed with water to obtain 3-({5-[(1,1-dioxidothiomorpholin-4-yl)carbonyl]-4-(trifluoromethyl)pyrimidin-2-yl}amino)adamantane-1-carboxamide (100 mg) as a white powder.

Example 35

To a mixture of 4-{[2-chloro-4-(trifluoromethyl)pyrimidin-5-yl]carbonyl}thiomorpholine 1,1-dioxide (500 mg), dichlorobis(triphenylphosphine)nickel (II) (190 mg), tetrahydrofuran (10 mL) was added a 0.5 M chloro(3-chlorobenzyl)zinc tetrahydrofuran solution (3.2 mL), followed by stirring at room temperature for 6 hours. To the reaction mixture was added water and the aqueous layer was extracted with ethyl acetate. The organic layer was washed with water and saturated brine, then dried over anhydrous magnesium sulfate, filtered, and concentrated. The obtained residue was purified by silica gel column chromatography (eluent: hexane-ethyl acetate). To the obtained pale yellow solid were added 1,4-dioxane (10 mL) and 1-methylpiperazine (0.16 mL), followed by stirring at room temperature for 6 hours. To the reaction mixture was added water and the aqueous layer was extracted with ethyl acetate. The organic layer was washed with water and saturated brine, then dried over anhydrous magnesium sulfate, filtered, and concentrated. The obtained residue was purified by silica gel column chromatography (eluent: hexane-ethyl acetate). The obtained white solid was washed with ethanol to obtain 4-{[2-(3-chlorobenzyl)-4-(trifluoromethyl)pyrimidin-5-yl]carbonyl}thiomorpholine 1,1-dioxide (212 mg) as a white solid.

The compounds of Examples 36 to 170 shown in Tables below were prepared in the same manner as the methods of Examples 1 to 35. The structure of each of Example Compounds are shown in Tables 17 to 28, and the production process and physicochemical data of each of Example Compounds are shown in Tables 29 to 49. In addition, Example compounds 3, 79, 80, 83, 84, 95, 96, 104, 105, 106, 112, 113, 130, 131, 132, 133, 138, 140, and 141 are optical active products.

Example C001

A solution of 4-{[2-chloro-4-(trifluoromethyl)pyrimidin-5-yl]carbonyl}thiomorpholine 1,1-dioxide (2062 mg) and N,N-diisopropylethylamine (3.5 mL) in 1,4-dioxane (200 mL) was prepared. To cyclopropyl amine (60 µL) was added the solution (1 mL) prepared above, followed by stirring at 80° C. for 3 hours. The reaction mixture was left to cool to room temperature, and PS-Trisamine (Biotage) (50 mg) and PS-NCO (Biotage) (50 mg) were added thereto, followed by stirring at room temperature overnight. The insoluble materials were filtered and the filtrate was concentrated. The residue was collected and purified by HPLC (eluent: 0.1% aqueous formate solution-methanol) and concentrated to obtain N-cyclopropyl-5-[(1,1-dioxidothiomorpholin-4-yl)carbonyl]-4-(trifluoromethyl)pyrimidin-2-amine (11 mg).

Here, the conditions for HPLC carried out to determine RT are shown below.

Column: ACQUITY HPLC HSS T3 C18 (Waters) (particle diameter: 1.8 µm, internal diameter: 2.1 mm, length: 50 mm)

Mobile phase: A Solution 0.1% aqueous formate solution, B Solution methanol

Flow rate: 0.7 mL/min; Detection wavelength: 254 nm; Column temperature: 40° C.; Injection amount: 1 µL

TABLE 3

| Time (min) | A sol (%) | B sol (%) | Elution |
|---|---|---|---|
| 0-3 | 95→10 | 5→90 | Gradient |
| 3-4 | 10 | 90 | Isocratic |

The compounds of Examples C002 to C334 shown in Tables below were prepared in the same manner as the method of Example C001. The structure of each of Example Compounds are shown in Tables 50 to 64 and the physicochemical data of each of Example Compounds are shown in Tables 65 to 68.

TABLE 4

| PEx | PSyn | Str | DAT |
|---|---|---|---|
| 1 | 1 | [structure] | NMR2: 1.18 (3H, s), 1.22 (9H, s), 3.69 (3H, s), 7.36 (1H, s) |
| 2 | 2 | [structure] | ESI+: 295 [M + Na] |
| 3 | 3 | [structure] | ESI+: 326 [M + Na] |
| 4 | 4 | [structure] | ESI+: 326 [M + Na] |
| 5 | 5 | [structure] | ESI+: 338 [M + Na] |
| 6 | 6 | [structure] | ESI+: 380 |

TABLE 4-continued

| PEx | PSyn | Str | DAT |
|---|---|---|---|
| 7 | 7 | | ESI+: 324 [M + Na] |

TABLE 5

| PEx | PSyn | Str | DAT |
|---|---|---|---|
| 8 | 8 | | ESI−: 364 |
| 9 | 9 | | ESI−: 303 |
| 10 | 10 | | ESI+: 318 [M + Na] |
| 11 | 11 | | ESI−: 286 |
| 12 | 12 | | NMR1: 1.04-1.21 (3H, m), 1.38-1.56 (4H, m), 1.60-1.70 (1H, m), 2.14-2.18 (1H, m), 2.19-2.24 (1H, m), 3.58-3.72 (1H, m), 4.75 (2H, s), 8.02-8.12 (1H, m), 8.60-8.70 (1H, m) |

TABLE 5-continued

| PEx | PSyn | Str | DAT |
|---|---|---|---|
| 13 | 13 | | ESI+: 455 [M + Na] |

TABLE 6

| PEx | PSyn | Str | DAT |
|---|---|---|---|
| 14 | 14 | | ESI+: 303 |
| 15 | 15 | | ESI−: 287 |
| 16 | 16 | | NMR1: 1.08-1.24 (6H, m), 1.38-1.60 (8H, m), 1.75-1.88 (2H, m), 2.28-2.33 (2H, m), 2.35-2.39 (1H, m), 2.43-2.48 (1H, m), 4.80 (1H, d, J = 6.8 Hz), 4.89 (1H, d, J = 6.6 Hz), 9.17 (1H, s) |
| 17 | 17 | | ESI+: 325 [M + Na] |

TABLE 6-continued
| PEx | PSyn | Str | DAT |
|---|---|---|---|
| 18 | 18 | 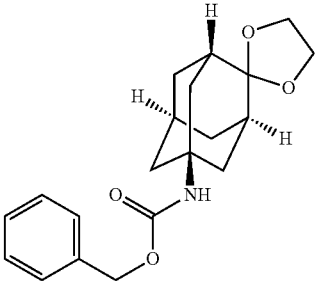 [SMILES: O=C(N[C@]12C[C@@H]3C[C@H](C1)C1(OCCO1)[C@@H](C3)C2)OCc1ccccc1] | ESI+: 366 [M + Na] |
| 19 | 19 | 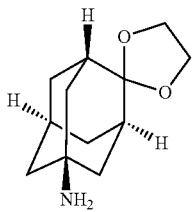 | ESI+: 210 |
TABLE 7
| PEx | PSyn | Str | DAT |
|---|---|---|---|
| 20 | 20 | 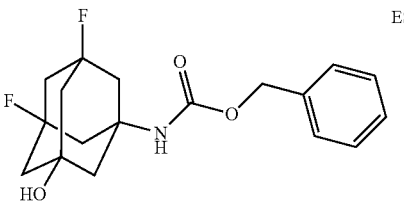 | ESI+: 360 [M + Na] |
| 21 | 21 | 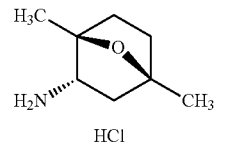 | ESI+: 142 |
| 22 | 1 | 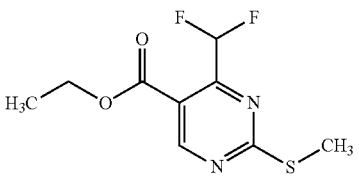 [SMILES: CCOC(=O)c1cnc(SC)nc1C(F)F] | NMR2: 1.34 (3H, t, J = 7 Hz), 2.62 (3H, s), 3.32 (3H, s), 4.36 (2H, q, J = 7 Hz), 7.42 (1H, t, J = 53.4 Hz), 9.15 (1H, s) |
| 23 | 2 | 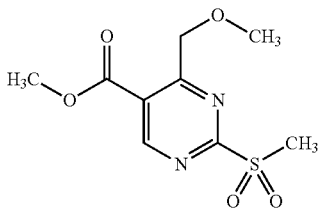 | ESI+: 283 [M + Na] |

TABLE 7-continued

| PEx | PSyn | Str | DAT |
|---|---|---|---|
| 24 | 2 | | NMR2: 1.47 (3H, t, J = 7.2 Hz), 3.45 (3H, s), 4.54 (2H, q, J = 7.2 Hz), 7.38 (1H, t, J = 53.4 Hz), 9.51 (1H, s) |
| 25 | 2 | | ESI+: 295 [M + Na] |
| 26 | 2 | | ESI+: 279 [M + Na] |

TABLE 8

| PEx | PSyn | Str | DAT |
|---|---|---|---|
| 27 | 3 | | ESI+: 360 [M + H], 382 [M + Na] |
| 28 | 3 | | ESI+: 310 [M + Na] |
| 29 | 3 | | ESI+: 366 [M + Na] |
| 30 | 3 | | ESI−: 302 |

TABLE 8-continued
| PEx | PSyn | Str | DAT |
|---|---|---|---|
| 31 | 3 | 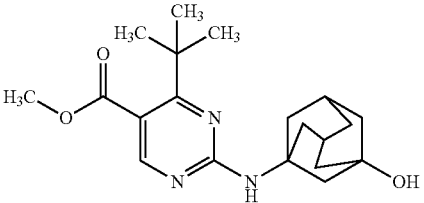 [SMILES: COC(=O)c1cnc(NC23CC4CC(CC(O)(C4)C2)C3)nc1C(C)(C)C] | ESI+: 360 |
| 32 | 3 | 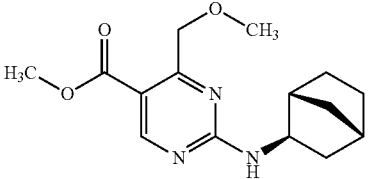 [SMILES: COCc1nc(N[C@@H]2C[C@H]3CC[C@@H]2C3)ncc1C(=O)OC] | ESI+: 314 [M + Na] |
| 33 | 3 | 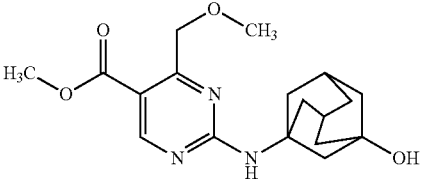 [SMILES: COCc1nc(NC23CC4CC(CC(O)(C4)C2)C3)ncc1C(=O)OC] | ESI+: 370 [M + Na] |
TABLE 9
| PEx | PSyn | Str | DAT |
|---|---|---|---|
| 34 | 3 | 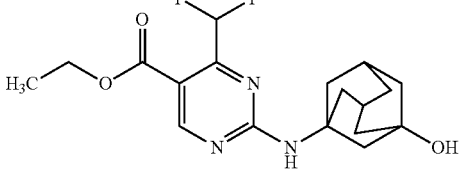 | ESI+: 390 [M + Na] |
| 35 | 4 | 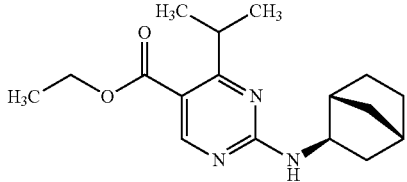 [SMILES: CCOC(=O)c1cnc(N[C@@H]2C[C@H]3CC[C@@H]2C3)nc1C(C)C] | ESI+: 326 [M + Na] |
| 36 | 5 | 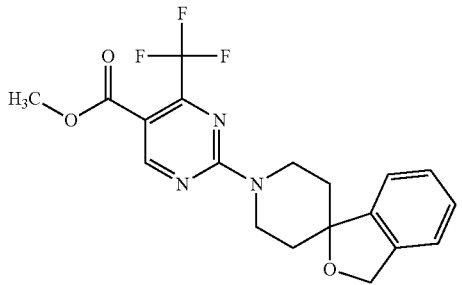 [SMILES: COC(=O)c1cnc(N2CCC3(CC2)OCc2ccccc23)nc1C(F)(F)F] | ESI+: 416 [M + Na] |

TABLE 9-continued
| PEx | PSyn | Str | DAT |
|---|---|---|---|
| 37 | 5 | 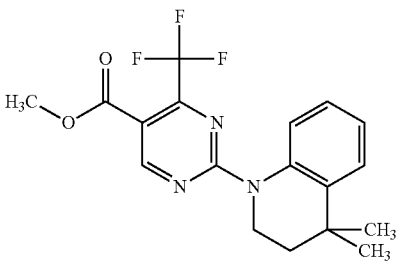 | ESI+: 388 [M + Na] |
| 38 | 5 | 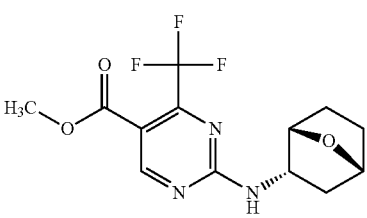 [SMILES: COC(=O)c1cnc(N[C@H]2C[C@H]3CC[C@@H]2O3)nc1C(F)(F)F] | ESI+: 340 [M + Na] |
| 39 | 5 | 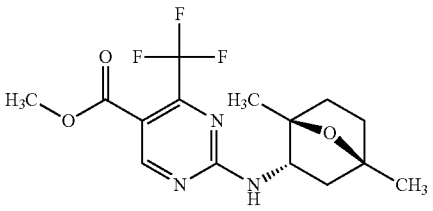 | ESI+: 368 [M + Na] |
TABLE 10
| PEx | PSyn | Str | DAT |
|---|---|---|---|
| 40 | 5 | 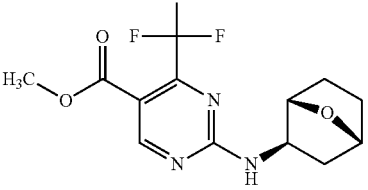 | ESI+: 340 [M + Na] |
| 41 | 5 | 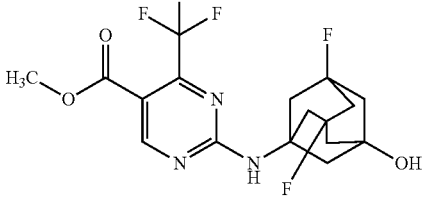 | ESI−: 406 |
| 42 | 5 | 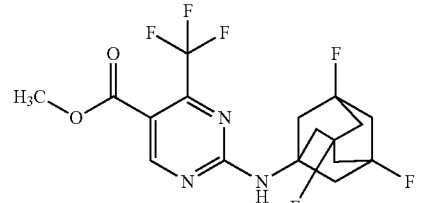 | ESI+: 432 [M + Na] |

TABLE 10-continued

| PEx | PSyn | Str | DAT |
|---|---|---|---|
| 43 | 6 | methyl 2-((tetrahydro-2H-pyran-4-yl)amino)-4-(trifluoromethyl)pyrimidine-5-carboxylate | ESI+: 328 [M + Na] |
| 44 | 6 | methyl 2-((1-methylpiperidin-4-yl)amino)-4-(trifluoromethyl)pyrimidine-5-carboxylate | ESI+: 319 |
| 45 | 6 | methyl 2-(3,4-dihydroquinolin-1(2H)-yl)-4-(trifluoromethyl)pyrimidine-5-carboxylate | ESI+: 360 [M + Na] |

TABLE 11

| PEx | PSyn | Str | DAT |
|---|---|---|---|
| 46 | 6 | methyl 2-(3,4-dihydroisoquinolin-2(1H)-yl)-4-(trifluoromethyl)pyrimidine-5-carboxylate | ESI+: 360 [M + Na] |
| 47 | 6 | methyl 2-(adamantan-2-ylamino)-4-(trifluoromethyl)pyrimidine-5-carboxylate | ESI+: 378 [M + Na] |
| 48 | 6 | methyl 2-((3-hydroxyadamantan-1-yl)amino)-4-(trifluoromethyl)pyrimidine-5-carboxylate | ESI+: 394 [M + Na] |

TABLE 11-continued

| PEx | PSyn | Str | DAT |
|---|---|---|---|
| 49 | 7 | | ESI+: 342 |
| 50 | 7 | | ESI+: 380 [M + Na] |
| 51 | 7 | | ESI−: 378 |

TABLE 12

| PEx | PSyn | Str | DAT |
|---|---|---|---|
| 52 | 7 | | ESI−: 350 |
| 53 | 7 | | ESI−: 302 |
| 54 | 7 | | ESI−: 330 |
| 55 | 7 | | ESI−: 302 |
| 56 | 7 | | ESI+: 332 |
| 57 | 7 | | ESI+: 276 |

TABLE 12-continued

| PEx | PSyn | Str | DAT |
|---|---|---|---|
| 58 | 7 | 4-cyclopropyl-2-(bicyclo[2.2.1]heptan-2-ylamino)pyrimidine-5-carboxylic acid | ESI+: 274 |

TABLE 13

| PEx | PSyn | Str | DAT |
|---|---|---|---|
| 59 | 7 | 4-cyclopropyl-2-((hydroxyadamantyl)amino)pyrimidine-5-carboxylic acid | ESI+: 330 |
| 60 | 7 | 4-tert-butyl-2-(bicyclo[2.2.1]heptan-2-ylamino)pyrimidine-5-carboxylic acid | ESI−: 288 |
| 61 | 7 | 4-tert-butyl-2-((hydroxyadamantyl)amino)pyrimidine-5-carboxylic acid | ESI+: 346 |
| 62 | 7 | 4-(methoxymethyl)-2-(bicyclo[2.2.1]heptan-2-ylamino)pyrimidine-5-carboxylic acid | ESI+: 300 [M + Na] |
| 63 | 7 | 4-(methoxymethyl)-2-((hydroxyadamantyl)amino)pyrimidine-5-carboxylic acid | ESI−: 332 |
| 64 | 7 | 4-(difluoromethyl)-2-((hydroxyadamantyl)amino)pyrimidine-5-carboxylic acid | ESI−: 338 |

TABLE 13-continued

| PEx | PSyn | Str | DAT |
|---|---|---|---|
| 65 | 7 | (4-isopropyl-2-(bicyclo[2.2.1]heptan-2-ylamino)pyrimidine-5-carboxylic acid) | ESI+: 276 |

TABLE 14

| PEx | PSyn | Str | DAT |
|---|---|---|---|
| 66 | 7 | (4-(trifluoromethyl)-2-((difluorohydroxyadamantyl)amino)pyrimidine-5-carboxylic acid) | ESI+: 416 [M + Na] |
| 67 | 7 | (4-(trifluoromethyl)-2-((difluoroadamantyl)amino)pyrimidine-5-carboxylic acid) | ESI+: 418 [M + Na] |
| 68 | 7 | (4-isopropyl-2-(bicyclo[2.2.1]heptan-2-ylamino)pyrimidine-5-carboxylic acid) | ESI+: 276 |
| 69 | 8 | (4-(trifluoromethyl)-2-((tetrahydropyran-4-yl)amino)pyrimidine-5-carboxylic acid) | ESI−: 290 |
| 70 | 8 | (4-(trifluoromethyl)-2-(3,4-dihydroquinolin-1(2H)-yl)pyrimidine-5-carboxylic acid) | ESI−: 322 |

TABLE 14-continued
| PEx | PSyn | Str | DAT |
|---|---|---|---|
| 71 | 8 | 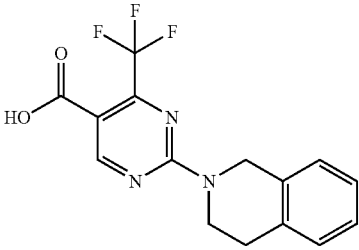 [SMILES: O=C(O)c1cnc(N2CCc3ccccc3C2)nc1C(F)(F)F] | ESI−: 322 |
TABLE 15
| PEx | PSyn | Str | DAT |
|---|---|---|---|
| 72 | 10 | 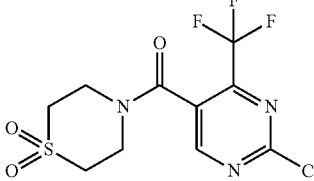 | ESI+: 366 [M + Na] |
| 73 | 11 | 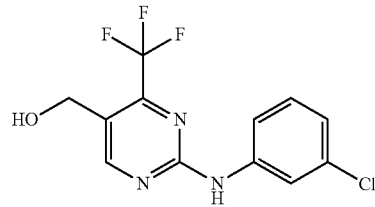 [SMILES: OCc1cnc(Nc2cccc(Cl)c2)nc1C(F)(F)F] | ESI−: 302 |
| 74 | 11 | 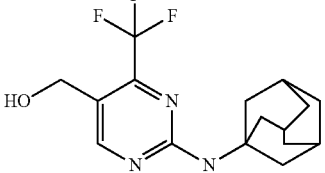 | ESI−: 326 |
| 75 | 11 | 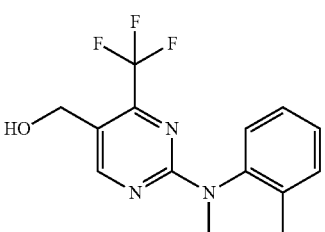 | ESI+: 310 |
| 76 | 12 | 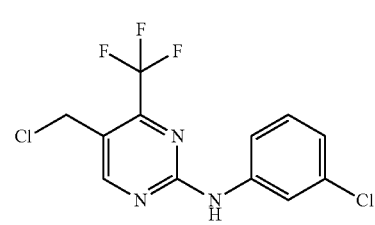 [SMILES: FC(F)(F)c1nc(Nc2cccc(Cl)c2)ncc1CCl] | ESI−: 320, 322 |

TABLE 15-continued

| PEx | PSyn | Str | DAT |
|---|---|---|---|
| 77 | 12 | (structure) | NMR1: 1.62-1.66 (6H, m), 2.03-2.08 (9H, m), 4.74 (2H, s), 7.69 (1H, s), 8.62 (1H, s) |

TABLE 16

| PEx | PSyn | Str | DAT |
|---|---|---|---|
| 78 | 12 | (structure) | NMR1: 1.91-1.99 (2H, m), 2.76 (2H, t, J = 6.6 Hz), 3.99 (2H, t, J = 6.3 Hz), 4.81-4.85 (2H, m), 7.02-7.09 (1H, m), 7.11-7.22 (2H, m), 7.68-7.73 (1H, m), 8.84 (1H, s) |
| 79 | 19 | (structure) | ESI+: 204 |
| 80 | 20 | (structure) | ESI+: 298 [M + Na] |

TABLE 17

| Ex | Str |
|---|---|
| 1 | (structure) |
| 2 | (structure) |
| 3 | (structure) Chiral |
| 4 | (structure) |

TABLE 17-continued
| Ex | Str |
|---|---|
| 5 | 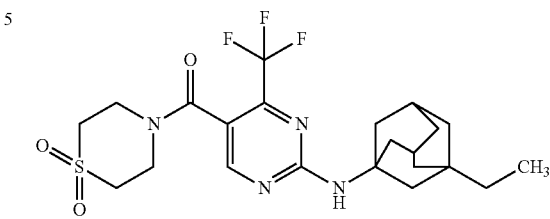 |
| 6 | 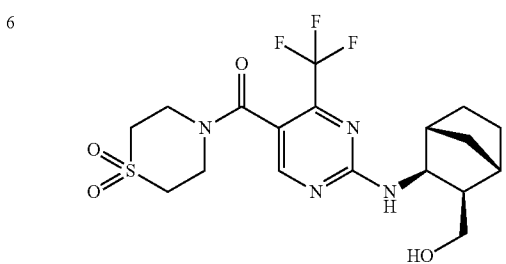 |
| 7 | 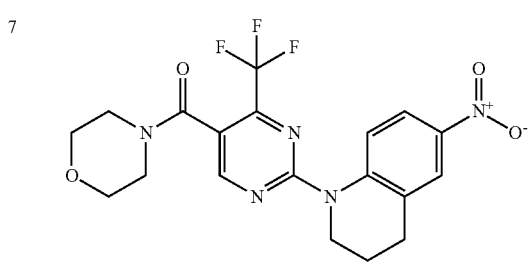 |
| 8 | 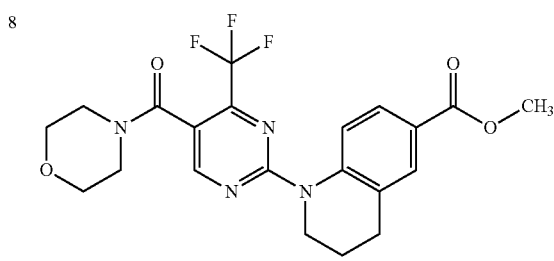 |
| 9 | 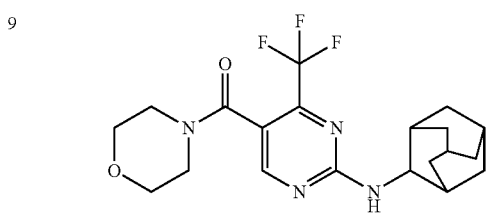 |
| 10 | 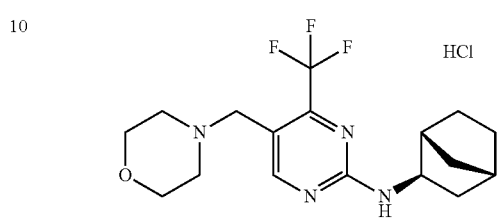 |
TABLE 17-continued
| Ex | Str |
|---|---|
| 11 | 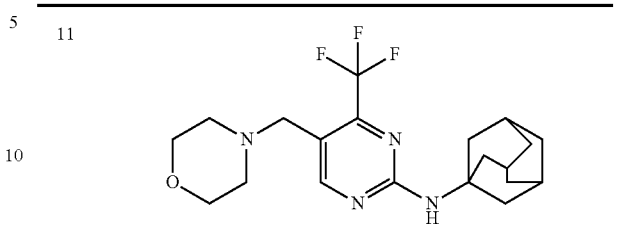 |
| 12 | 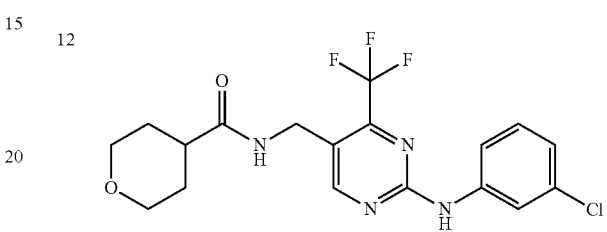 |
| 13 | 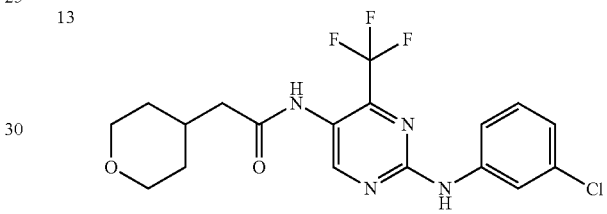 |
| 14 | 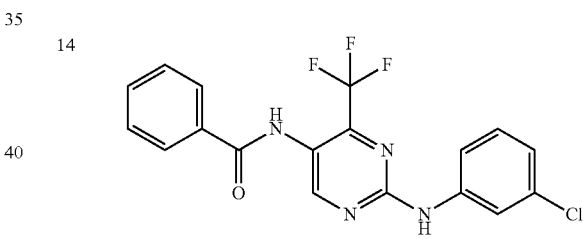 |
TABLE 18
| Ex | Str |
|---|---|
| 15 | 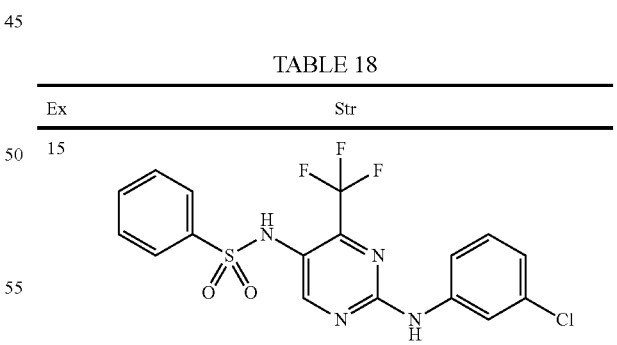 |
| 16 | 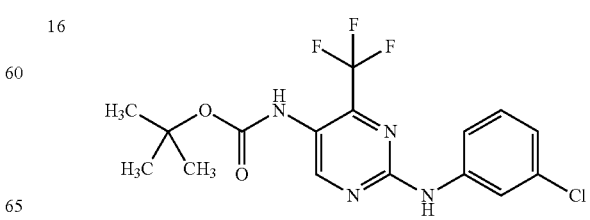 |

TABLE 18-continued
| Ex | Str |
|---|---|
| 17 | 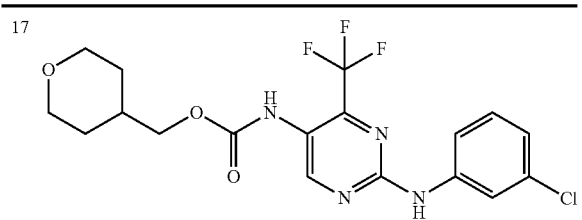 |
| 18 | 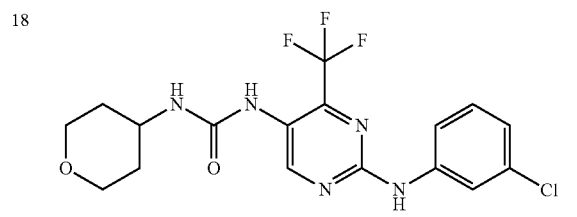 |
| 19 | 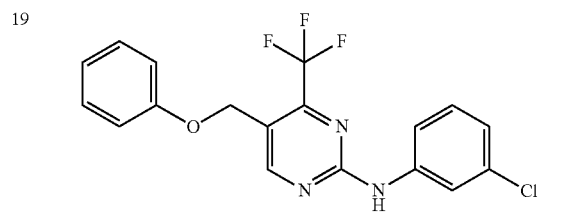 |
| 20 | 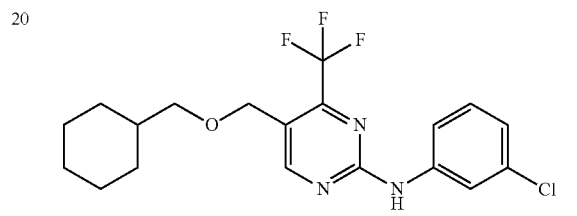 |
| 21 | 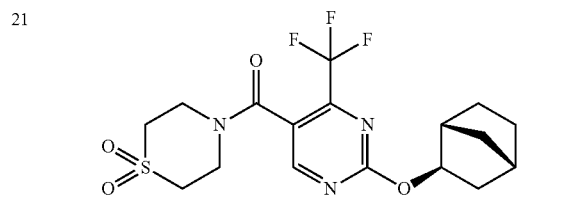 |
| 22 | 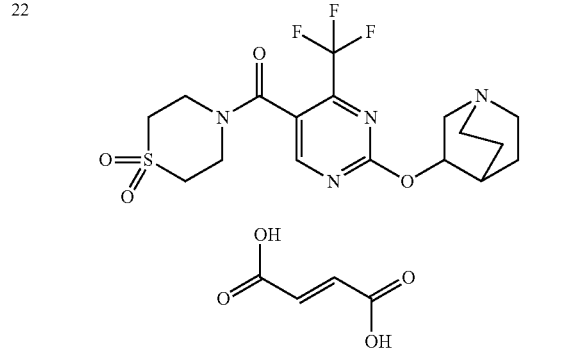 |
TABLE 18-continued
| Ex | Str |
|---|---|
| 23 | 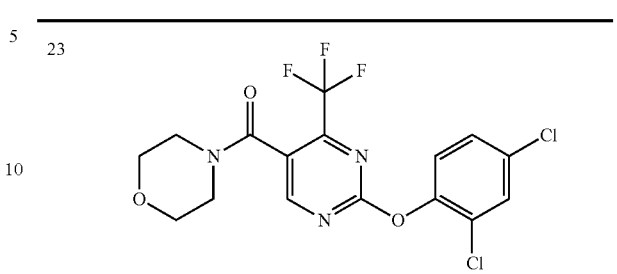 |
| 24 | 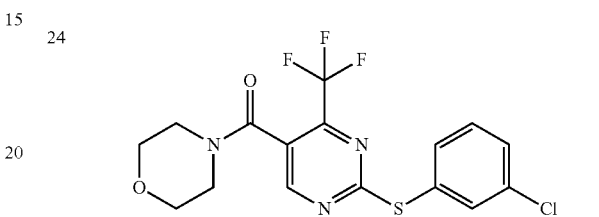 |
| 25 | 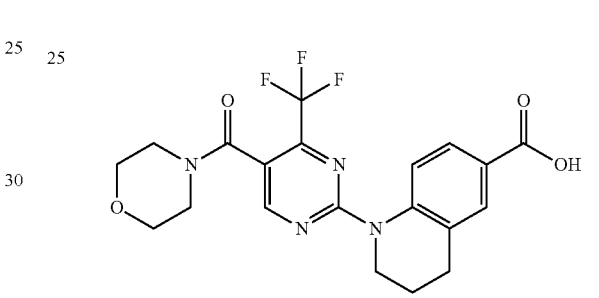 |
| 26 | 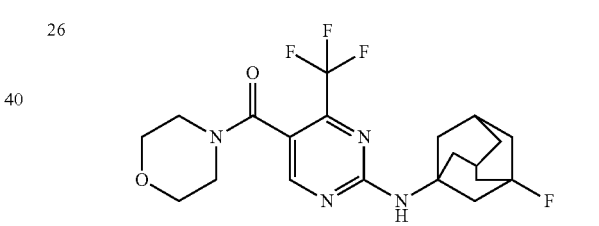 |
| 27 | 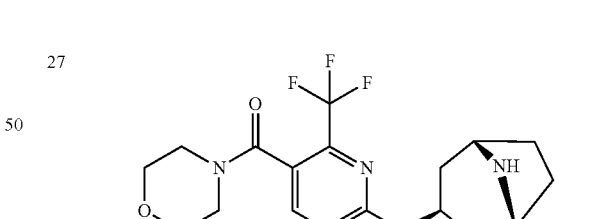 |
| 28 | 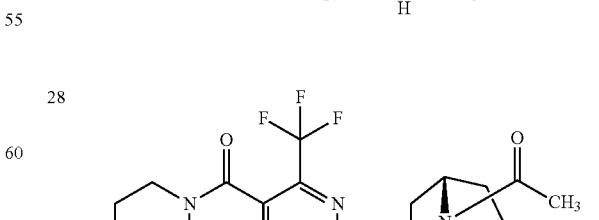 |

TABLE 19

| Ex | Str |
|---|---|
| 29 | (structure) |
| 30 | (structure) |
| 31 | (structure) |
| 32 | (structure) |
| 33 | (structure) |
| 34 | (structure) |

TABLE 19-continued

| Ex | Str |
|---|---|
| 35 | (structure) |
| 36 | (structure) |
| 37 | (structure) |
| 38 | (structure) |
| 39 | (structure) |
| 40 | (structure) |

TABLE 19-continued
| Ex | Str |
|---|---|
| 41 | 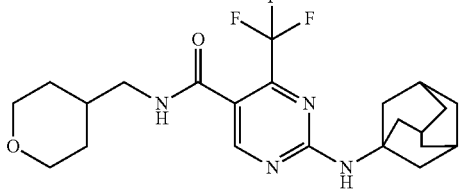 |
| 42 | 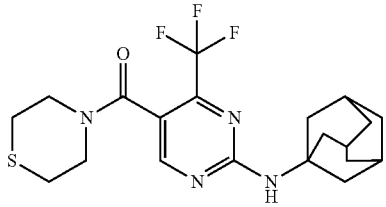 [SMILES: O=C(c1cnc(NC23CC4CC(CC(C4)C2)C3)nc1C(F)(F)F)N1CCSCC1] |
TABLE 20
| Ex | Str |
|---|---|
| 43 | 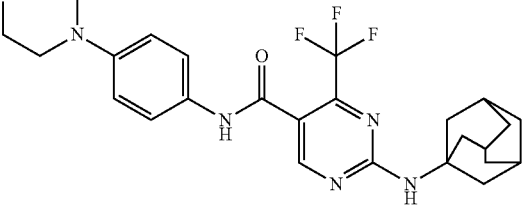 |
| 44 | 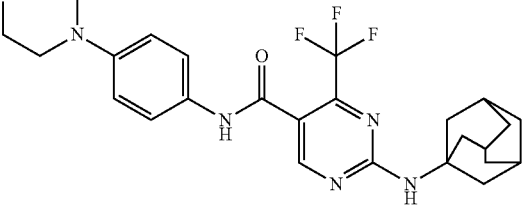 |
| 45 | 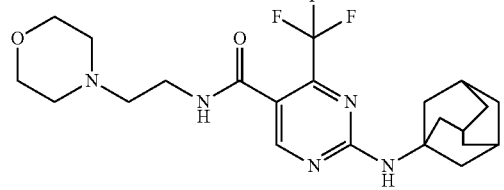 |
| 46 | 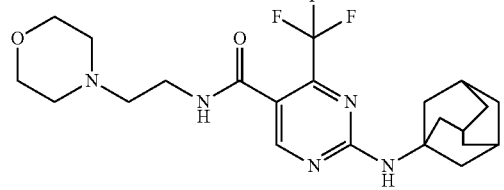 |
TABLE 20-continued
| Ex | Str |
|---|---|
| 47 | 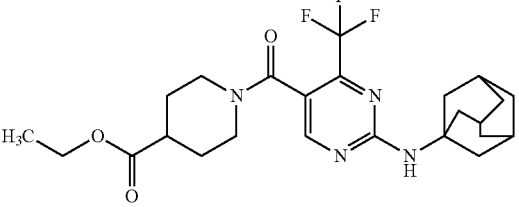 |
| 48 | 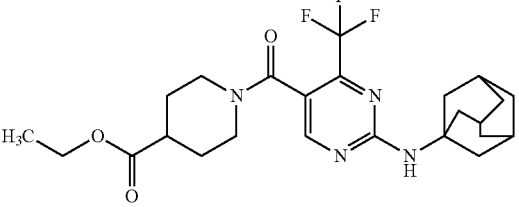 |
| 49 | 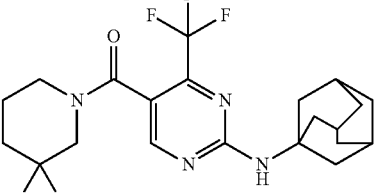 |
| 50 | 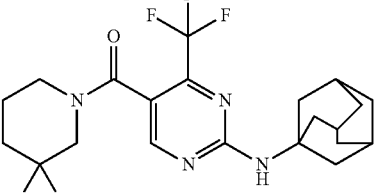 |
| 51 | 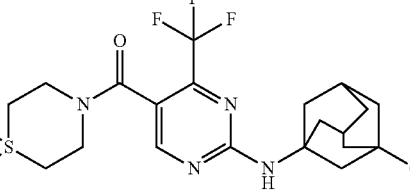 |
| 52 | 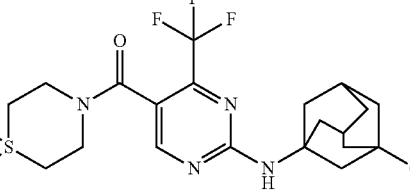 |

TABLE 20-continued
| Ex | Str |
|---|---|
| 53 | 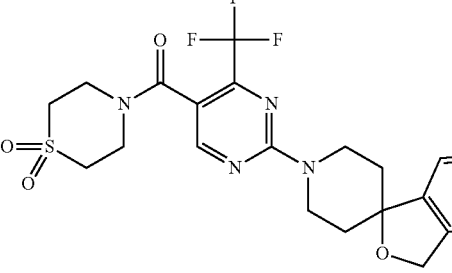 |
| 54 | 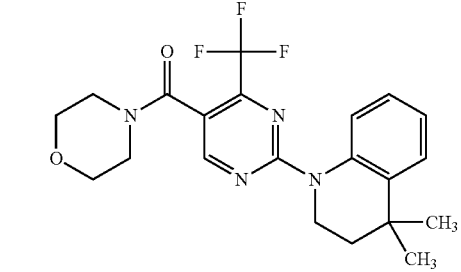 [SMILES: CC1(C)CCN(c2ncc(C(=O)N3CCOCC3)c(C(F)(F)F)n2)c2ccccc21] |
| 55 | 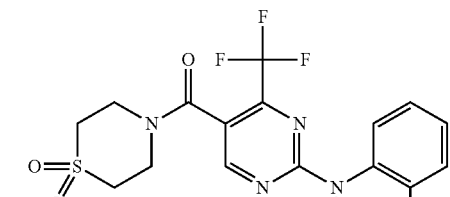 |
TABLE 21
| Ex | Str |
|---|---|
| 56 | 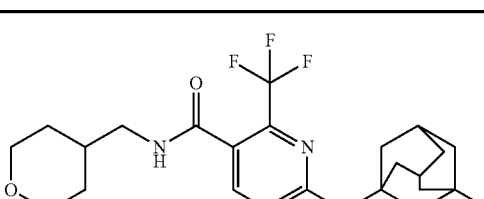 |
| 57 | 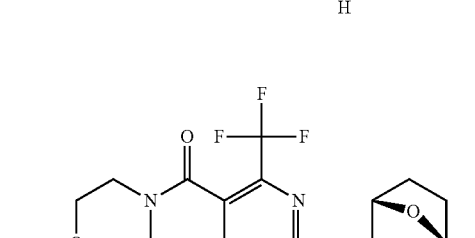 |
TABLE 21-continued
| Ex | Str |
|---|---|
| 58 | 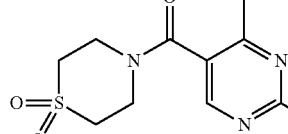 |
| 59 | 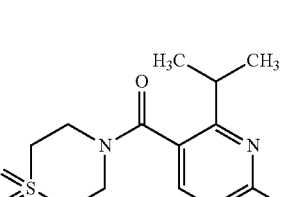 |
| 60 | 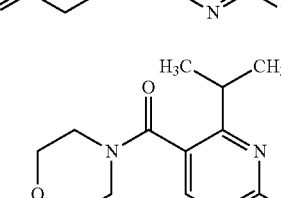 |
| 61 | 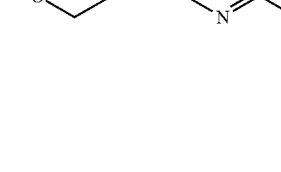 |
| 62 | |
| 63 | |
| 64 | |

TABLE 21-continued
| Ex | Str |
|---|---|
| 65 | |
| 66 | |
| 67 | |
| 68 | |
| 69 | |
| 70 | |
TABLE 22
| Ex | Str |
|---|---|
| 71 | |
TABLE 22-continued
| Ex | Str |
|---|---|
| 72 | |
| 73 | |
| 74 | |
| 75 | |
| 76 | |
| 77 | |
| 78 | 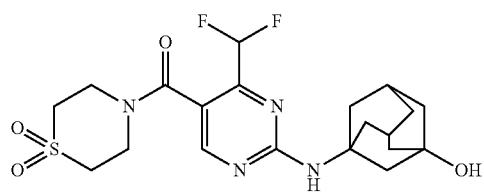 [SMILES: O=C(c1cnc(NC23CC4CC(CC(O)(C4)C2)C3)nc1C(F)F)N1CCS(=O)(=O)CC1] |

TABLE 22-continued
| Ex | Str |
|---|---|
| 79 | 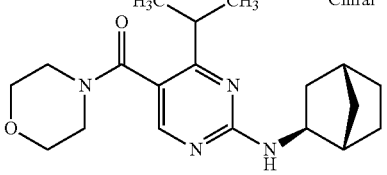 Chiral |
| 80 | 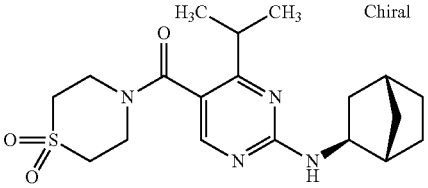 [SMILES: CC(C)c1nc(N[C@H]2C[C@@H]3CC[C@H]2C3)ncc1C(=O)N1CCS(=O)(=O)CC1] Chiral |
| 81 | 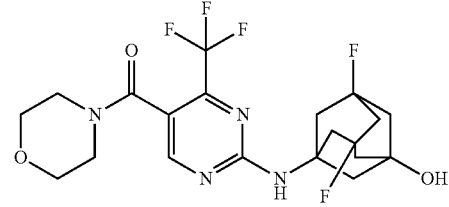 [SMILES: O=C(c1cnc(NC23CC4(O)CC(F)(CC(F)(C4)C2)C3)nc1C(F)(F)F)N1CCOCC1] |
| 82 | 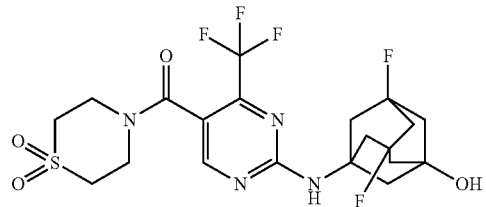 [SMILES: O=C(c1cnc(NC23CC4(O)CC(F)(CC(F)(C4)C2)C3)nc1C(F)(F)F)N1CCS(=O)(=O)CC1] |
| 83 | 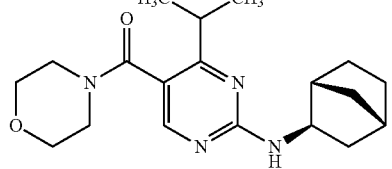 Chiral |
| 84 | 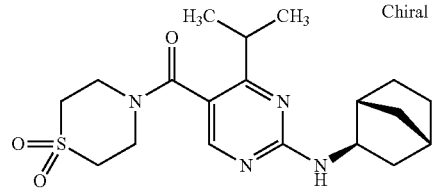 [SMILES: CC(C)c1nc(N[C@@H]2C[C@H]3CC[C@@H]2C3)ncc1C(=O)N1CCS(=O)(=O)CC1] Chiral |
| 85 | 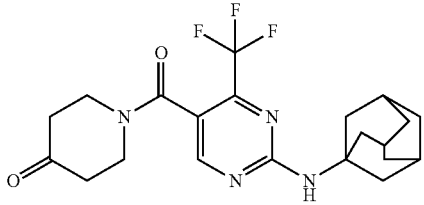 [SMILES: O=C1CCN(C(=O)c2cnc(NC34CC5CC(CC(C5)C3)C4)nc2C(F)(F)F)CC1] |
TABLE 22-continued
| Ex | Str |
|---|---|
| 86 | 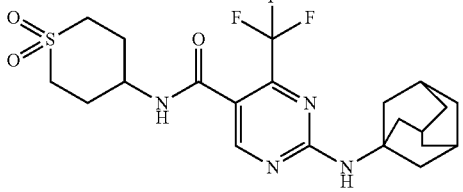 |
TABLE 23
| Ex | Str |
|---|---|
| 87 | 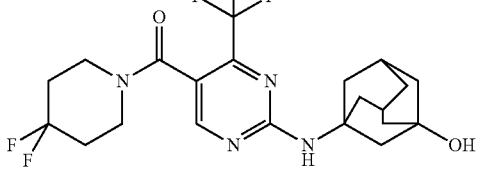 |
| 88 | 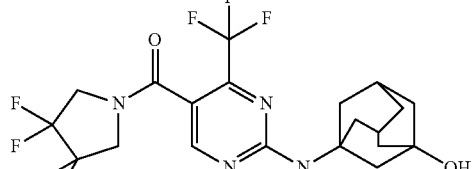 |
| 89 | 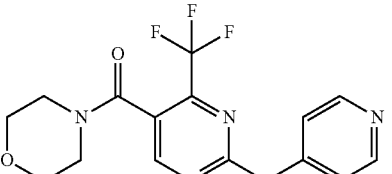 |
| 90 | 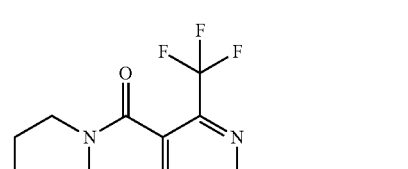 |
| 91 | 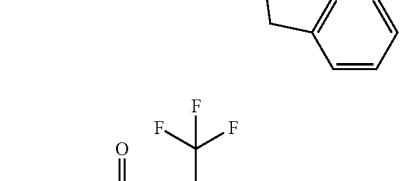 |

TABLE 23-continued

| Ex | Str |
|---|---|
| 92 | (structure) |
| 93 | (structure) |
| 94 | (structure) |
| 95 | (structure) Chiral |
| 96 | (structure) Chiral |
| 97 | (structure) |

TABLE 23-continued

| Ex | Str |
|---|---|
| 98 | (structure) |
| 99 | (structure) |
| 100 | (structure) |

TABLE 24

| Ex | Str |
|---|---|
| 101 | (structure) |
| 102 | (structure) |
| 103 | (structure) |

TABLE 24-continued
| Ex | Str |
|---|---|
| 104 | 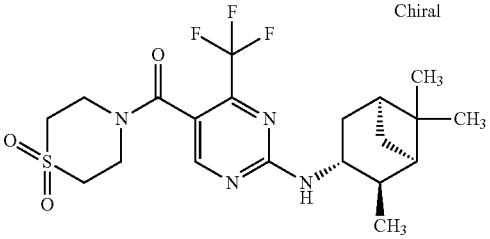 [SMILES: C[C@@H]1[C@H]2C[C@@H](C[C@H]1Nc1ncc(C(=O)N3CCS(=O)(=O)CC3)c(C(F)(F)F)n1)C2(C)C] Chiral |
| 105 | 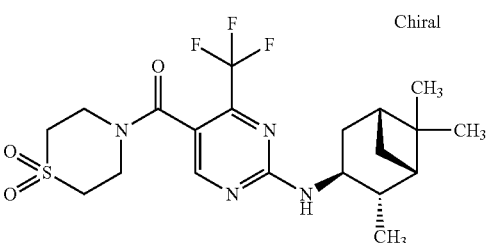 Chiral |
| 106 | 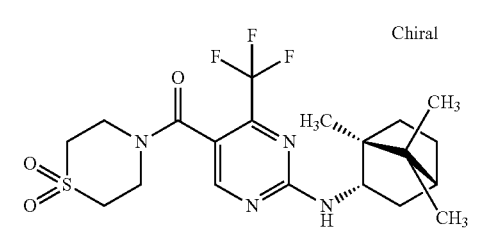 [SMILES: CC1(C)[C@@H]2CC[C@@]1(C)[C@@H](Nc1ncc(C(=O)N3CCS(=O)(=O)CC3)c(C(F)(F)F)n1)C2] Chiral |
| 107 | 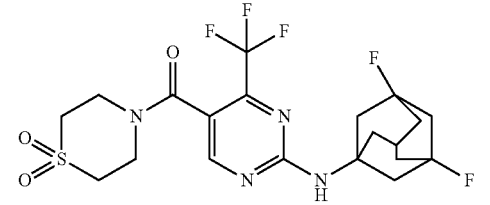 [SMILES: O=C(c1cnc(NC23CC4CC(F)(CC(F)(C4)C2)C3)nc1C(F)(F)F)N1CCS(=O)(=O)CC1] |
| 108 | 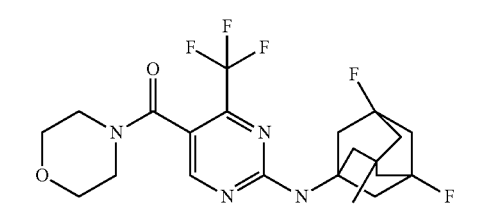 |
| 109 | 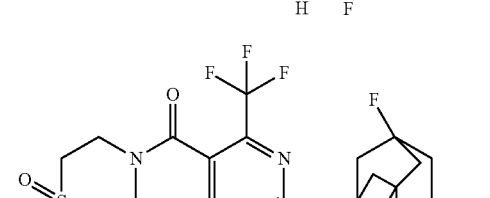 |
| 110 | 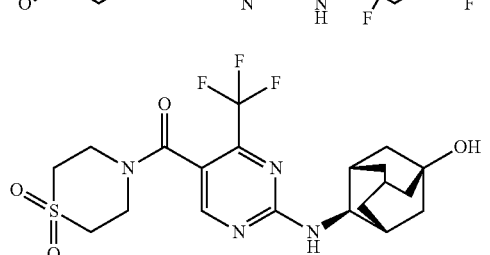 |
TABLE 24-continued
| Ex | Str |
|---|---|
| 111 | 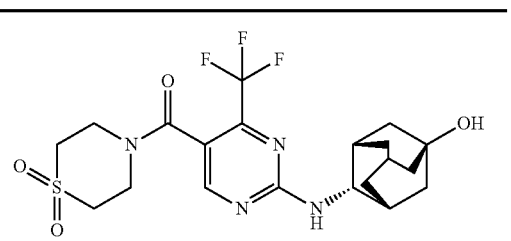 |
| 112 | 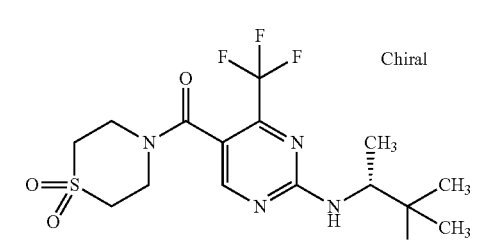 Chiral |
| 113 | 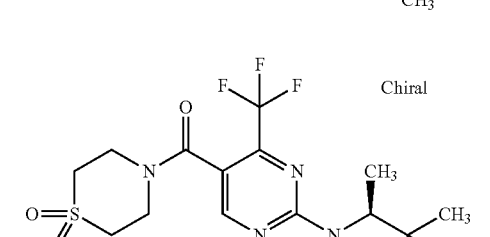 Chiral |
| 114 | 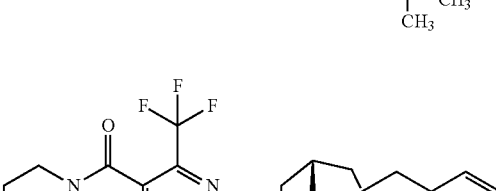 |
TABLE 25
| Ex | Str |
|---|---|
| 115 | 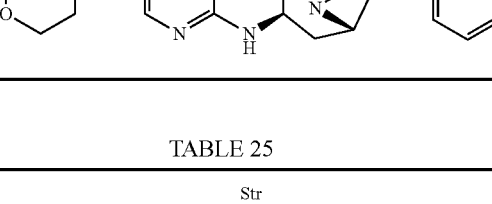 |
| 116 | 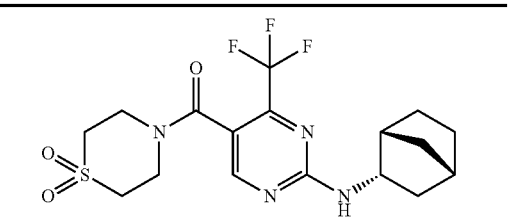 |

TABLE 25-continued

| Ex | Str |
|---|---|
| 117 | |
| 118 | |
| 119 | |
| 120 | |
| 121 | |
| 122 | |

TABLE 25-continued

| Ex | Str |
|---|---|
| 123 | |
| 124 | |
| 125 | |
| 126 | |
| 127 | |
| 128 | |

TABLE 26
| Ex | Str | |
|---|---|---|
| 129 | 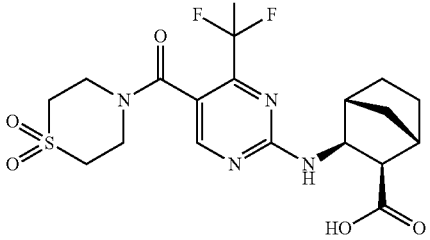 | |
| 130 | 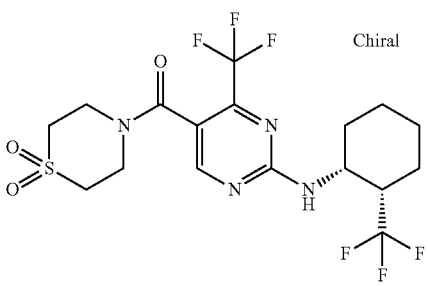 [SMILES: O=C(c1cnc(N[C@@H]2CCCC[C@@H]2C(F)(F)F)nc1C(F)(F)F)N1CCS(=O)(=O)CC1] | Chiral |
| 131 | 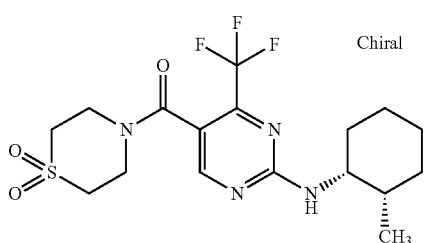 | Chiral |
| 132 | 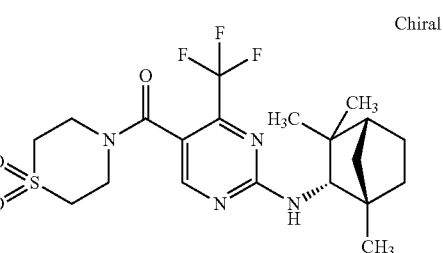 | Chiral |
| 133 | 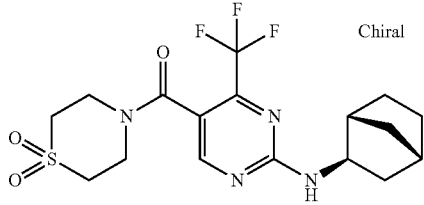 [SMILES: O=C(c1cnc(N[C@@H]2C[C@H]3CC[C@@H]2C3)nc1C(F)(F)F)N1CCS(=O)(=O)CC1] | Chiral |
| 134 | 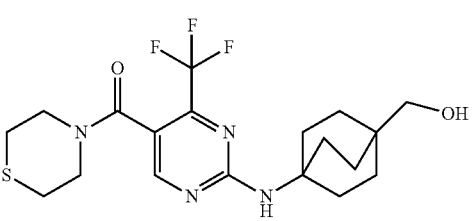 | |

TABLE 26-continued

| Ex | Str |
|---|---|
| 135 | |
| 136 | |
| 137 | |
| 138 | Chiral |
| 139 | |
| 140 | Chiral |
| 141 | Chiral |

TABLE 26-continued

| Ex | Str |
|---|---|
| 142 | (structure) |
| 143 | (structure) |

TABLE 27

| Ex | Str |
|---|---|
| 144 | (structure) |
| 145 | (structure) HCl |
| 146 | (structure) 2HCl |
| 147 | (structure) HCl |
| 148 | (structure) HCl |
| 149 | (structure) HCl |
| 150 | (structure) HCl |
| 151 | (structure) HCl |

TABLE 27-continued

| Ex | Str |
|---|---|
| 152 | (structure) HCl |
| 153 | (structure) HCl |
| 154 | (structure) HCl |
| 155 | (structure) HCl |
| 156 | (structure) HCl |
| 157 | (structure) HCl |

TABLE 28

| Ex | Str |
|---|---|
| 158 | (structure) HCl |
| 159 | (structure) HCl |
| 160 | (structure) HCl |
| 161 | (structure) HCl |
| 162 | (structure) HCl |
| 163 | (structure) HCl |
| 164 | (structure) |

TABLE 28-continued

| Ex | Str |
|---|---|
| 165 | [Structure: morpholine with two CH3 groups (cis-2,6-dimethylmorpholine), CH2 linker to pyrimidine bearing CF3 and NH-adamantyl; HCl salt] |
| 166 | [Structure: thiomorpholine 1,1-dioxide, CH2 linker to pyrimidine bearing CF3 and NH-adamantyl] |
| 167 | [Structure: tetrahydropyran-4-yl O-C(=O)-NH linked to pyrimidine bearing CF3 and NH-(3-chlorophenyl)] |
| 168 | [Structure: 4-methoxyphenyl-O-CH2 linked to pyrimidine bearing CF3 and NH-(3-chlorophenyl)] |
| 169 | [Structure: benzyl-O-CH2 linked to pyrimidine bearing CF3 and NH-(3-chlorophenyl)] |
| 170 | [Structure: morpholine N-C(=O) linked to pyrimidine bearing CF3 and O-norbornyl] |

TABLE 29

| Ex | Syn | DAT |
|---|---|---|
| 1 | 1 | ESI+: 421 [M + Na]<br>NMR1: 1.06-1.23 (5H, m), 1.38-1.77 (8H, m), 2.14-2.17 (1H, m), 2.20-2.24 (1H, m), 3.06-3.10 (2H, m), 3.22-3.29 (2H, m), 3.61-3.72 (1H, m), 3.81-3.87 (2H, m), 8.04-8.13 (1H, m), 8.45-8.56 (2H, m) |

TABLE 29-continued

| Ex | Syn | DAT |
|---|---|---|
| 2 | 2 | ESI+: 499 [M + Na]<br>NMR1: 1.15-1.51 (2H, m), 1.62-1.68 (6H, m), 1.73-1.80 (1H, m), 1.87-1.94 (1H, m), 2.03-2.10 (9H, m), 2.58-2.83 (2H, m), 2.98-3.23 (1H, m), 3.54-3.68 (1H, m), 4.50-4.61 (1H, m), 7.71 (1H, s), 8.51 (1H, s) |
| 3 | 3 | ESI+: 435 [M + Na]<br>NMR1: 0.76 (3H, s), 0.85 (3H, s), 0.94 (3H, s), 1.08-1.15 (1H, m), 1.19-1.28 (1H, m), 1.31-1.41 (1H, m), 1.59-1.69 (2H, m), 1.76-1.88 (1H, m), 2.14-2.25 (1H, m), 3.21-3.69 (8H, m), 4.26-4.47 (1H, m), 8.10-8.18 (1H, m), 8.47 (1H, s) |
| 4 | 4 | ESI+: 393 [M + Na]<br>NMR1: 1.10-1.51 (6H, m), 1.55-1.67 (1H, m), 1.85-1.97 (1H, m), 2.14-2.19 (1H, m), 2.41-2.51 (1H, m), 3.21-3.72 (8H, m), 3.95-4.14 (1H, m), 8.18-8.30 (1H, m), 8.48-8.53 (1H, m) |
| 5 | 5 | ESI+: 509 [M + Na]<br>NMR1: 0.77 (3H, t, J = 7.6 Hz), 1.14 (2H, q, J = 7.6 Hz), 1.35-1.41 (4H, m), 1.51-1.63 (2H, m), 1.75-1.82 (2H, m), 1.95-2.13 (6H, m), 2.90-4.48 (8H, m), 7.82 (1H, s), 8.66 (1H, s) |
| 6 | 6 | ESI+: 471 [M + Na]<br>NMR1: 0.99-1.05 (1H, m), 1.13-1.25 (2H, m), 1.44-1.56 (2H, m), 1.79-1.88 (2H, m), 2.08-2.12 (1H, m), 2.22-2.27 (1H, m), 2.88-4.08 (10H, m), 4.21-4.50 (2H, m), 7.88-7.97 (1H, m), 8.66 (1H, s) |
| 7 | 7 | ESI+: 460 [M + Na]<br>NMR1: 1.98-2.04 (2H, m), 2.90 (2H, t, J = 6.4 Hz), 3.31-3.69 (8H, m), 4.05 (2H, t, J = 6.4 Hz), 8.02-8.03 (2H, m), 8.11-8.13 (1H, m), 8.84 (1H, s) |
| 8 | 8 | ESI+: 451<br>NMR1: 1.95-2.02 (2H, m), 2.84 (2H, t, J = 6.4 Hz), 3.31-3.69 (8H, m), 3.84 (3H, s), 4.02 (2H, t, J = 6.4 Hz), 7.73 (1H, dd, J = 8.4, 2.4 Hz), 7.79-7.81 (1H, m), 7.90 (1H, d, J = 8.4 Hz), 8.78 (1H, s) |

TABLE 30

| Ex | Syn | DAT |
|---|---|---|
| 9 | 9 | ESI+: 433 [M + Na]<br>NMR1: 1.45-1.53 (2H, m), 1.69-1.72 (2H, m), 1.75-1.87 (6H, m), 1.95-2.01 (2H, m), 2.07-2.18 (2H, m), 3.22-3.68 (8H, m), 3.92-4.09 (1H, m), 8.01-8.11 (1H, m), 8.52 (1H, s) |
| 10 | 10 | ESI+: 357<br>NMR1: 1.05-1.25 (3H, m), 1.38-1.58 (4H, m), 1.60-1.70 (1H, m), 2.15-2.25 (2H, m), 3.05-3.25 (2H, m), 3.25-3.42 (2H, m), 3.60-3.78 (1H, m), 3.80-4.00 (4H, m), 4.31 (2H, s), 8.10-8.20 (1H, m), 8.96-9.08 (1H, m), 11.26 (1H, br-s) |
| 11 | 11 | ESI+: 397<br>NMR1: 1.62-1.66 (6H, m), 2.02-2.07 (9H, m), 2.31-2.37 (4H, m), 3.38-3.41 (2H, m), 3.53-3.57 (4H, m), 7.28 (1H, s), 8.49 (1H, s) |
| 12 | 12 | ESI+: 437 [M + Na]<br>NMR1: 1.51-1.64 (4H, m), 2.37-2.46 (1H, m), 3.25-3.33 (2H, m), 3.82-3.88 (2H, m), 4.29-4.34 (2H, m), 7.03-7.07 (1H, m), 7.34 (1H, t, J = 8.1 Hz), 7.64-7.68 (1H, m), 7.97 (1H, t, J = 2.0 Hz), 8.28-8.33 (1H, m), 8.71 (1H, s), 10.36 (1H, s) |

TABLE 30-continued

| Ex | Syn | DAT |
|---|---|---|
| 13 | 13 | ESI+: 437 [M + Na]<br>NMR1: 1.19-1.31 (2H, m), 1.58-1.65 (2H, m), 1.92-2.04 (1H, m), 2.29 (2H, d, J = 7.2 Hz), 3.25-3.34 (2H, m), 3.81-3.87 (2H, m), 7.04-7.08 (1H, m), 7.34 (1H, t, J = 8.1 Hz), 7.63-7.67 (1H, m), 7.96 (1H, t, J = 2.0 Hz), 8.68 (1H, s), 9.76 (1H, s), 10.44 (1H, s) |
| 14 | 14 | ESI+: 415 [M + Na]<br>NMR1: 7.07-7.10 (1H, m), 7.37 (1H, t, J = 8.4 Hz), 7.54-7.59 (2H, m), 7.62-7.71 (2H, m), 7.96-8.00 (3H, m), 8.81 (1H, s), 10.27 (1H, s), 10.51 (1H, s) |
| 15 | 15 | ESI+: 461 [M + Na]<br>NMR1: 7.09-7.09 (1H, m), 7.34 (1H, t, J = 8.0 Hz), 7.58-7.64 (3H, m), 7.68-7.75 (3H, m), 7.88-7.90 (1H, m), 8.24 (1H, s), 10.13 (1H, s), 10.51 (1H, s) |

TABLE 31

| Ex | Syn | DAT |
|---|---|---|
| 16 | 16 | ESI−: 387 |
| 17 | 17 | ESI−: 429<br>NMR1: 1.15-1.34 (2H, m), 1.43-1.65 (2H, m), 1.79-1.95 (1H, m), 3.23-3.37 (2H, m), 3.79-3.89 (2H, m), 3.89-3.99 (2H, m), 7.06 (1H, ddd, J = 0.8, 2, 8 Hz), 7.35 (1H, t, J = 8.2 Hz), 7.65 (1H, ddd, J = 0.8, 2, 8 Hz), 7.95 (1H, t, J = 2 Hz), 8.74 (1H, s), 9.26 (1H, br-s), 10.44 (1H, s) |
| 18 | 18 | ESI−: 414<br>NMR1: 1.32-1.45 (2H, m), 1.73-1.84 (2H, m), 3.34-3.42 (2H, m), 3.61-3.72 (1H, m), 3.76-3.87 (2H, m), 6.77 (1H, d, J = 7.6 Hz), 7.02 (1H, ddd, J = 0.8, 2, 8 Hz), 7.33 (1H, t, J = 8 Hz), 7.65 (1H, ddd, J = 0.8, 2, 8 Hz), 7.84 (1H, br-s), 7.95 (1H, t, J = 2 Hz), 8.91 (1H, s), 10.26 (1H, s) |
| 19 | 19 | ESI−: 378<br>NMR1: 5.13 (2H, br-s), 6.96-7.11 (4H, m), 7.3-7.39 (3H, m), 7.68 (1H, ddd, J = 0.8, 2, 8 Hz), 7.98 (1H, t, J = 2.2 Hz), 8.96 (1H, s), 10.51 (1H, br-s) |
| 20 | 20 | ESI+: 400<br>NMR1: 0.89-1.0 (2H, m), 1.04-1.17 (3H, m), 1.52-1.7 (6H, m), 3.92 (2H, d, J = 7.2 Hz), 4.5 (2H, s), 5.34 (1H, br-s), 7.3-7.34 (2H, m), 7.42-7.47 (2H, m), 8.62 (1H, s) |
| 21 | 21 | ESI+: 442 [M + Na]<br>NMR1: 1.07-1.22 (3H, m), 1.38-1.58 (4H, m), 1.75-1.81 (1H, m), 2.28-2.36 (2H, m), 3.23-3.30 (4H, m), 4.25-4.32 (4H, m), 4.75-4.79 (1H, m), 8.98 (1H, s) |
| 22 | 22 | ESI+: 435<br>NMR1: 1.48-1.59 (1H, m), 1.63-1.82 (2H, m), 1.89-2.00 (1H, m), 2.22-2.28 (1H, m), 2.80-3.02 (5H, m), 3.16-3.40 (5H, m), 3.52-3.94 (3H, m), 4.36-4.52 (1H, m), 5.10-5.15 (1H, m), 9.09 (1H, s) |
| 23 | 23 | ESI+: 444 [M + Na]<br>NMR1: 3.24-3.80 (8H, m), 7.54-7.58 (2H, m), 7.85-7.87 (1H, m), 9.03 (1H, s) |

TABLE 32

| Ex | Syn | DAT |
|---|---|---|
| 24 | 24 | ESI+: 426 [M + Na]<br>NMR1: 3.24-3.76 (8H, m), 7.51-7.66 (3H, m), 7.80 (1H, t, J = 1.8 Hz), 8.96 (1H, s) |
| 25 | 25 | ESI+: 459 [M + Na]<br>NMR1: 1.95-2.02 (2H, m), 2.83 (2H, t, J = 6.4 Hz), 3.27-3.72 (8H, m), 4.02 (2H, t, J = 6.4 Hz), 7.70 (1H, dd, J = 8.4, 2.4 Hz), 7.78 (1H, d, J = 2.4 Hz), 7.87 (1H, d, J = 8.4 Hz), 8.77 (1H, s), 12.73 (1H, s) |

TABLE 32-continued

| Ex | Syn | DAT |
|---|---|---|
| 26 | 26 | ESI+: 451 [M + Na]<br>NMR1: 1.50-1.54 (2H, m), 1.78-1.83 (4H, m), 1.93-2.05 (4H, m), 2.21-2.33 (4H, m), 3.24-3.66 (8H, m), 7.97 (1H, s), 8.52 (1H, s) |
| 27 | 27 | ESI+: 386<br>NMR1: 1.55-1.94 (8H, m), 3.08-3.73 (11H, m), 4.02-4.22 (1H, m), 8.09-8.20 (1H, m), 8.48-8.55 (1H, m) |
| 28 | 28 | ESI+: 450 [M + Na]<br>NMR1: 1.52-2.04 (11H, m), 3.23-3.66 (8H, m), 4.21-4.50 (3H, m), 7.96-8.07 (1H, m), 8.48-8.55 (1H, m) |
| 29 | 29 | ESI+: 447 [M + Na]<br>NMR1: 1.84-2.02 (4H, m), 2.19-2.41 (7H, m), 2.45-2.49 (2H, m), 3.24-3.67 (8H, m), 7.96 (1H, s), 8.53 (1H, s) |
| 30 | 30 | ESI+: 469 [M + Na]<br>NMR1: 1.69-1.82 (4H, m), 2.04-2.12 (5H, m), 2.25-2.35 (4H, m), 3.24-3.68 (8H, m), 7.91 (1H, s), 8.52 (1H, s) |
| 31 | 31 | ESI+: 475 [M + Na]<br>NMR1: 1.27-1.69 (8H, m), 1.73-1.94 (2H, m), 2.03-2.10 (9H, m), 2.48-2.57 (1H, m), 2.88-3.20 (2H, m), 3.42-3.51 (1H, m), 4.21-4.37 (1H, m), 7.69 (1H, s), 8.47 (1H, s), 12.32 (1H, br-s) |
| 32 | 32 | ESI+: 474 [M + Na]<br>NMR1: 1.25-1.69 (9H, m), 1.75-1.81 (1H, m), 2.02-2.10 (9H, m), 2.31-2.40 (1H, m), 2.75-2.84 (1H, m), 2.94-3.13 (1H, m), 3.47-3.55 (1H, m), 4.34-4.46 (1H, m), 6.81 (1H, s), 7.28 (1H, s), 7.70 (1H, s), 8.45 (1H, s) |

TABLE 33

| Ex | Syn | DAT |
|---|---|---|
| 33 | 33 | ESI+: 525 [M + Na]<br>NMR1: 1.56-1.64 (2H, m), 1.71-1.79 (4H, m), 1.91-2.21 (8H, m), 2.89-4.47 (8H, m), 7.88 (1H, s), 8.67 (1H, s), 12.04-12.19 (1H, br-s) |
| 34 | 34 | ESI+: 524 [M + Na]<br>NMR1: 1.54-1.63 (2H, m), 1.66-1.76 (4H, m), 1.89-2.19 (8H, m), 2.88-4.47 (8H, m), 6.73 (1H, s), 6.97 (1H, s), 7.86 (1H, s), 8.66 (1H, s) |
| 35 | 35 | ESI−: 432<br>NMR1: 2.87-3.07 (1H, m), 3.14-3.48 (3H, m), 3.5-3.9 (3H, m), 4.31-4.52 (3H, m), 7.3-7.4 (3H, m), 7.44-7.48 (1H, m), 9.25 (1H, s) |
| 36 | 1 | ESI+: 457 [M + Na]<br>NMR1: 3.22-3.72 (8H, m), 4.54-4.63 (2H, m), 7.34-7.46 (2H, m), 7.60-7.63 (1H, m), 8.53-8.59 (1H, m), 8.66-8.78 (1H, m) |
| 37 | 1 | ESI+: 383 [M + Na]<br>NMR1: 1.48-1.59 (2H, m), 1.77-1.87 (2H, m), 3.22-3.74 (10H, m), 3.83-4.06 (3H, m), 8.11-8.26 (1H, m), 8.49-8.55 (1H, m) |
| 38 | 1 | ESI+: 374<br>NMR1: 1.44-1.59 (2H, m), 1.76-1.86 (2H, m), 1.88-1.99 (2H, m), 2.15 (3H, s), 2.70-2.78 (2H, m), 3.22-3.77 (9H, m), 7.74-8.16 (1H, m), 8.47-8.63 (1H, m) |
| 39 | 1 | ESI+: 415 [M + Na]<br>NMR1: 1.92-2.00 (2H, m), 2.76 (2H, t, J = 6.5 Hz), 3.27-3.73 (8H, m), 3.99 (2H, t, J = 6.2 Hz), 7.05 (1H, dt, J = 7.4, 1.2 Hz), 7.13-7.22 (2H, m), 7.71-7.75 (1H, m), 8.70 (1H, s) |
| 40 | 1 | ESI+: 415 [M + Na]<br>NMR1: 2.87-2.95 (2H, m), 3.22-3.72 (8H, m), 3.96-4.08 (2H, m), 4.91 (2H, s), 7.14-7.32 (4H, m), 8.66 (1H, s) |
| 41 | 1 | ESI+: 461 [M + Na]<br>NMR1: 1.12-1.23 (2H, m), 1.55-1.75 (9H, m), 2.02-2.09 (9H, m), 3.08 (2H, t, J = 6.0 Hz), 3.22-3.29 (2H, m), 3.81-3.87 (2H, m), 7.69 (1H, t, J = 6.0 Hz), 8.46 (1H, t, J = 6.0 Hz), 8.49 (1H, s) |

TABLE 34

| Ex | Syn | DAT |
|---|---|---|
| 42 | 1 | ESI+: 449 [M + Na]<br>NMR1: 1.62-1.67 (6H, m), 2.03-2.10 (9H, m), 2.42-2.72 (4H, m), 3.48-3.95 (4H, m), 7.72 (1H, s), 8.51 (1H, s) |
| 43 | 1 | ESI+: 481 [M + Na]<br>NMR1: 1.61-1.69 (6H, m), 2.03-2.10 (9H, m), 2.87-4.53 (8H, m), 7.80 (1H, s), 8.65 (1H, s) |
| 44 | 1 | ESI+: 447 [M + Na]<br>NMR1: 1.17-1.45 (2H, m), 1.57-1.81 (8H, m), 2.02-2.11 (9H, m), 3.03-3.47 (3H, m), 3.68-3.78 (1H, m), 3.88-4.05 (1H, m), 4.77-4.81 (1H, m), 7.68 (1H, s), 8.45 (1H, s) |
| 45 | 1 | ESI+: 467 [M + Na]<br>NMR1: 1.62-1.68 (6H, m), 1.92-2.11 (13H, m), 3.34-3.82 (4H, m), 7.75 (1H, s), 8.56 (1H, s) |
| 46 | 1 | ESI+: 494<br>NMR1: 1.12-1.50 (2H, m), 1.59-1.91 (8H, m), 2.01-2.11 (9H, m), 2.36-2.54 (4H, m), 2.73-2.84 (1H, m), 2.91-3.13 (1H, m), 3.28-3.35 (1H, m), 3.46-3.61 (5H, m), 4.35-4.45 (1H, m), 7.69 (1H, s), 8.42-8.52 (1H, m) |
| 47 | 1 | ESI+: 524 [M + Na]<br>NMR1: 1.63-1.68 (6H, m), 2.04-2.12 (9H, m), 3.03-3.07 (4H, m), 3.72-3.76 (4H, m), 6.91-6.95 (2H, m), 7.48-7.53 (2H, m), 7.78 (1H, s), 8.66 (1H, s), 10.24 (1H, s) |
| 48 | 1 | ESI+: 454<br>NMR1: 1.61-1.68 (6H, m), 2.03-2.09 (9H, m), 2.35-2.44 (6H, m), 3.28-3.35 (2H, m), 3.54-3.59 (4H, m), 7.69 (1H, s), 8.38 (1H, t, J = 5.6 Hz), 8.47 (1H, s) |
| 49 | 1 | ESI+: 503 [M + Na]<br>NMR1: 1.18 (3H, t, J = 7.2 Hz), 1.32-1.68 (8H, m), 1.74-1.94 (2H, m), 2.03-2.10 (9H, m), 2.59-2.68 (1H, m), 2.88-2.97 (1H, m), 3.01-3.18 (1H, m), 3.44-3.52 (1H, in), 4.08 (2H, q, J = 7.2 Hz), 4.23-4.35 (1H, m), 7.69 (1H, s), 8.47 (1H, s) |

TABLE 35

| Ex | Syn | DAT |
|---|---|---|
| 50 | 1 | ESI+: 467 [M + Na]<br>NMR1: 1.62-1.68 (8H, m), 2.04-2.11 (11H, m), 3.27-4.10 (4H, m), 7.76 (1H, s), 8.35-8.45 (1H, m) |
| 51 | 1 | ESI+: 497 [M + Na]<br>NMR1: 1.42-1.60 (6H, m), 1.87-2.02 (6H, m), 2.14-2.20 (2H, m), 2.85-4.46 (8H, m), 4.53 (1H, s), 7.88 (1H, s), 8.66 (1H, s) |
| 52 | 1 | ESI+: 471 [M + Na]<br>NMR1: 1.71-1.80 (2H, m), 1.88-1.99 (2H, m), 3.26-3.74 (10H, m), 4.65-4.76 (2H, m), 5.06 (2H, s), 7.23-7.32 (4H, m), 8.62 (1H, s) |
| 53 | 1 | ESI+: 519 [M + Na]<br>NMR1: 1.71-1.81 (2H, m), 1.88-1.99 (2H, m), 2.89-4.50 (10H, m), 4.64-4.82 (2H, m), 5.06 (2H, s), 7.24-7.33 (4H, m), 8.77 (1H, s) |
| 54 | 1 | ESI+: 421<br>NMR1: 1.28 (6H, s), 1.78-1.85 (2H, m), 3.28-3.78 (8H, m), 3.99-4.08 (2H, m), 7.06-7.17 (2H, m), 7.40 (1H, dd, J = 7.6, 1.7 Hz), 7.69 (1H, dd, J = 8.0, 1.5 Hz), 8.69 (1H, s) |
| 55 | 1 | ESI+: 491 [M + Na]<br>NMR1: 1.29 (6H, s), 1.82 (2H, t, J = 6.1 Hz), 2.85-4.58 (10H, m), 7.07-7.18 (2H, m), 7.41 (1H, dd, J = 7.6, 1.8 Hz), 7.70 (1H, dd, J = 8.0, 1.4 Hz), 8.83 (1H, s) |
| 56 | 1 | ESI+: 477 [M + Na]<br>NMR1: 1.12-1.23 (2H, m), 1.43-1.62 (8H, m), 1.65-1.75 (1H, m), 1.89-2.00 (6H, m), 2.14-2.19 (2H, m), 3.05-3.11 (2H, m), 3.22-3.30 (2H, m), 3.81-3.88 (2H, m), 4.53 (1H, s), 7.78 (1H, s), 8.47 (1H, t, J = 6.4 Hz), 8.50 (1H, s) |
| 57 | 1 | ESI+: 395 [M + Na]<br>NMR1: 1.36-1.49 (2H, m), 1.52-1.65 (2H, m), 1.78-1.90 (1H, m), 2.00-2.10 (1H, m), 3.19-3.77 (8H, m), 3.94-4.13 (1H, m), 4.46-4.52 (1H, m), 4.58-4.64 (1H, m), 8.46-8.58 (2H, m) |

TABLE 35-continued

| Ex | Syn | DAT |
|---|---|---|
| 58 | 1 | ESI+: 443 [M + Na]<br>NMR1: 1.36-1.49 (2H, m), 1.53-1.65 (2H, m), 1.78-1.91 (1H, m), 2.00-2.11 (1H, m), 2.83-4.65 (11H, m), 8.53-8.61 (1H, m), 8.71 (1H, s) |

TABLE 36

| Ex | Syn | DAT |
|---|---|---|
| 59 | 1 | ESI+: 423 [M + Na]<br>NMR1: 1.25-1.38 (7H, m), 1.43-1.53 (1H, m), 1.56-1.64 (1H, m), 1.76-1.86 (1H, m), 1.90-2.01 (1H, m), 2.10-2.24 (1H, m), 3.20-3.74 (8H, m), 4.09-4.28 (1H, m), 8.37-8.44 (1H, m), 8.51 (1H, s) |
| 60 | 1 | ESI+: 471 [M + Na]<br>NMR1: 1.24-1.39 (7H, m), 1.43-1.54 (1H, m), 1.56-1.64 (1H, m), 1.76-1.86 (1H, m), 1.91-2.01 (1H, m), 2.11-2.23 (1H, m), 2.80-4.53 (9H, m), 8.44-8.52 (1H, m), 8.66-8.72 (1H, m) |
| 61 | 1 | ESI+: 395 [M + Na]<br>NMR1: 1.37-1.60 (4H, m), 1.64-1.77 (1H, m), 1.84-1.94 (1H, m), 3.18-3.90 (9H, m), 4.34-4.39 (1H, m), 4.52-4.57 (1H, m), 8.06-8.14 (1H, m), 8.48-8.58 (1H, m) |
| 62 | 1 | ESI+: 443 [M + Na]<br>NMR1: 1.36-1.60 (4H, m), 1.64-1.77 (1H, m), 1.84-1.95 (1H, m), 2.80-4.59 (11H, m), 8.12-8.21 (1H, m), 8.66-8.72 (1H, m) |
| 63 | 1 | ESI+: 471 [M + Na]<br>NMR1: 1.14 (6H, d, J = 6.8 Hz), 1.43-1.60 (6H, m), 1.91-2.02 (6H, m), 2.14-2.19 (2H, m), 2.86-2.95 (1H, m), 3.11-3.34 (6H, m), 3.59-3.92 (2H, m), 4.49 (1H, s), 6.98 (1H, s), 8.22 (1H, s) |
| 64 | 1 | ESI+: 367 [M + Na]<br>NMR1: 1.04-1.20 (9H, m), 1.39-1.66 (5H, m), 2.16-2.12 (2H, m), 2.87-2.96 (1H, m), 3.21-3.69 (9H, m), 7.26 (1H, s), 8.08 (1H, s) |
| 65 | 1 | ESI+: 415 [M + Na]<br>NMR1: 1.04-1.21 (9H, m), 1.37-1.67 (5H, m), 2.15-2.22 (2H, m), 2.85-2.95 (1H, m), 3.10-3.91 (9H, m), 7.32 (1H, s), 8.24 (1H, s) |
| 66 | 1 | ESI+: 343<br>NMR1: 0.92-1.17 (7H, m), 1.37-1.51 (4H, m), 1.55-1.62 (1H, m), 1.86-1.94 (1H, m), 2.10-2.20 (2H, m), 3.24-3.69 (9H, m), 7.04-7.29 (1H, m), 8.03 (1H, s) |

TABLE 37

| Ex | Syn | DAT |
|---|---|---|
| 67 | 1 | ESI+: 413 [M + Na]<br>NMR1: 0.90-1.18 (7H, m), 1.37-1.63 (5H, m), 1.90-2.00 (1H, m), 2.10-2.21 (2H, m), 3.10-3.36 (5H, m), 3.46-4.21 (4H, m), 7.10-7.33 (1H, m), 8.14 (1H, s) |
| 68 | 1 | ESI+: 429 [M + Na]<br>NMR1: 1.36-2.22 (10H, m), 3.34-3.92 (5H, m), 4.34-4.41 (1H, m), 4.52-4.58 (1H, m), 8.07-8.18 (1H, m), 8.55-8.65 (1H, m) |
| 69 | 1 | ESI+: 451 [M + Na]<br>NMR1: 1.38-1.61 (4H, m), 1.66-1.78 (1H, m), 1.85-1.95 (1H, m), 3.82-3.92 (1H, m), 4.13-4.28 (4H, m), 4.35-4.40 (1H, m), 4.53-4.58 (1H, m), 8.22-8.29 (1H, m), 8.59-8.67 (1H, m) |
| 70 | 1 | ESI+: 415 [M + Na]<br>NMR1: 1.38-1.60 (4H, m), 1.65-1.77 (1H, m), 1.84-1.95 (1H, m), 2.38-2.54 (2H, m), 3.47-3.56 (1H, m), 3.64-3.92 (4H, m), 4.34-4.39 (1H, m), 4.52-4.58 (1H, m), 8.12-8.22 (1H, m), 8.54-8.66 (1H, m) |
| 71 | 1 | ESI+: 469 [M + Na]<br>NMR1: 0.94-1.08 (4H, m), 1.42-1.59 (6H, m), 1.85-1.99 (7H, m), 2.12-2.18 (2H, m), 3.14-3.33 (4H, m), 3.61-4.17 (4H, m), 4.49 (1H, s), 6.92 (1H, s), 8.13 (1H, s) |

TABLE 37-continued

| Ex | Syn | DAT |
|----|-----|-----|
| 72 | 1 | ESI+: 359<br>NMR1: 1.03-1.33 (12H, m), 1.37-1.65 (5H, m), 2.15-2.24 (2H, m), 3.16-3.24 (1H, m), 3.28-3.36 (1H, m), 3.45-3.69 (7H, m), 7.03-7.27 (1H, m), 7.98 (1H, s) |
| 73 | 1 | ESI+: 429 [M + Na]<br>NMR1: 1.04-1.21 (3H, m), 1.25 (9H, s), 1.38-1.53 (4H, m), 1.58-1.66 (1H, m), 2.17-2.23 (2H, m), 2.96-3.04 (1H, m), 3.16-3.23 (1H, m), 3.28-3.66 (5H, m), 3.79-3.87 (1H, m), 4.53-4.63 (1H, m), 7.11-7.33 (1H, m), 8.24 (1H, s) |
| 74 | 1 | ESI+: 485 [M + Na]<br>NMR1: 1.26 (9H, s), 1.42-1.61 (6H, m), 1.89-2.03 (6H, m), 2.13-2.19 (2H, m), 2.96-3.04 (1H, m), 3.16-3.23 (1H, m), 3.28-3.56 (4H, m), 3.79-3.88 (1H, m), 4.49 (1H, s), 4.52-4.61 (1H, m), 6.95 (1H, s), 8.24 (1H, s) |

TABLE 38

| Ex | Syn | DAT |
|----|-----|-----|
| 75 | 1 | ESI+: 369 [M + Na]<br>NMR1: 1.03-1.28 (3H, m), 1.37-1.66 (5H, m), 2.13-2.22 (2H, m), 3.19-3.69 (12H, m), 4.28 (2H, s), 7.51 (1H, s), 8.17 (1H, s) |
| 76 | 1 | ESI+: 417 [M + Na]<br>NMR1: 1.04-1.20 (3H, m), 1.37-1.66 (5H, m), 2.14-2.22 (2H, m), 3.11-3.30 (7H, m), 3.63-4.03 (5H, m), 4.31 (2H, s), 7.50-7.64 (1H, m), 8.28 (1H, s) |
| 77 | 1 | ESI+: 473 [M + Na]<br>NMR1: 1.41-1.60 (6H, m), 1.89-2.00 (6H, m), 2.12-2.18 (2H, m), 3.12-3.20 (4H, m), 3.28 (3H, m), 3.62-4.05 (4H, m), 4.31 (2H, s), 4.48 (1H, s), 7.22 (1H, s), 8.25 (1H, s) |
| 78 | 1 | ESI+: 479 [M + Na]<br>NMR1: 1.41-1.61 (6H, m), 1.88-2.04 (6H, m), 2.13-2.19 (2H, m), 3.16-3.27 (4H, m), 3.71-4.03 (4H, m), 4.51 (1H, s), 6.82 (1H, t, J = 53.2 Hz), 7.71 (1H, s), 8.51 (1H, s) |
| 79 | 1 | $[\alpha]_D = -13.9$ (c 0.8, MeOH)<br>ESI+: 367 [M + Na]<br>NMR1: 1.04-1.28 (9H, m), 1.38-1.67 (5H, m), 2.15-2.23 (2H, m), 2.87-2.97 (1H, m), 3.21-3.68 (9H, m), 7.25 (1H, s), 8.07 (1H, s) |
| 80 | 1 | $[\alpha]_D^{27} = 0$ (c 0.6, MeOH)<br>ESI+: 415 [M + Na]<br>NMR1: 1.04-1.21 (9H, m), 1.38-1.66 (5H, m), 2.16-2.23 (2H, m), 2.85-2.95 (1H, m), 3.07-4.38 (9H, m), 7.31 (1H, s), 8.23 (1H, s) |
| 81 | 1 | ESI+: 485 [M + Na]<br>NMR1: 1.74-1.88 (4H, m), 1.93-2.26 (8H, m), 3.25-3.67 (8H, m), 5.25 (1H, s), 8.21 (1H, s), 8.57 (1H, s) |
| 82 | 1 | ESI+: 533 [M + Na]<br>NMR1: 1.74-1.90 (4H, m), 1.93-2.27 (8H, m), 2.89-4.48 (8H, m), 5.26 (1H, s), 8.28 (1H, s), 8.73 (1H, s) |
| 83 | 1 | $[\alpha]_D^{29} = +14.1$ (c 0.7, MeOH)<br>ESI+: 345<br>NMR1: 1.04-1.25 (9H, m), 1.38-1.65 (5H, m), 2.16-2.22 (2H, m), 2.88-2.96 (1H, m), 3.18-3.75 (9H, m), 7.24 (1H, s), 8.07 (1H, s) |

TABLE 39

| Ex | Syn | DAT |
|----|-----|-----|
| 84 | 1 | $[\alpha]_D^{29} = -0.84$ (c 0.8, MeOH)<br>ESI+: 415 [M + Na]<br>NMR1: 1.03-1.21 (9H, m), 1.38-1.67 (5H, m), 2.16-2.22 (2H, m), 2.86-2.94 (1H, m), 3.06-3.37 (5H, m), 3.56-4.24 (4H, m), 7.30 (1H, s), 8.24 (1H, s) |
| 85 | 2 | ESI-: 421<br>NMR1: 1.61-1.69 (6H, m), 2.03-2.11 (9H, m), 2.29-2.50 (4H, m), 3.55-3.95 (4H, m), 7.74 (1H, s), 8.59 (1H, s) |
| 86 | 2 | ESI+: 495 [M + Na]<br>NMR1: 1.61-1.68 (6H, m), 1.90-2.17 (13H, m), 3.08-3.16 (2H, m), 3.21-3.30 (2H, m), 4.03-4.13 (1H, m), 7.74 (1H, s), 8.52-8.58 (2H, m) |
| 87 | 2 | ESI+: 483 [M + Na]<br>NMR1: 1.42-1.60 (6H, m), 1.86-2.12 (10H, m), 2.13-2.19 (2H, m), 3.34-3.88 (4H, m), 4.53 (1H, s), 7.84 (1H, s), 8.57 (1H, s) |
| 88 | 2 | ESI+: 505 [M + Na]<br>NMR1: 1.43-1.60 (6H, m), 1.89-2.01 (6H, m), 2.14-2.20 (2H, m), 4.12-4.29 (4H, m), 4.54 (1H, s), 7.97 (1H, s), 8.60 (1H, s) |
| 89 | 3 | ESI+: 354<br>NMR1: 3.27-3.78 (8H, m), 7.74-7.78 (2H, m), 8.42-8.45 (2H, m), 8.88 (1H, s), 10.83 (1H, s) |
| 90 | 3 | ESI+: 401 [M + Na]<br>NMR1: 3.21-3.72 (8H, m), 4.88 (1H, s), 4.91 (2H, s), 7.31-7.36 (2H, m), 7.41-7.48 (2H, m), 8.70 (1H, s) |
| 91 | 3 | ESI+: 401 [M + Na]<br>NMR1: 3.22 (2H, t, J = 8.4 Hz), 3.29-3.36 (3H, m), 3.44-3.72 (5H, m), 4.24 (2H, t, J = 8.4 Hz), 7.00-7.05 (1H, m), 7.22-7.33 (2H, m), 8.27 (1H, d, J = 8.0 Hz), 8.84 (1H, s) |
| 92 | 3 | ESI+: 381 [M + Na]<br>NMR1: 1.07-1.35 (5H, m), 1.55-1.63 (1H, m), 1.67-1.77 (2H, m), 1.82-1.92 (2H, m), 3.23-3.79 (9H, m), 7.97-8.14 (1H, m), 8.44-8.54 (1H, m) |
| 93 | 3 | ESI+: 447 [M + Na]<br>NMR1: 1.47-1.52 (6H, m), 1.56-1.69 (6H, m), 1.89-1.95 (3H, m), 3.02-3.14 (2H, m), 3.25-3.67 (8H, m), 8.03-8.14 (1H, m), 8.46-8.49 (1H, m) |

TABLE 40

| Ex | Syn | DAT |
|----|-----|-----|
| 94 | 3 | ESI+: 429 [M + Na]<br>NMR1: 1.28 (3H, d, J = 6.8 Hz), 1.57-1.66 (1H, m), 2.08-2.17 (1H, m), 2.86-2.95 (1H, m), 3.30-3.69 (8H, m), 4.00 (2H, t, J = 6.8 Hz), 7.07-7.11 (1H, m), 7.14-7.19 (1H, m), 7.26-7.29 (1H, m), 7.71 (1H, dd, J = 8.4, 1.6 Hz), 8.69 (1H, s) |
| 95 | 3 | ESI+: 435 [M + Na]<br>NMR1: 1.02-1.06 (6H, m), 1.12-1.17 (1H, m), 1.22 (3H, s), 1.58-1.68 (1H, m), 1.77-1.81 (1H, m), 1.89-1.95 (1H, m), 2.06-2.15 (1H, m), 2.28-2.36 (1H, m), 2.45-2.55 (1H, m), 3.26-3.66 (8H, m), 4.23-4.44 (1H, m), 8.18-8.31 (1H, m), 8.47-8.52 (1H, m) |
| 96 | 3 | ESI+: 435 [M + Na]<br>NMR1: 1.02-1.07 (6H, m), 1.13-1.17 (1H, m), 1.22 (3H, s), 1.58-1.68 (1H, m), 1.77-1.81 (1H, m), 1.89-1.95 (1H, m), 2.06-2.15 (1H, m), 2.28-2.36 (1H, m), 2.45-2.55 (1H, m), 3.26-3.68 (8H, m), 4.23-4.44 (1H, m), 8.18-8.29 (1H, m), 8.47-8.52 (1H, m) |
| 97 | 3 | ESI+: 407<br>NMR1: 1.31-2.03 (4H, m), 2.54-3.13 (2H, m), 3.25-4.92 (10H, m), 7.20-7.35 (4H, m), 8.41-8.74 (1H, m) |
| 98 | 3 | ESI+: 449 [M + Na]<br>NMR1: 1.96-2.03 (2H, m), 2.82 (2H, t, J = 7.2 Hz), 3.28-3.69 (8H, m), 4.04-4.08 (2H, m), 7.17-7.25 (2H, m), 7.68-7.72 (1H, m), 8.72 (1H, s) |
| 99 | 3 | ESI+: 463 [M + Na]<br>NMR2: 1.54-1.65 (2H, m), 1.70-1.80 (4H, m), 1.96-2.15 (6H, m), 2.31-2.36 (2H, m), 3.26 (3H, m), 3.31-3.36 (2H, m), 3.60-3.66 (2H, m), 3.70-3.88 (4H, m), 5.51 (1H, s), 8.29 (1H, s) |
| 100 | 3 | ESI+: 491 [M + Na]<br>NMR1: 1.52-1.57 (2H, m), 1.91-2.10 (11H, m), 2.22-2.27 (2H, m), 2.38-2.45 (2H, m), 3.25-3.67 (8H, m), 7.90 (1H, s), 8.51 (1H, s) |
| 101 | 3 | ESI+: 491 [M + Na]<br>NMR1: 1.53-1.60 (2H, m), 1.81-1.89 (4H, m), 1.94-2.24 (7H, m), 3.23-3.69 (8H, m), 3.86-3.89 (4H, m), 7.77 (1H, s), 8.49 (1H, s) |

TABLE 41

| Ex | Syn | DAT |
|---|---|---|
| 102 | 3 | ESI+: 393 [M + Na]<br>NMR1: 1.05-1.30 (3H, m), 1.38-1.56 (4H, m), 1.60-1.70 (1H, m), 2.16-2.25 (2H, m), 3.21-3.74 (9H, m), 8.02-8.15 (1H, m), 8.45-8.55 (1H, m) |
| 103 | 3 | ESI+: 441 [M + Na]<br>NMR1: 1.07-1.21 (3H, m), 1.38-1.56 (4H, m), 1.61-1.70 (1H, m), 2.17-2.24 (2H, m), 2.87-4.48 (9H, m), 8.11-8.21 (1H, m), 8.65-8.68 (1H, m) |
| 104 | 3 | ESI+: 483 [M + Na]<br>NMR1: 1.03-1.07 (6H, m), 1.13-1.17 (1H, m), 1.22 (3H, s), 1.59-1.69 (1H, m), 1.77-1.82 (1H, m), 1.89-1.95 (1H, m), 2.07-2.16 (1H, m), 2.28-2.36 (1H, m), 2.46-2.55 (1H, m), 2.89-3.38 (6H, m), 3.55-3.93 (2H, m), 4.22-4.44 (1H, m), 8.25-8.36 (1H, m), 8.64-8.67 (1H, m) |
| 105 | 3 | ESI+: 483 [M + Na]<br>NMR1: 1.03-1.07 (6H, m), 1.13-1.17 (1H, m), 1.22 (3H, s), 1.59-1.69 (1H, m), 1.77-1.81 (1H, m), 1.89-1.95 (1H, m), 2.07-2.16 (1H, m), 2.29-2.36 (1H, m), 2.45-2.55 (1H, m), 2.93-3.39 (6H, m), 3.57-3.91 (2H, m), 4.22-4.46 (1H, m), 8.25-8.36 (1H, m), 8.64-8.66 (1H, m) |
| 106 | 3 | ESI+: 483 [M + Na]<br>NMR1: 0.76 (3H, s), 0.85 (3H, s), 0.94 (3H, s), 1.09-1.15 (1H, m), 1.19-1.28 (1H, m), 1.33-1.41 (1H, m), 1.60-1.69 (2H, m), 1.77-1.87 (1H, m), 2.14-2.25 (1H, m), 2.85-3.39 (6H, m), 3.49-3.93 (2H, m), 4.25-4.49 (1H, m), 8.17-8.25 (1H, m), 8.60-8.67 (1H, m) |
| 107 | 3 | ESI+: 517 [M + Na]<br>NMR1: 1.72-1.84 (4H, m), 1.90-1.94 (2H, m), 2.05-2.11 (2H, m), 2.16-2.34 (4H, m), 2.41-2.48 (1H, m), 2.89-4.48 (8H, m), 8.24 (1H, s), 8.72 (1H, s) |
| 108 | 3 | ESI+: 487 [M + Na]<br>NMR1: 2.05-2.12 (3H, m), 2.18-2.30 (9H, m), 3.27-3.68 (8H, m), 8.34 (1H, s), 8.59 (1H, s) |
| 109 | 3 | ESI+: 535 [M + Na]<br>NMR1: 2.03-2.15 (3H, m), 2.17-2.33 (9H, m), 2.88-4.48 (8H, m), 8.41 (1H, s), 8.75 (1H, s) |

TABLE 42

| Ex | Syn | DAT |
|---|---|---|
| 110 | 3 | ESI+: 497 [M + Na]<br>NMR1: 1.29-1.35 (2H, m), 1.60-1.74 (6H, m), 1.96-2.12 (5H, m), 2.88-4.03 (9H, m), 4.43 (1H, s), 8.08-8.14 (1H, m), 8.66-8.71 (1H, m) |
| 111 | 3 | ESI+: 497 [M + Na]<br>NMR1: 1.34-1.40 (2H, m), 1.56-1.67 (6H, m), 1.93-2.05 (3H, m), 2.19-2.24 (2H, m), 2.88-3.95 (9H, m), 4.33 (1H, s), 8.01-8.12 (1H, m), 8.65-8.72 (1H, m) |
| 112 | 3 | ESI+: 431 [M + Na]<br>NMR1: 0.9 (9H, s), 1.09 (3H, d, J = 6.4 Hz), 2.82-4.64 (9H, m), 7.91-8.04 (1H, m), 8.64 (1H, d, J = 12.4 Hz) |
| 113 | 3 | ESI+: 431 [M + Na]<br>NMR1: 0.9 (9H, s), 1.08 (3H, d, J = 6.8 Hz), 2.82-4.64 (9H, m), 7.91-8.04 (1H, m), 8.64 (1H, d, J = 12.4 Hz) |
| 114 | 4 | ESI+: 476<br>NMR1: 1.56-1.73 (6H, m), 1.97-2.04 (2H, m), 3.13-3.19 (2H, m), 3.23-3.66 (10H, m), 4.02-4.24 (1H, m), 7.20-7.26 (1H, m), 7.29-7.38 (4H, m), 7.97-8.10 (1H, m), 8.46-8.53 (1H, m) |
| 115 | 4 | ESI+: 441 [M + Na]<br>NMR1: 1.09-1.69 (7H, m), 1.85-1.97 (1H, m), 2.15-2.20 (1H, m), 2.42-2.53 (1H, m), 2.85-4.55 (9H, m), 8.25-8.35 (1H, m), 8.65-8.67 (1H, m) |
| 116 | 4 | ESI+: 455 [M + Na]<br>NMR1: 1.07-1.28 (3H, m), 1.33-1.6 (3H, m), 1.42 (3H, s), 1.71 (1H, d, J = 9.2 Hz), 2.03 (1H, br-s), 2.16 (1H, br-s), 2.54-2.65 (1H, m), 2.84-4.55 (8H, m), 7.96 (1H, d, J = 16.4 Hz), 8.65 (1H, s) |
| 117 | 4 | ESI+: 509 [M + Na]<br>NMR2: 1.36-1.51 (3H, m), 1.53-1.61 (1H, m), 1.65-1.77 (2H, m), 2.24-2.35 (1H, m), 2.36-2.41 (1H, m), 2.63 (1H, br-s), 2.97 (2H, br-s), 3.15 (2H, br-s), 3.86 (2H, br-s), 4.1 (2H, br-s), 4.52 (1H, br-s), 5.57 (1H, d, J = 8 Hz), 8.38 (1H, br-s) |

TABLE 43

| Ex | Syn | DAT |
|---|---|---|
| 118 | 4 | ESI+: 509 [M + Na]<br>NMR2: 1.33-1.44 (2H, m), 1.49-1.66 (2H, m), 1.68-1.86 (3H, m), 2.53 (1H, d, J = 3.2 Hz), 2.59-2.74 (1H, m), 2.9-3.05 (2H, m), 3.15 (2H, br-s), 3.73-4.19 (3H, m), 4.31-4.62 (2H, m), 5.74 (1H, d, J = 8 Hz), 8.38 (1H, br-s) |
| 119 | 5 | ESI+: 461 [M + Na]<br>NMR1: 0.83 (6H, s), 1.13-1.15 (2H, m), 1.24-1.37 (4H, m), 1.63-1.79 (4H, m), 1.89-1.93 (2H, m), 2.09-2.14 (1H, m), 3.25-3.35 (3H, m), 3.45-3.67 (5H, m), 7.73 (1H, s), 8.49 (1H, s) |
| 120 | 5 | ESI+: 469 [M + Na]<br>NMR1: 1.72-1.84 (4H, m), 1.89-1.94 (2H, m), 2.04-2.10 (2H, m), 2.16-2.23 (2H, m), 2.26-2.33 (2H, m), 2.40-2.47 (1H, m), 3.26-3.35 (2H, m), 3.42-3.68 (6H, m), 8.18 (1H, s), 8.56 (1H, s) |
| 121 | 5 | ESI+: 523 [M + Na]<br>NMR1: 0.80 (6H, d, J = 8.0 Hz), 1.19-1.28 (1H, m), 1.39-1.43 (4H, m), 1.50-1.62 (2H, m), 1.78-2.14 (8H, m), 2.87-4.47 (8H, m), 7.81 (1H, s), 8.66 (1H, s) |
| 122 | 5 | ESI+: 455 [M + Na]<br>NMR1: 1.52-1.69 (7H, m), 1.87-1.97 (6H, m), 2.88-4.48 (8H, m), 7.72 (1H, s), 8.63 (1H, s). |
| 123 | 5 | ESI+: 539 [M + Na]<br>NMR1: 1.59-1.63 (2H, m), 1.74-1.79 (4H, m), 1.89-2.24 (8H, m), 2.83-4.50 (8H, m), 3.59 (3H, m), 7.91 (1H, s), 8.68 (1H, s) |
| 124 | 6 | ESI+: 429 [M + Na]<br>NMR1: 1.20 (3H, d, J = 6.4 Hz), 1.49-1.58 (1H, m), 2.29-2.37 (1H, m), 2.55-2.63 (1H, m), 2.68-2.75 (1H, m), 3.29-3.69 (8H, m), 4.91-4.99 (1H, m), 7.05-7.09 (1H, m), 7.15-7.23 (2H, m), 7.61 (1H, d, J = 7.6 Hz), 8.65 (1H, s) |
| 125 | 6 | ESI+: 407<br>NMR1: 1.91-1.97 (2H, m), 2.26 (3H, s), 2.72 (2H, t, J = 6.4 Hz), 3.29-3.69 (8H, m), 3.97 (2H, t, J = 6.4 Hz), 6.95-7.00 (2H, m), 7.61 (1H, d, J = 8.4 Hz), 8.67 (1H, s) |

TABLE 44

| Ex | Syn | DAT |
|---|---|---|
| 126 | 6 | ESI+: 483 [M + Na]<br>NMR1: 1.96-2.02 (2H, m), 2.85 (2H, t, J = 6.4 Hz), 3.30-3.69 (8H, m), 3.97-4.11 (2H, m), 7.35-7.44 (2H, m), 8.22 (1H, s), 8.79 (1H, s) |
| 127 | 6 | ESI+: 395<br>NMR1: 3.30-3.71 (8H, m), 4.24 (2H, dd, J = 5.6, 4.0 Hz), 4.34 (2H, dd, J = 5.6, 4.0 Hz), 6.88-6.94 (2H, m), 7.02-7.06 (1H, m), 7.97 (1H, dd, J = 8.4, 1.6 Hz), 8.79 (1H, s) |
| 128 | 6 | ESI+: 423<br>NMR1: 1.91-1.97 (2H, m), 2.74 (2H, t, J = 6.4 Hz), 3.30-3.67 (8H, m), 3.74 (3H, s), 3.97 (2H, t, J = 6.4 Hz), 6.73-6.78 (2H, m), 7.62-7.64 (1H, m), 8.65 (1H, s) |
| 129 | 6 | ESI+: 485 [M + Na]<br>NMR1: 1.14-1.28 (3H, m), 1.39-1.59 (2H, m), 2.05-2.20 (2H, m), 2.35-2.39 (1H, m), 2.65-2.71 (1H, m), 2.87-4.49 (9H, m), 7.93-8.16 (1H, m), 8.64-8.70 (1H, m), 11.70-12.12 (1H, br-s) |
| 130 | 6 | ESI+: 497 [M + Na]<br>NMR1: 1.26-1.77 (7H, m), 1.95-2.15 (1H, m), 2.59-2.72 (1H, m), 2.86-4.52 (8H, m), 4.63-4.82 (1H, m), 8.33-8.42 (1H, m), 8.68-8.75 (1H, m) |
| 131 | 6 | ESI+: 443 [M + Na]<br>NMR1: 0.82-0.91 (3H, m), 1.24-1.75 (8H, m), 1.87-2.00 (1H, m), 2.87-4.49 (9H, m), 7.99-8.10 (1H, m), 8.63-8.68 (1H, m) |
| 132 | 6 | ESI+: 483 [M + Na]<br>NMR1: 0.71-0.84 (3H, m), 0.96-1.21 (8H, m), 1.35-1.45 (1H, m), 1.57-1.72 (3H, m), 1.86-1.99 (1H, m), 2.85-4.52 (9H, m), 7.70-7.75 (1H, m), 8.62-8.71 (1H, m) |

TABLE 44-continued

| Ex | Syn | DAT |
|---|---|---|
| 133 | 6 | $[\alpha]_D^{28}$ = +10.0 (c 1.0, MeOH)<br>ESI+: 441 [M + Na]<br>NMR1: 1.07-1.21 (3H, m), 1.38-1.70 (5H, m), 2.17-2.25 (2H, m), 2.84-4.50 (9H, m), 8.11-8.20 (1H, m), 8.65-8.68 (1H, m) |
| 134 | 6 | ESI+: 485 [M + Na]<br>NMR1: 1.40-1.47 (6H, m), 1.89-1.97 (6H, m), 2.92-4.45 (8H, m), 3.03 (2H, d, J = 5.2 Hz), 4.35 (1H, t, J = 5.2 Hz), 7.77 (1H, s), 8.64 (1H, s) |

TABLE 45

| Ex | Syn | DAT |
|---|---|---|
| 135 | 6 | ESI+: 525 [M + Na]<br>NMR1: 0.85 (3H, d, J = 7.2 Hz), 1.02-1.31 (8H, m), 1.40-1.46 (6H, m), 1.90-1.96 (6H, m), 2.88-4.50 (8H, m), 7.76 (1H, s), 8.63 (1H, s) |
| 136 | 6 | ESI+: 441 [M + Na]<br>NMR1: 1.34-1.42 (2H, m), 1.65-1.86 (8H, m), 2.11-2.14 (1H, m), 2.89-4.47 (8H, m), 8.46 (1H, s), 8.66 (1H, s) |
| 137 | 6 | ESI+: 393 [M + Na]<br>NMR1: 1.33-1.43 (2H, m), 1.64-1.85 (8H, m), 2.10-2.14 (1H, m), 3.25-3.69 (8H, m), 8.40 (1H, s), 8.50 (1H, s) |
| 138 | 6 | $[\alpha]_D^{24}$ = −11.9 (c 0.5, MeOH)<br>ESI+: 441 [M + Na]<br>NMR1: 1.07-1.21 (3H, m), 1.38-1.70 (5H, m), 2.17-2.25 (2H, m), 2.84-4.50 (9H, m), 8.10-8.22 (1H, m), 8.65-8.69 (1H, m) |
| 139 | 6 | ESI−: 489<br>NMR1: 1.37-2.22 (13H, m), 2.90-3.97 (8H, m), 4.62 (2H, s), 7.94 (1H, s), 8.66 (1H, s) |
| 140 | 6 | $[\alpha]_D^{26.8}$ = −64.7 (c 1.0, MeOH)<br>ESI+: 441 [M + Na]<br>NMR1: 1.10-1.18 (1H, m), 1.22-1.52 (5H, m), 1.56-1.67 (1H, m), 1.85-1.97 (1H, m), 2.14-2.19 (1H, m), 2.41-2.52 (1H, m), 2.85-4.48 (9H, m), 8.25-8.36 (1H, m), 8.66 (1H, s) |
| 141 | 6 | $[\alpha]_D^{27}$ = +65.6 (c 1.0, MeOH)<br>ESI+: 441 [M + Na]<br>NMR1: 1.09-1.18 (1H, m), 1.22-1.52 (5H, m), 1.56-1.68 (1H, m), 1.84-1.97 (1H, m), 2.14-2.20 (1H, m), 2.41-2.53 (1H, m), 2.83-4.51 (9H, m), 8.25-8.36 (1H, m), 8.66 (1H, s) |
| 142 | 6 | ESI+: 455 [M + Na]<br>NMR1: 1.26-1.72 (10H, m), 1.74-1.87 (1H, m), 1.90-2.20 (1H, m), 2.85-3.45 (4H, m), 3.53-3.97 (3H, m), 3.98-4.05 (1H, m), 4.20-4.45 (1H, m), 8.18-8.32 (1H, m), 8.63-8.68 (1H, m) |

TABLE 46

| Ex | Syn | DAT |
|---|---|---|
| 143 | 9 | ESI+: 433 [M + Na]<br>NMR1: 1.62-1.68 (6H, m), 2.03-2.10 (9H, m), 3.25-3.67 (8H, m), 7.72 (1H, s), 8.48 (1H, s) |
| 144 | 9 | ESI+: 449 [M + Na]<br>NMR1: 1.43-1.59 (6H, m), 1.90-1.99 (6H, m), 2.17 (2H, s), 3.25-3.68 (8H, m), 4.52 (1H, s), 7.80 (1H, s), 8.49 (1H, s) |
| 145 | 10 | ESI+: 411<br>NMR1: 1.60-1.73 (8H, m), 2.00-2.10 (11H, m), 3.28-3.42 (3H, m), 3.89-3.97 (2H, m), 4.06-4.12 (2H, m), 7.71 (1H, s), 8.85 (1H, s), 9.56 (2H, s) |
| 146 | 10 | ESI+: 440<br>NMR1: 1.62-1.69 (6H, m), 2.03-2.10 (9H, m), 3.11-3.25 (2H, m), 3.48-3.59 (6H, m), 3.76-4.05 (4H, m), 4.15-4.21 (2H, m), 7.73 (1H, s), 8.84 (1H, s), 9.95 (1H, s), 11.48 (1H, s) |
| 147 | 10 | ESI+: 371<br>NMR1: 1.60-1.69 (6H, m), 2.03-2.10 (9H, m), 3.01-3.08 (2H, m), 3.68-3.72 (2H, m), 4.09-4.46 (3H, m), 7.69 (1H, s), 8.76 (1H, s), 9.22-9.30 (2H, m) |

TABLE 46-continued

| Ex | Syn | DAT |
|---|---|---|
| 148 | 10 | ESI+: 385<br>NMR1: 1.61-1.69 (6H, m), 2.03-2.09 (9H, m), 3.13-3.20 (2H, m), 3.31 (3H, s), 3.61-3.67 (2H, m), 4.08-4.14 (2H, m), 7.69 (1H, s), 8.75 (1H, s), 9.29-9.40 (2H, m) |
| 149 | 10 | ESI+: 409<br>NMR1: 1.05-1.18 (1H, m), 1.20-1.32 (2H, m), 1.34-1.45 (2H, m), 1.57-1.69 (7H, m), 1.74-1.81 (2H, m), 2.03-2.14 (11H, m), 3.01-3.11 (1H, m), 4.04-4.10 (2H, m), 7.69 (1H, s), 8.85 (1H, s), 9.31-9.39 (2H, m) |
| 150 | 10 | ESI+: 425<br>NMR1: 1.52-1.87 (14H, m), 2.03-2.09 (9H, m), 3.56 (2H, s), 4.10-4.16 (2H, m), 4.70-5.15 (1H, m), 7.68 (1H, s), 8.78 (1H, s), 9.00-9.07 (2H, m) |

TABLE 47

| Ex | Syn | DAT |
|---|---|---|
| 151 | 10 | ESI+: 425<br>NMR1: 1.17-1.28 (2H, m), 1.62-1.74 (8H, m), 1.95-2.09 (10H, m), 2.85-2.91 (2H, m), 3.23-3.31 (2H, m), 3.82-3.88 (2H, m), 4.05-4.10 (2H, m), 7.70 (1H, s), 8.83 (1H, s), 9.29-9.38 (2H, m) |
| 152 | 10 | ESI+: 411<br>NMR1: 1.25-1.69 (8H, m), 1.78-1.93 (2H, m), 2.03-2.09 (9H, m), 2.59-3.31 (4H, m), 3.89-4.32 (3H, m), 4.82-5.00 (1H, m), 7.75-7.83 (1H, m), 8.78-9.02 (1H, m), 9.34-11.00 (1H, m) |
| 153 | 10 | ESI+: 411<br>NMR1: 1.62-1.84 (8H, m), 1.87-2.09 (11H, m), 2.95-3.22 (3H, m), 3.32-3.38 (1H, m), 3.61-3.95 (1H, m), 4.16-4.26 (2H, m), 4.33-4.58 (1H, m), 7.77 (1H, s), 9.00 (1H, s), 10.57-10.73 (1H, m) |
| 154 | 10 | ESI+: 473<br>NMR1: 1.61-1.70 (6H, m), 2.03-2.10 (9H, m), 3.17-3.29 (2H, m), 3.39-3.46 (1H, m), 3.56-3.62 (1H, m), 4.06-4.16 (2H, m), 4.28-4.41 (2H, m), 4.99-5.04 (1H, m), 7.35-7.45 (5H, m), 7.77 (1H, s), 9.03 (1H, s), 11.53 (1H, m) |
| 155 | 10 | ESI+: 399<br>NMR1: 1.30 (3H, d, J = 6.4 Hz), 1.62-1.68 (6H, m), 2.03-2.09 (9H, m), 3.32 (3H, s), 3.44-3.62 (3H, m), 4.09-4.15 (2H, m), 7.68 (1H, s), 8.81 (1H, s), 9.14-9.24 (1H, m), 9.40-9.50 (1H, m) |
| 156 | 10 | ESI+: 421<br>NMR1: 1.08-1.23 (3H, m), 1.40-1.75 (10H, m), 1.79-1.85 (1H, m), 2.03-2.09 (9H, m), 2.29-2.32 (1H, m), 2.55-2.58 (1H, m), 3.06-3.14 (1H, m), 3.99-4.07 (2H, m), 7.70 (1H, s), 8.85 (1H, s), 9.18-9.27 (2H, m) |
| 157 | 10 | ESI+: 379<br>NMR1: 1.92-2.00 (2H, m), 2.77 (2H, t, J = 6.6 Hz), 3.10-3.26 (2H, m), 3.32-3.47 (2H, m), 3.76-4.04 (6H, m), 4.41 (2H, s), 7.06 (1H, t, J = 7.0 Hz), 7.13-7.22 (2H, m), 7.74 (1H, d, J = 7.3 Hz), 9.15 (1H, s), 11.08 (1H, br-s) |

TABLE 48

| Ex | Syn | DAT |
|---|---|---|
| 158 | 10 | ESI+: 449 [M + Na]<br>NMR1: 1.91-1.99 (2H, m), 2.76 (2H, t, J = 6.5 Hz), 3.02-3.25 (2H, m), 3.82-4.65 (10H, m), 7.01-7.06 (1H, m), 7.12-7.20 (2H, m), 7.72-7.75 (1H, m), 8.92 (1H, s) |
| 159 | 10 | ESI+: 427 [M + Na]<br>NMR1: 1.05-1.22 (3H, m), 1.38-1.56 (4H, m), 1.60-1.69 (1H, m), 2.15-2.25 (2H, m), 3.20-3.80 (9H, m), 4.00-4.40 (2H, br-s), 7.95-8.15 (1H, br-s), 8.80-9.00 (1H, br-s) |
| 160 | 10 | ESI+: 413<br>NMR1: 1.05-1.20 (3H, m), 1.38-1.55 (4H, m), 1.59-1.68 (1H, m), 2.15-2.23 (2H, m), 3.14-3.25 (4H, m), 3.58-3.72 (3H, m), 7.74-7.90 (1H, br-s), 8.43-8.54 (1H, br-s) |

TABLE 48-continued

| Ex | Syn | DAT |
|---|---|---|
| 161 | 10 | ESI+: 391<br>NMR1: 1.06-1.23 (3H, m), 1.38-1.57 (4H, m), 1.60-1.70 (1H, m), 2.16-2.25 (2H, m), 2.27-2.40 (2H, m), 3.15-3.30 (2H, m), 3.50-3.74 (3H, m), 4.30-4.44 (4H, m), 8.12-8.22 (1H, m), 8.91-9.01 (1H, m), 11.02 (1H, br-s) |
| 162 | 11 | ESI+: 425<br>NMR1: 1.12 (6H, d, J = 6.4 Hz), 1.61-1.69 (6H, m), 2.02-2.10 (9H, m), 2.64-2.74 (2H, m), 3.33-3.43 (2H, m), 4.00-4.10 (2H, m), 4.22-4.29 (2H, m), 7.77 (1H, s), 9.01 (1H, s), 11.45 (1H, s) |
| 163 | 11 | ESI+: 395<br>NMR1: 1.32-1.45 (1H, m), 1.59-1.91 (11H, m), 2.02-2.11 (9H, m), 2.86-2.99 (2H, m), 3.31-3.39 (2H, m), 4.17-4.23 (2H, m), 7.76 (1H, s), 8.99 (1H, s), 10.50 (1H, s) |
| 164 | 11 | ESI+: 431<br>NMR1: 1.61-1.68 (6H, m), 1.87-1.99 (4H, m), 2.02-2.08 (9H, m), 2.44-2.52 (4H, m), 3.45-3.48 (2H, m), 7.31 (1H, s), 8.51 (1H, s) |
| 165 | 11 | ESI+: 425<br>NMR1: 1.22 (6H, d, J = 6.4 Hz), 1.62-1.68 (6H, m), 2.03-2.09 (9H, m), 3.52-3.62 (2H, m), 3.73-3.90 (4H, m), 4.52-4.56 (2H, m), 7.73 (1H, s), 9.07 (1H, s), 11.02-11.39 (1H, m) |

TABLE 49

| Ex | Syn | DAT |
|---|---|---|
| 166 | 11 | ESI+: 467 [M + Na]<br>NMR1: 1.62-1.66 (6H, m), 2.02-2.08 (9H, m), 2.84-2.89 (4H, m), 3.07-3.11 (4H, m), 3.58 (2H, s), 7.33 (1H, s), 8.55 (1H, s) |
| 167 | 17 | ESI−: 415<br>NMR1: 1.57 (2H, br-s), 1.81-1.97 (2H, m), 3.39-3.53 (2H, m), 3.82 (2H, br-s), 4.74-4.86 (1H, m), 7.06 (1H, ddd, J = 0.8, 2, 8 Hz), 7.35 (1H, t, J = 8.2 Hz), 7.65 (1H, ddd, J = 0.8, 2, 8 Hz), 7.95 (1H, t, J = 2.2 Hz), 8.73 (1H, s), 9.28 (1H, br-s), 10.44 (1H, s) |
| 168 | 19 | ESI+: 410<br>NMR1: 3.71 (3H, s), 5.07 (2H, br-s), 6.86-6.91 (2H, m), 6.94-7.0 (2H, m), 7.07 (1H, ddd, J = 0.8, 2, 8 Hz), 7.35 (1H, t, J = 8.2 Hz), 7.67 (1H, ddd, J = 0.8, 2, 8 Hz), 7.98 (1H, t, J = 2.2 Hz), 8.93 (1H, s), 10.49 (1H, br-s) |
| 169 | 20 | ESI+: 416 [M + Na]<br>NMR1: 4.53 (2H, d, J = 4.4 Hz), 5.29 (2H, s), 5.4 (1H, t, J = 5.4 Hz), 7.19-7.32 (7H, m), 7.39 (1H, t, J = 8 Hz), 7.45 (1H, t, J = 2 Hz), 8.7 (1H, s) |
| 170 | 21 | ESI+: 394 [M + Na]<br>NMR1: 1.05-1.20 (3H, m), 1.40-1.58 (4H, m), 1.73-1.81 (1H, m), 2.28-2.35 (2H, m), 3.65-3.75 (4H, m), 3.75-3.90 (4H, m), 4.72-4.76 (1H, m), 8.93 (1H, s) |

TABLE 50

[Structure: thiomorpholine-1,1-dioxide carbonyl attached to 4-(trifluoromethyl)pyrimidine with —W—R³ at 2-position]

| Ex | —W—R³ |
|---|---|
| C001 | [cyclopropyl-NH-methyl] |

TABLE 50-continued

[Structure: thiomorpholine-1,1-dioxide carbonyl attached to 4-(trifluoromethyl)pyrimidine with —W—R³ at 2-position]

| Ex | —W—R³ |
|---|---|
| C002 | [2,2-dimethylbicyclic structure with CH₂NHCH₃, Chiral] |
| C003 | [cyclopentyl-NH-methyl] |
| C004 | [cyclohexyl-NH-methyl] |
| C005 | [1-ethynylcyclohexyl-NH-methyl] |
| C006 | [cyclohexylmethyl-NH-methyl] |
| C007 | [1,2,3,4-tetrahydronaphthalen-1-yl-NH-methyl] |
| C008 | [N-methyl-N-(2-cyanoethyl)amino methyl] |
| C009 | [N-methyl-N-(2-hydroxyethyl)amino methyl] |
| C010 | [N-methyl-N-(3-(2-oxopyrrolidin-1-yl)propyl)amino] |
| C011 | [furan-2-ylmethyl-NH-methyl] |

TABLE 50-continued
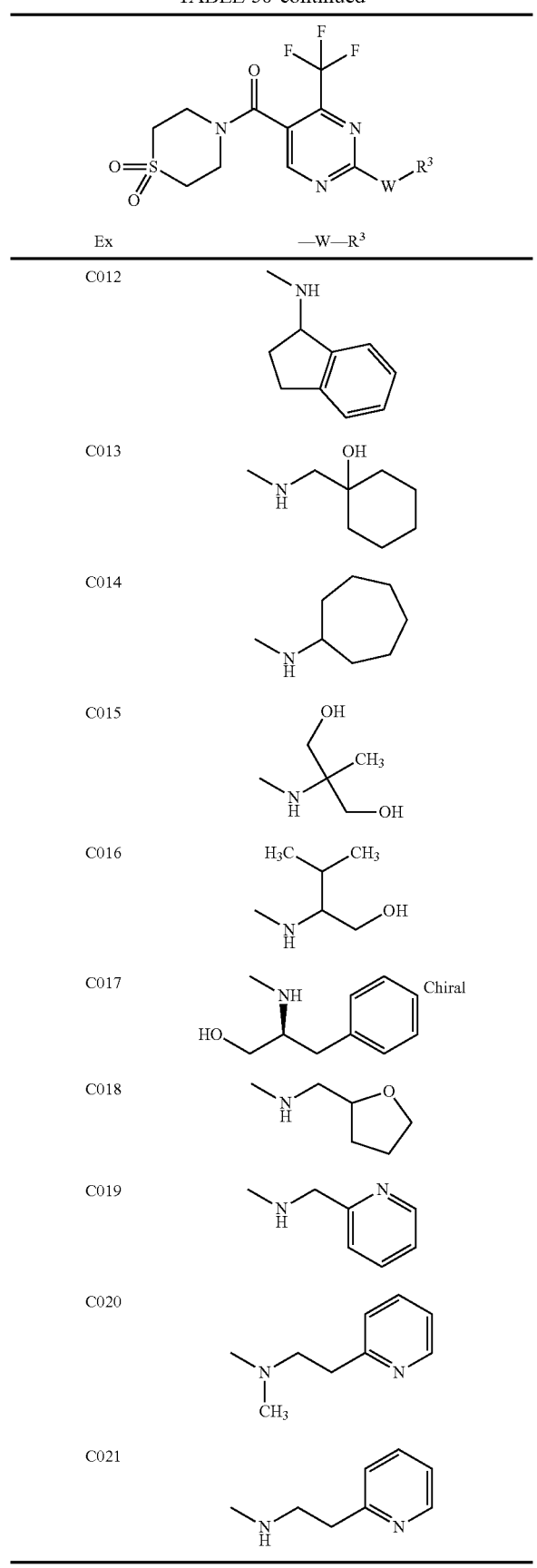
TABLE 51
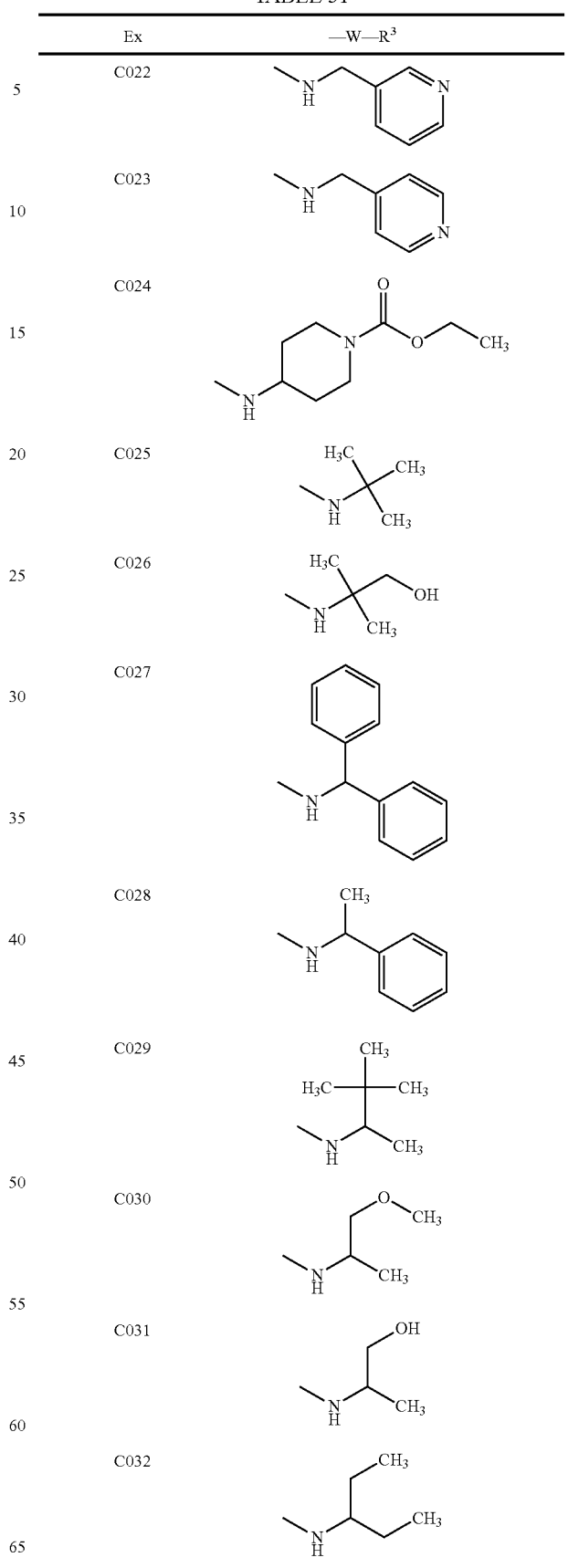

TABLE 51-continued
| Ex | —W—R³ |
|---|---|
| C033 | 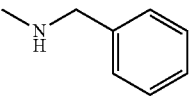 |
| C034 | 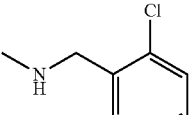 |
| C035 | 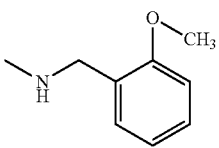 |
| C036 | 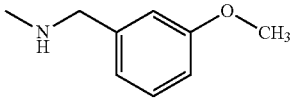 |
| C037 | 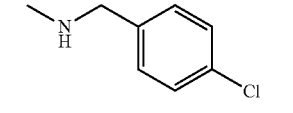 |
| C038 | 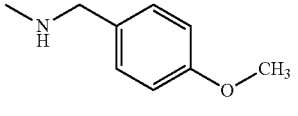 |
| C039 | 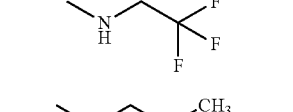 |
| C040 | 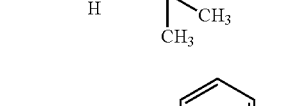 |
| C041 | 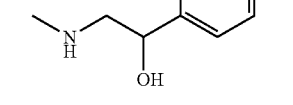 |
| C042 | 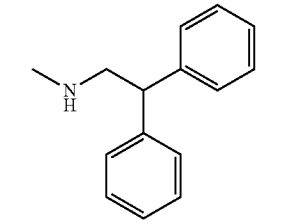 |
| C043 | 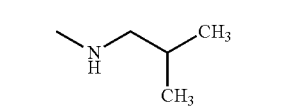 |
| C044 | 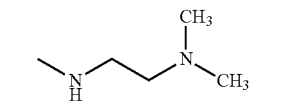 |
| C045 | 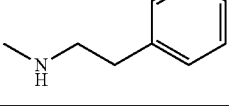 |
TABLE 52
| Ex | —W—R³ |
|---|---|
| C046 | 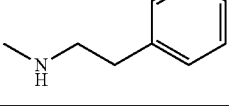 |
| C047 | 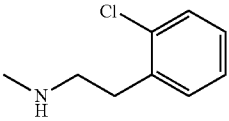 |
| C048 | 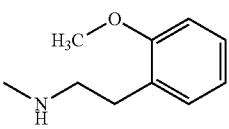 |
| C049 | 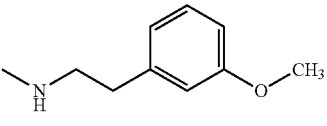 |
| C050 | 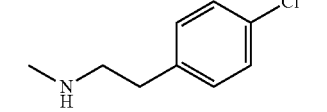 |
| C051 | 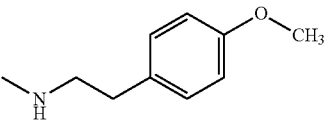 |
| C052 | 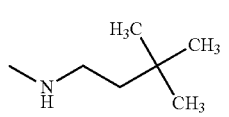 |
| C053 | 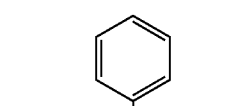 |
| C054 | 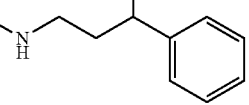 |
| C055 | 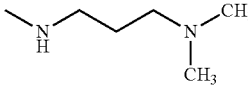 |

TABLE 52-continued
| Ex | —W—R³ |
|---|---|
| C056 | 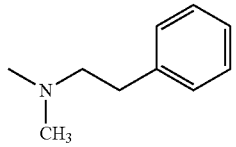 |
| C057 | 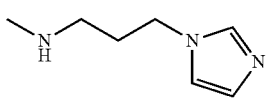 |
| C058 | 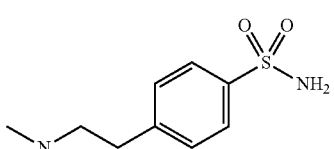 |
| C059 | 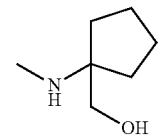 |
| C060 | 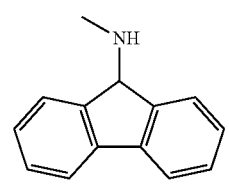 |
| C061 | 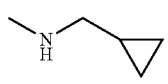 |
| C062 | 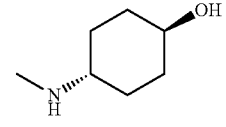 |
| C063 | 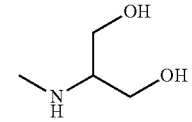 |
| C064 | 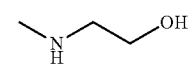 |
| C065 | 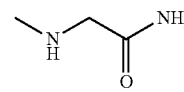 |
| C066 | 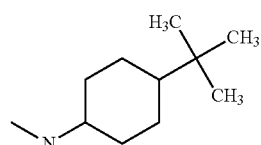 |
| C067 | 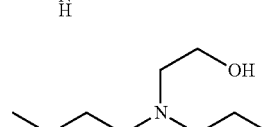 |
TABLE 52-continued
| Ex | —W—R³ |
|---|---|
| C068 | 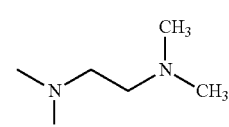 |
| C069 | 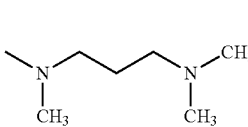 |
TABLE 53
| Ex | —W—R³ |
|---|---|
| C070 | 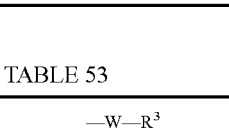 |
| C071 | 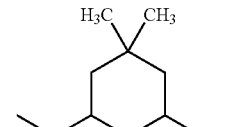 |
| C072 |  |
| C073 | Chiral 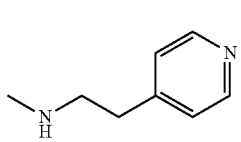 |
| C074 | Chiral 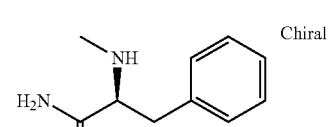 |
| C075 | 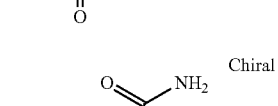 |
| C076 | 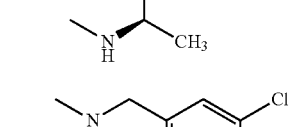 |
| C077 | 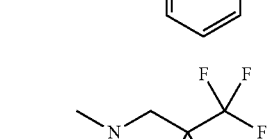 |

TABLE 53-continued
| Ex | —W—R³ |
|---|---|
| C078 | 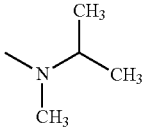 |
| C079 | 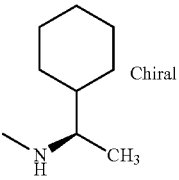 Chiral |
| C080 | 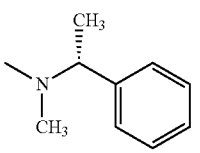 Chiral |
| C081 | 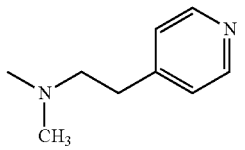 |
| C082 | 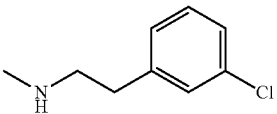 |
| C083 | 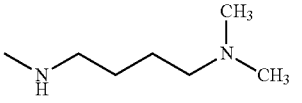 |
| C084 | 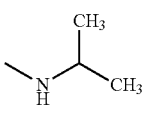 |
| C085 | 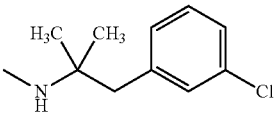 |
| C086 | 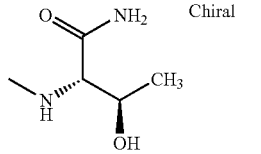 Chiral |
| C087 | 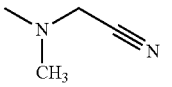 |
| C088 | 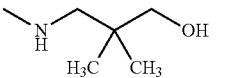 |
| C089 | 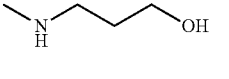 |
| C090 | 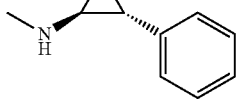 |
| C091 | 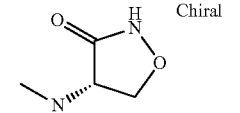 Chiral |
| C092 | 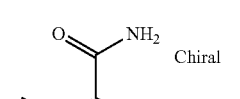 Chiral |
TABLE 54
| Ex | —W—R³ |
|---|---|
| C093 | 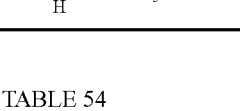 Chiral |
| C094 | 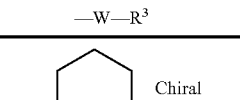 Chiral |
| C095 | 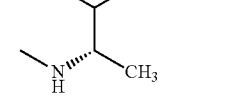 |
| C096 | 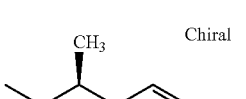 |
| C097 | 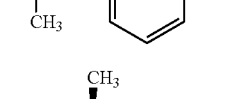 |
| C098 | 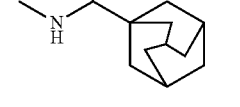 Chiral |

TABLE 54-continued
| Ex | —W—R³ |
|---|---|
| C099 | 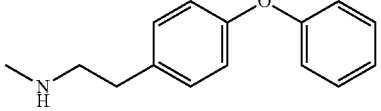 |
| C100 | 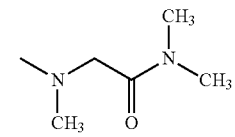 |
| C101 | 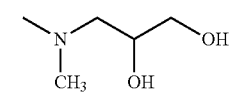 |
| C102 | 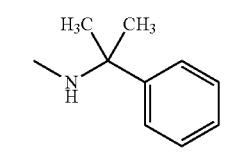 |
| C103 | 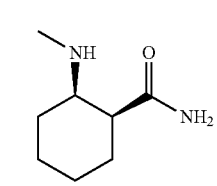 |
| C104 | 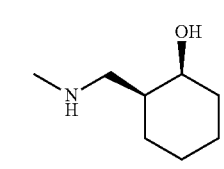 |
| C105 | 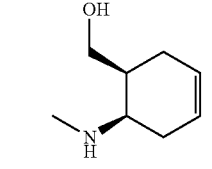 |
| C106 | 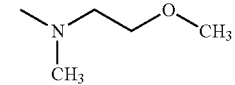 |
| C107 | 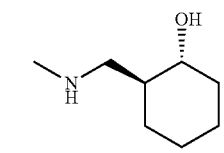 |
| C108 | 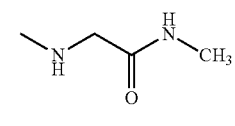 |
| C109 | 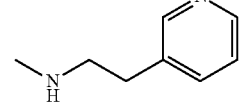 |
TABLE 54-continued
| Ex | —W—R³ |
|---|---|
| C110 | 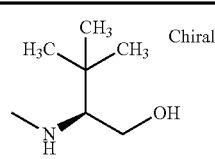 Chiral |
| C111 | 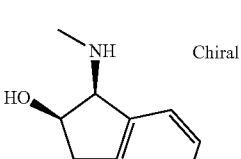 Chiral |
| C112 | 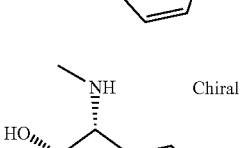 Chiral |
| C113 | 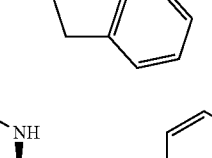 Chiral |
| C114 | 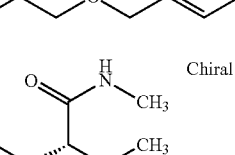 Chiral |
TABLE 55
| Ex | —W—R³ |
|---|---|
| C115 | 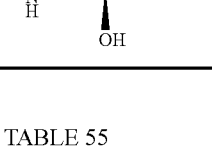 |
| C116 | 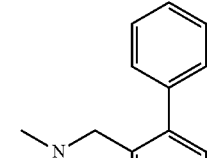 |
| C117 | 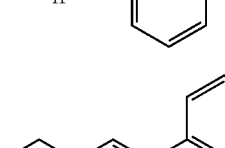 Chiral |

TABLE 55-continued
| Ex | —W—R³ |
|---|---|
| C118 | 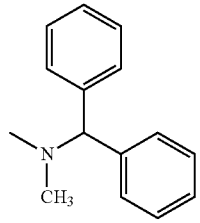 |
| C119 | 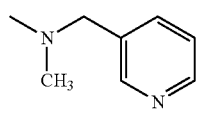 |
| C120 | 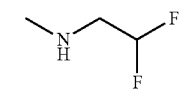 |
| C121 | 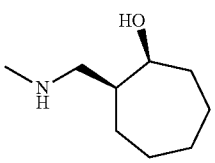 |
| C122 | 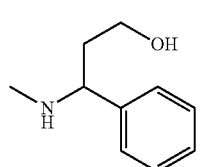 |
| C123 | 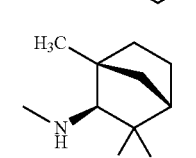 |
| C124 | 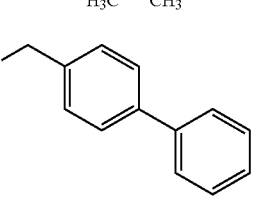 |
| C125 | 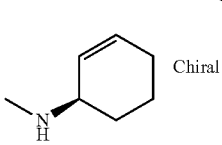 Chiral |
| C126 | 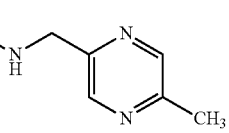 |
| C127 | 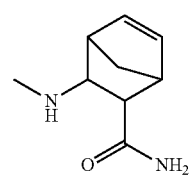 |
| C128 | 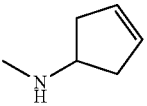 |
| C129 | 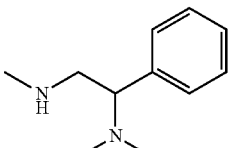 |
| C130 | 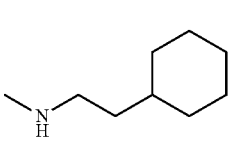 |
| C131 | 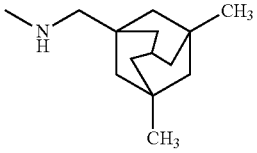 |
| C132 | 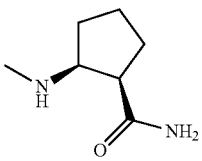 |
| C133 | 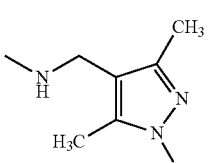 |
| C134 | 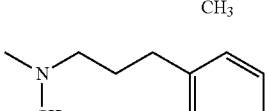 |
| C135 | 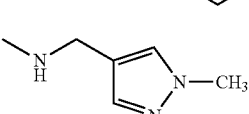 |
TABLE 56
| Ex | —W—R³ |
|---|---|
| C136 | 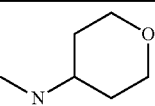 |
| C137 | 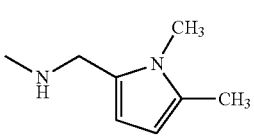 |

TABLE 56-continued
| Ex | —W—R³ |
|---|---|
| C138 | 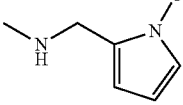 |
| C139 | 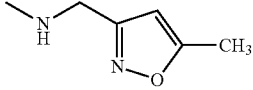 |
| C140 | 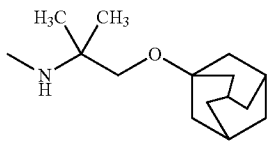 |
| C141 | 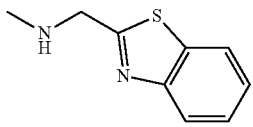 |
| C142 | 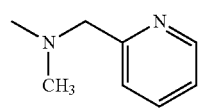 |
| C143 | 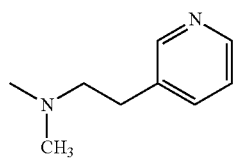 |
| C144 | 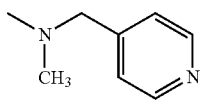 |
| C145 | 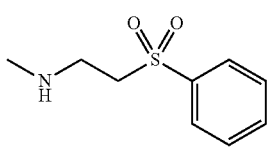 |
| C146 | 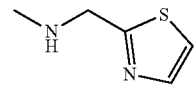 |
| C147 | 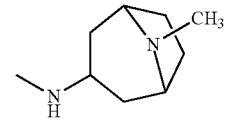 |
| C148 | 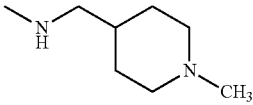 |
| C149 | 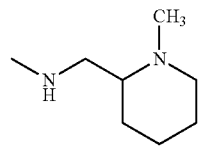 |
TABLE 56-continued
| Ex | —W—R³ |
|---|---|
| C150 | 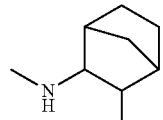 |
| C151 | 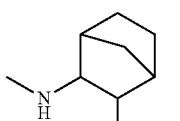 |
| C152 | 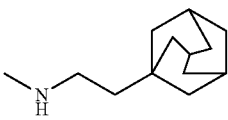 |
| C153 | 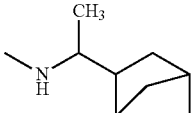 |
| C154 | 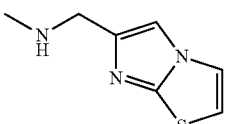 |
| C155 | 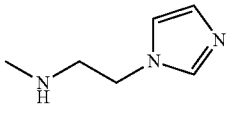 |
| C156 | 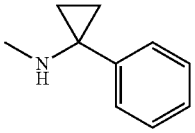 |
| C157 | 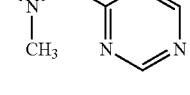 |
| C158 | 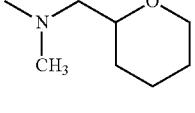 |
| C159 | 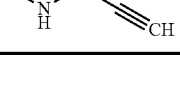 |
TABLE 57
| Ex | —W—R³ |
|---|---|
| C160 | 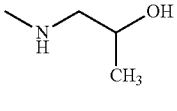 |

TABLE 57-continued

| Ex | —W—R³ |
|---|---|
| C161 | NH-CH₂-CH(OH)-CH₂OH |
| C162 | CH₃NH-CH₂-C(CH₃)₂-CH₂-N(CH₃)₂ |
| C163 | CH₃NH-CH₂CH₂-O-CH₃ |
| C164 | CH₃NH-CH₂CH₂CH₂-O-CH₃ |
| C165 | N-methylamino-(2-methylcyclohexyl) |
| C166 | N-methyl-N-cyclohexylamino |
| C167 | 1-methyl-4-(methylamino)piperidine |
| C168 | CH₃-N(CH₃)-CH₂CH₂-O-phenyl |
| C169 | CH₃NH-CH(Ph)-CH₂-N(CH₃)₂ |
| C170 | (CH₃)₂N-CH₂CH₂CH₂CH₂-phenyl |
| C171 | CH₃NH-CH₂CH₂-SO₂-CH₃ |
| C172 | CH₃NH-CH₂CH₂CH₂-SO₂-phenyl |

TABLE 57-continued

| Ex | —W—R³ |
|---|---|
| C173 | CH₃NH-CH₂-CH(OH)-CH₂-phenyl |
| C174 | 2-chlorobenzyl-N,N-dimethylamine |
| C175 | 4-chlorobenzyl-N,N-dimethylamine |
| C176 | 3-(methylamino)tetrahydrothiophene-1,1-dioxide |
| C177 | CH₃NH-CH₂-(benzothiophen-2-yl) |
| C178 | CH₃NH-CH₂-(benzothiophen-3-yl) |
| C179 | CH₃NH-CH₂CH₂-(4-benzylpiperidin-1-yl) |
| C180 | 4-methoxybenzyl-N,N-dimethylamine |
| C181 | CH₃NH-C(CH₃)₂-CH₂-(pyrrolidin-1-yl) |
| C182 | CH₃NH-CH₂-CH(OH)-CF₃ (Chiral) |

TABLE 58

| Ex | —W—R³ |
|---|---|
| C183 | (structure) |
| C184 | (structure) |
| C185 | (structure) Chiral |
| C186 | (structure) Chiral |
| C187 | (structure) |
| C188 | (structure) |
| C189 | (structure) |
| C190 | (structure) Chiral |
| C191 | (structure) Chiral |

TABLE 58-continued

| Ex | —W—R³ |
|---|---|
| C192 | (structure) |
| C193 | (structure) |
| C194 | (structure) Chiral |
| C195 | (structure) Chiral |
| C196 | (structure) Chiral |
| C197 | (structure) Chiral |
| C198 | (structure) |
| C199 | (structure) Chiral |
| C200 | (structure) |
| C201 | (structure) |
| C202 | (structure) |

TABLE 58-continued

| Ex | —W—R³ |
|---|---|
| C203 | (N-methyl-N-phenyl-N'-methylpropane-1,3-diamine) |

TABLE 59

| Ex | —W—R³ |
|---|---|
| C204 | Chiral; N-methyl-2-(methylamino)-3,3-dimethylbutanamide |
| C205 | Chiral; 1-(methylamino)-hexane-2,3,4,5,6-pentaol |
| C206 | (1,3-dioxan-2-ylmethyl)methylamine |
| C207 | N-methyl-(1-isopropylpyrrolidin-2-yl)methanamine |
| C208 | 6-(methylamino)cyclohex-3-ene-1-carboxamide |
| C209 | 6-(methylamino)cyclohex-3-ene-1-carboxamide (stereoisomer) |
| C210 | (oxazol-2-ylmethyl)methylamine |
| C211 | Chiral; 2-(methylamino)-3,3-dimethylbutan-1-ol |

TABLE 59-continued

| Ex | —W—R³ |
|---|---|
| C212 | 4-((methylamino)methyl)benzenesulfonamide |
| C213 | N-methyl-2-fluoroethanamine |
| C214 | N-methyl-1,2,3,4-tetrahydronaphthalen-2-amine |
| C215 | N-methyl-(2,3-dihydro-1H-inden-2-yl)methanamine |
| C216 | N-cyclopentyl-N-methylmethanamine (N,N-dimethylcyclopentanamine) |
| C217 | N-methyl-((4-methylmorpholin-2-yl)methyl)amine |
| C218 | (2-(methylamino)cyclohexyl)methanol |
| C219 | 2-(methylamino)-2-phenylethanol |
| C220 | (3-(methylamino)bicyclo[2.2.1]hept-5-en-2-yl)methanol |
| C221 | 4-(methylamino)butan-2-ol |
| C222 | (2-(methylamino)cyclohexyl)methanol (stereoisomer) |

TABLE 59-continued
| Ex | —W—R³ |
|---|---|
| C223 | 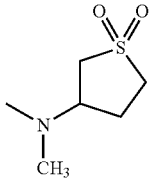 |
| C224 | 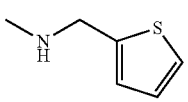 |
| C225 | 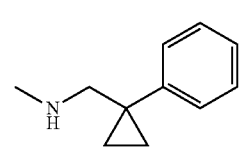 |
| C226 |  |
TABLE 60
| Ex | —W—R³ |
|---|---|
| C227 | 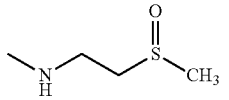 |
| C228 | 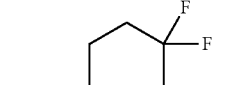 |
| C229 |  |
| C230 | 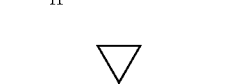 |
| C231 | 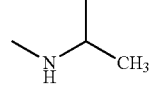 |
| C232 | 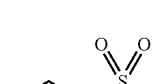 |
TABLE 60-continued
| Ex | —W—R³ |
|---|---|
| C233 | 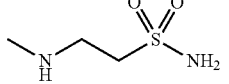 |
| C234 | 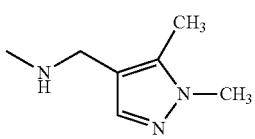 |
| C235 | 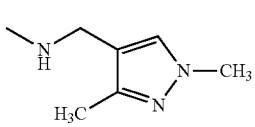 |
| C236 | 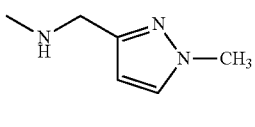 |
| C237 | 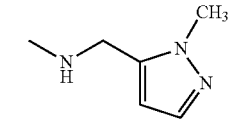 |
| C238 | 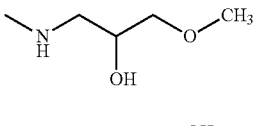 |
| C239 | 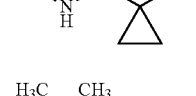 |
| C240 | 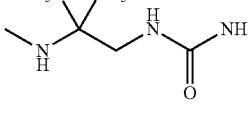 |
| C241 | |
| C242 | |
| C243 | |
| C244 | |

TABLE 60-continued
| Ex | —W—R³ |
|---|---|
| C245 | 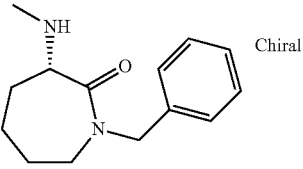 Chiral |
| C246 | 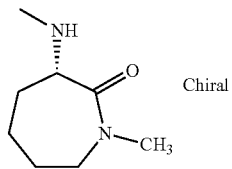 Chiral |
| C247 | 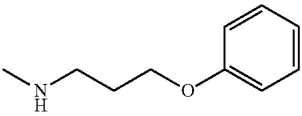 |
| C248 | 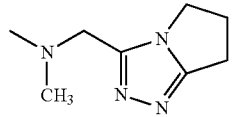 |
| C249 | 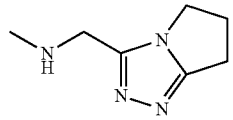 |
TABLE 61
| Ex | —W—R³ |
|---|---|
| C250 | 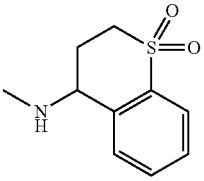 |
| C251 | 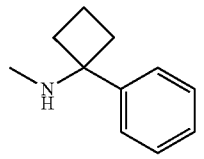 |
| C252 | 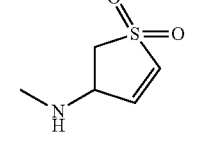 |
| C253 | 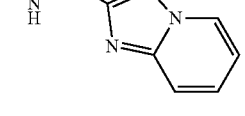 |
TABLE 61-continued
| Ex | —W—R³ |
|---|---|
| C254 | 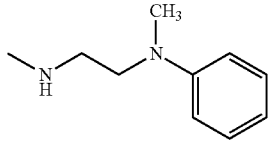 |
| C255 | 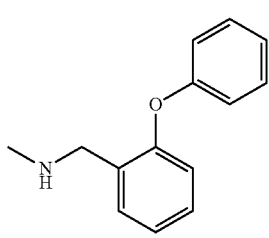 |
| C256 | 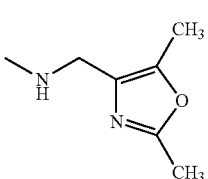 |
| C257 | 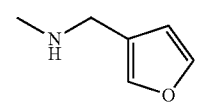 |
| C258 | 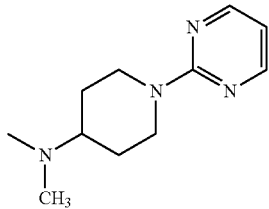 |
| C259 | 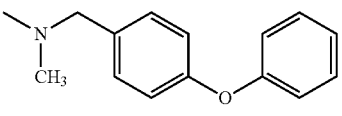 |
| C260 | 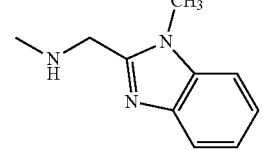 |
| C261 | 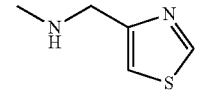 |
| C262 | 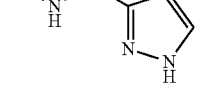 |
| C263 | 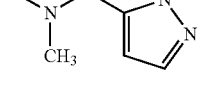 |

TABLE 61-continued
| Ex | —W—R³ |
|---|---|
| C264 |  |
| C265 | 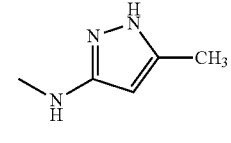 |
| C266 | 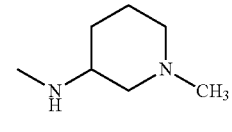 |
| C267 | 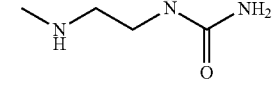 |
| C268 | 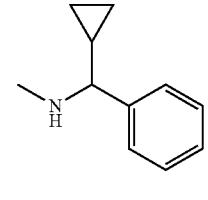 |
| C269 | 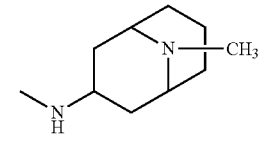 |
| C270 | 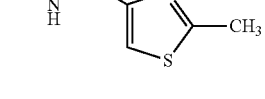 |
| C271 |  |
TABLE 62
| Ex | —W—R³ |
|---|---|
| C272 | 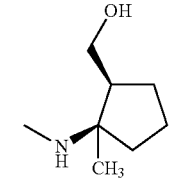 |
| C273 | 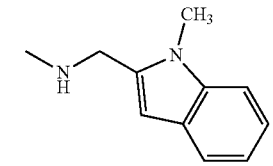 |
TABLE 62-continued
| Ex | —W—R³ |
|---|---|
| C274 | 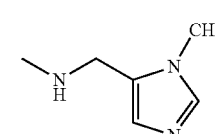 |
| C275 | 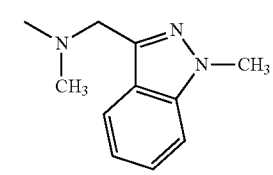 |
| C276 | 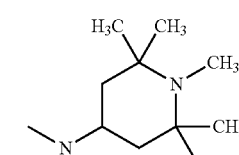 |
| C277 | 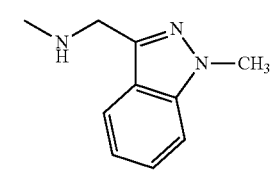 |
| C278 | 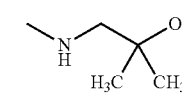 |
| C279 | 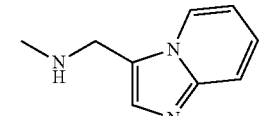 |
| C280 | 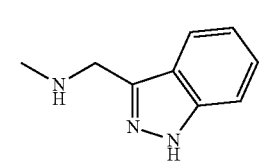 |
| C281 | 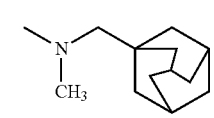 |
| C282 |  |
| C283 |  |

TABLE 62-continued

| Ex | —W—R³ |
|---|---|
| C284 | (S)-N-methyl-1-([1,2,4]triazolo[4,3-a]pyridin-3-yl)ethylamine, Chiral |
| C285 | N-methyl-(5,6-dihydro-4H-cyclopenta[b]thiophen-2-yl)methylamine |
| C286 | (2-(methylamino)-2-methylcyclohexyl)methanol with N,N-dimethyl |
| C287 | N-methyl-N-cycloheptylamine (N,N-dimethyl cycloheptanamine) |
| C288 | (R)-N-methyl-2,2,2-trifluoro-1-phenylethylamine, Chiral |
| C289 | N-methyl-(thieno[3,2-b]thiophen-2-yl)methylamine |
| C290 | N-methyl-(1-methylpiperidin-4-yl)methylamine |
| C291 | N-methyl-(3,5-dimethyl-1H-pyrazol-4-yl)methylamine |

TABLE 63

| Ex | —W—R³ |
|---|---|
| C292 | N-methyl-(5,7-dimethyl-[1,2,4]triazolo[4,3-a]pyrimidin-3-yl)methylamine |

TABLE 63-continued

| Ex | —W—R³ |
|---|---|
| C293 | N-methyl-1-(5-methyl-1,2,4-oxadiazol-3-yl)cyclohexylamine |
| C294 | N-methyl-(benzo[d]oxazol-2-yl)methylamine |
| C295 | N-methyl-(1H-benzo[d]imidazol-2-yl)methylamine |
| C296 | N-methyl-1-(1H-benzo[d]imidazol-2-yl)-2-methylpropylamine |
| C297 | N-methyl-2-(1H-indol-3-yl)-1,1-dimethylethylamine |
| C298 | N-methyl-(1H-imidazol-2-yl)methylamine |
| C299 | N,N-dimethyl-(1H-indol-2-yl)methylamine |
| C300 | N-methyl-N'-acetylethylenediamine |
| C301 | N-methyl-((1-acetamidocyclopentyl)methyl)amine |
| C302 | N-methyl-N-methylglycine (sarcosine) |

TABLE 63-continued
| Ex | —W—R³ |
|---|---|
| C303 | 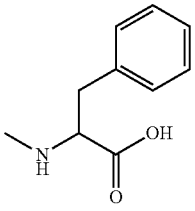 |
| C304 | 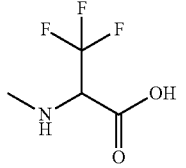 |
| C305 | 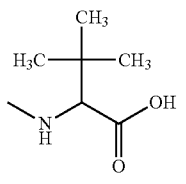 |
| C306 | 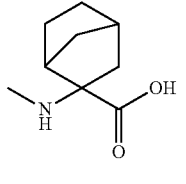 |
| C307 | 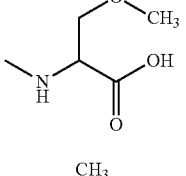 |
| C308 | 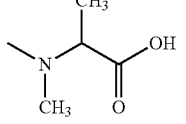 |
| C309 | 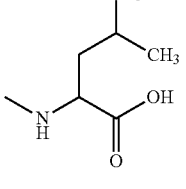 |
| C310 | 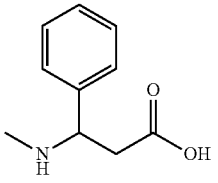 |
| C311 | 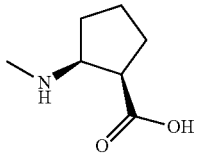 |
| C312 | 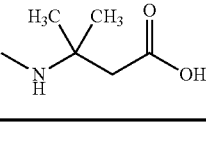 |
TABLE 64
| Ex | —W—R³ |
|---|---|
| C313 | 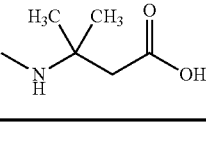 |
| C314 | 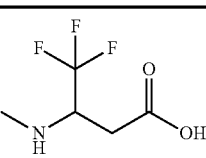 |
| C315 | 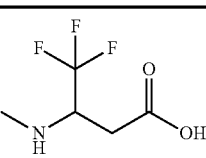 |
| C316 | 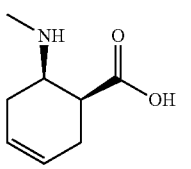 |
| C317 | 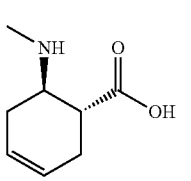 |
| C318 | 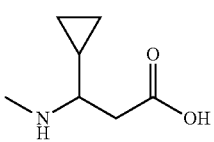 |
| C319 | 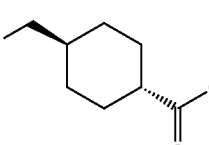 |
| C320 | 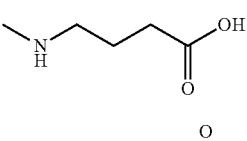 |

TABLE 64-continued

| Ex | —W—R³ |
|---|---|
| C321 | 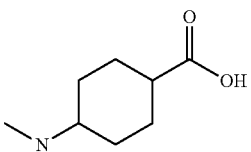 |
| C322 | 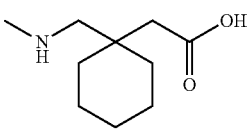 |
| C323 | 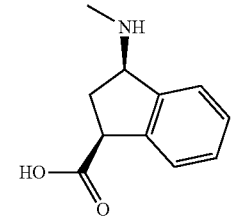 |
| C324 | 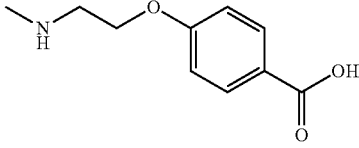 |
| C325 | 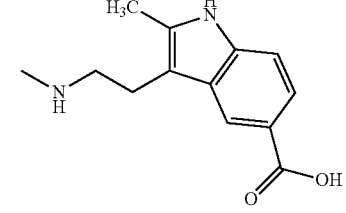 |
| C326 | 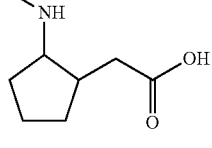 |
| C327 | 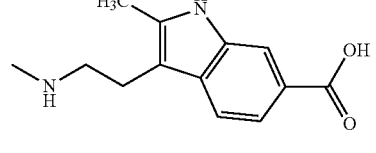 |
| C328 | 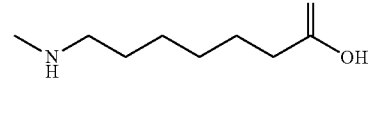 |
| C329 | 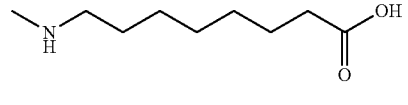 |
| C330 | 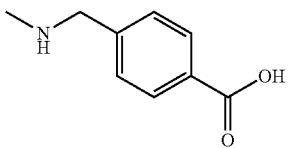 |
| C331 | 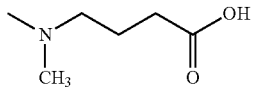 |
| C332 | 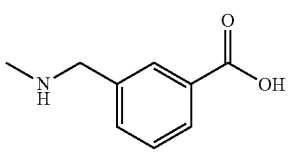 |
| C333 | 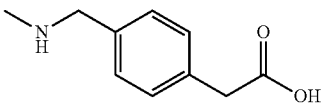 |
| C334 | 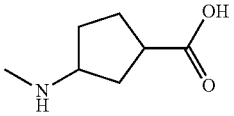 |

TABLE 65

| Ex | DAT | |
|---|---|---|
| C001 | RT: 1.8 | ESI+: 365 |
| C002 | RT: 2.99 | ESI+: 461 |
| C003 | RT: 2.4 | ESI+: 393 |
| C004 | RT: 2.55 | ESI+: 407 |
| C005 | RT: 2.53 | ESI+: 431 |
| C006 | RT: 2.72 | ESI+: 421 |
| C007 | RT: 2.75 | ESI+: 455 |
| C008 | RT: 1.72 | ESI+: 392 |
| C009 | RT: 1.66 | ESI+: 383 |
| C010 | RT: 1.79 | ESI+: 450 |
| C011 | RT: 2.11 | ESI+: 405 |
| C012 | RT: 2.63 | ESI+: 441 |
| C013 | RT: 2.32 | ESI+: 437 |
| C014 | RT: 2.72 | ESI+: 421 |
| C015 | RT: 1.5 | ESI+: 413 |
| C016 | RT: 2.04 | ESI+: 411 |
| C017 | RT: 2.25 | ESI+: 459 |
| C018 | RT: 1.95 | ESI+: 409 |
| C019 | RT: 1.24 | ESI+: 416 |
| C020 | RT: 1.36 | ESI+: 444 |
| C021 | RT: 1.11 | ESI+: 430 |
| C022 | RT: 1.08 | ESI+: 416 |
| C023 | RT: 0.98 | ESI+: 416 |
| C024 | RT: 2.28 | ESI+: 480 |
| C025 | RT: 2.4 | ESI+: 381 |
| C026 | RT: 1.92 | ESI+: 397 |
| C027 | RT: 2.78 | ESI+: 491 |
| C028 | RT: 2.49 | ESI+: 429 |
| C029 | RT: 2.62 | ESI+: 409 |
| C030 | RT: 1.97 | ESI+: 397 |
| C031 | RT: 1.58 | ESI+: 383 |
| C032 | RT: 2.49 | ESI+: 395 |
| C033 | RT: 2.36 | ESI+: 415 |
| C034 | RT: 2.53 | ESI+: 449 |
| C035 | RT: 2.46 | ESI+: 445 |
| C036 | RT: 2.37 | ESI+: 445 |
| C037 | RT: 2.58 | ESI+: 449 |
| C038 | RT: 2.37 | ESI+: 445 |
| C039 | RT: 1.99 | ESI+: 407 |

TABLE 65-continued

| Ex | DAT | |
|---|---|---|
| C040 | RT: 2.5 | ESI+: 395 |
| C041 | RT: 2.16 | ESI+: 445 |
| C042 | RT: 2.81 | ESI+: 505 |
| C043 | RT: 2.31 | ESI+: 381 |
| C044 | RT: 0.81 | ESI+: 396 |
| C045 | RT: 2.49 | ESI+: 429 |
| C046 | RT: 2.65 | ESI+: 463 |
| C047 | RT: 2.56 | ESI+: 459 |
| C048 | RT: 2.48 | ESI+: 459 |
| C049 | RT: 2.68 | ESI+: 463 |
| C050 | RT: 2.47 | ESI+: 459 |
| C051 | RT: 2.67 | ESI+: 409 |
| C052 | RT: 2.88 | ESI+: 519 |
| C053 | RT: 0.89 | ESI+: 410 |
| C054 | RT: 2.63 | ESI+: 443 |
| C055 | RT: 2.62 | ESI+: 429 |
| C056 | RT: 2.71 | ESI+: 443 |
| C057 | RT: 0.99 | ESI+: 433 |
| C058 | RT: 1.82 | ESI+: 508 |
| C059 | RT: 2.21 | ESI+: 423 |
| C060 | RT: 2.86 | ESI+: 489 |
| C061 | RT: 2.17 | ESI+: 379 |
| C062 | RT: 1.65 | ESI+: 423 |
| C063 | RT: 1.16 | ESI+: 399 |
| C064 | RT: 1.35 | ESI+: 369 |
| C065 | RT: 1.05 | ESI+: 382 |
| C066 | RT: 3.06 | ESI+: 463 |
| C067 | RT: 0.79 | ESI+: 456 |
| C068 | RT: 0.96 | ESI+: 410 |
| C069 | RT: 1.11 | ESI+: 424 |
| C070 | RT: 2.96 | ESI+: 449 |
| C071 | RT: 2.23 | ESI+: 379 |
| C072 | RT: 1.09 | ESI+: 430 |
| C073 | RT: 1.99 | ESI+: 472 |
| C074 | RT: 1.2 | ESI+: 396 |
| C075 | RT: 2.56 | ESI+: 449 |
| C076 | RT: 2.32 | ESI+: 457 |
| C077 | RT: 2.6 | ESI+: 395 |
| C078 | RT: 2.41 | ESI+: 381 |
| C079 | RT: 2.85 | ESI+: 435 |
| C080 | RT: 2.77 | ESI+: 443 |
| C081 | RT: 1.29 | ESI+: 444 |
| C082 | RT: 2.66 | ESI+: 463 |
| C083 | RT: 1.02 | ESI+: 424 |
| C084 | RT: 2.1 | ESI+: 367 |
| C085 | RT: 2.93 | ESI+: 491 |
| C086 | RT: 1.21 | ESI+: 426 |
| C087 | RT: 1.66 | ESI+: 378 |
| C088 | RT: 1.93 | ESI+: 411 |
| C089 | RT: 1.46 | ESI+: 383 |
| C090 | RT: 2.53 | ESI+: 441 |
| C091 | RT: 1.36 | ESI+: 410 |
| C092 | RT: 1.2 | ESI+: 396 |
| C093 | RT: 2.85 | ESI+: 435 |

TABLE 66

| Ex | DAT | |
|---|---|---|
| C094 | RT: 2.77 | ESI+: 443 |
| C095 | RT: 3.12 | ESI+: 487 |
| C096 | RT: 2.92 | ESI+: 459 |
| C097 | RT: 3.02 | ESI+: 473 |
| C098 | RT: 0.95 | ESI+: 439 |
| C099 | RT: 2.9 | ESI+: 521 |
| C100 | RT: 1.7 | ESI+: 424 |
| C101 | RT: 1.51 | ESI+: 413 |
| C102 | RT: 2.59 | ESI+: 443 |
| C103 | RT: 1.96 | ESI+: 450 |
| C104 | RT: 2.2 | ESI+: 437 |
| C105 | RT: 2.09 | ESI+: 435 |
| C106 | RT: 2.04 | ESI+: 397 |
| C107 | RT: 2.2 | ESI+: 437 |
| C108 | RT: 1.21 | ESI+: 396 |
| C109 | RT: 1.13 | ESI+: 430 |

TABLE 66-continued

| Ex | DAT | |
|---|---|---|
| C110 | RT: 2.22 | ESI+: 425 |
| C111 | RT: 2.36 | ESI+: 457 |
| C112 | RT: 2.36 | ESI+: 457 |
| C113 | RT: 2.3 | ESI+: 489 |
| C114 | RT: 1.32 | ESI+: 440 |
| C115 | RT: 2.81 | ESI+: 491 |
| C116 | RT: 2.84 | ESI+: 491 |
| C117 | RT: 1.79 | ESI+: 458 |
| C118 | RT: 3.02 | ESI+: 505 |
| C119 | RT: 1.38 | ESI+: 430 |
| C120 | RT: 1.76 | ESI+: 389 |
| C121 | RT: 2.38 | ESI+: 451 |
| C122 | RT: 2.11 | ESI+: 459 |
| C123 | RT: 3 | ESI+: 461 |
| C124 | RT: 2.84 | ESI+: 491 |
| C125 | RT: 2.48 | ESI+: 405 |
| C126 | RT: 1.77 | ESI+: 431 |
| C127 | RT: 2.02 | ESI+: 460 |
| C128 | RT: 2.29 | ESI+: 391 |
| C129 | RT: 1.42 | ESI+: 472 |
| C130 | RT: 2.89 | ESI+: 435 |
| C131 | RT: 3.21 | ESI+: 501 |
| C132 | RT: 1.82 | ESI+: 436 |
| C133 | RT: 2 | ESI+: 447 |
| C134 | RT: 2.84 | ESI+: 457 |
| C135 | RT: 1.78 | ESI+: 419 |
| C136 | RT: 1.83 | ESI+: 409 |
| C137 | RT: 2.36 | ESI+: 432 |
| C138 | RT: 2.17 | ESI+: 418 |
| C139 | RT: 1.87 | ESI+: 420 |
| C140 | RT: 3.26 | ESI+: 531 |
| C141 | RT: 2.33 | ESI+: 472 |
| C142 | RT: 1.7 | ESI+: 430 |
| C143 | RT: 1.36 | ESI+: 444 |
| C144 | RT: 1.24 | ESI+: 430 |
| C145 | RT: 1.95 | ESI+: 493 |
| C146 | RT: 1.82 | ESI+: 422 |
| C147 | RT: 1.08 | ESI+: 448 |
| C148 | RT: 1.01 | ESI+: 436 |
| C149 | RT: 1.07 | ESI+: 436 |
| C150 | RT: 2.09 | ESI+: 462 |
| C151 | RT: 2.25 | ESI+: 449 |
| C152 | RT: 3.14 | ESI+: 487 |
| C153 | RT: 2.85 | ESI+: 447 |
| C154 | RT: 1.4 | ESI+: 461 |
| C155 | RT: 0.85 | ESI+: 419 |
| C156 | RT: 2.44 | ESI+: 441 |
| C157 | RT: 1.8 | ESI+: 431 |
| C158 | RT: 2.5 | ESI+: 437 |
| C159 | RT: 1.69 | ESI+: 363 |
| C160 | RT: 1.58 | ESI+: 383 |
| C161 | RT: 1.19 | ESI+: 399 |
| C162 | RT: 1.1 | ESI+: 438 |
| C163 | RT: 1.74 | ESI+: 383 |
| C164 | RT: 1.88 | ESI+: 397 |
| C165 | RT: 2.67 | ESI+: 421 |
| C166 | RT: 2.82 | ESI+: 421 |
| C167 | RT: 0.9 | ESI+: 422 |
| C168 | RT: 2.68 | ESI+: 459 |
| C169 | RT: 1.49 | ESI+: 472 |
| C170 | RT: 2.96 | ESI+: 471 |
| C171 | RT: 1.32 | ESI+: 431 |
| C172 | RT: 2.05 | ESI+: 507 |
| C173 | RT: 2.3 | ESI+: 459 |
| C174 | RT: 2.79 | ESI+: 463 |
| C175 | RT: 2.78 | ESI+: 463 |
| C176 | RT: 1.42 | ESI+: 443 |
| C177 | RT: 2.63 | ESI+: 471 |
| C178 | RT: 2.67 | ESI+: 471 |
| C179 | RT: 1.85 | ESI+: 526 |
| C180 | RT: 2.62 | ESI+: 459 |
| C181 | RT: 1.19 | ESI+: 450 |
| C182 | RT: 1.94 | ESI+: 437 |
| C183 | RT: 2.94 | ESI+: 519 |
| C184 | RT: 2.56 | ESI+: 507 |
| C185 | RT: 2.78 | ESI+: 513 |
| C186 | RT: 2.78 | ESI+: 513 |

TABLE 67

| Ex | DAT | |
|---|---|---|
| C187 | RT: 2.06 | ESI+: 423 |
| C188 | RT: 2.36 | ESI+: 459 |
| C189 | RT: 2.7 | ESI+: 459 |
| C190 | RT: 1.64 | ESI+: 424 |
| C191 | RT: 2.56 | ESI+: 473 |
| C192 | RT: 2.77 | ESI+: 463 |
| C193 | RT: 2.45 | ESI+: 445 |
| C194 | RT: 2.25 | ESI+: 459 |
| C195 | RT: 1.01 | ESI+: 412 |
| C196 | RT: 2.47 | ESI+: 521 |
| C197 | RT: 2.47 | ESI+: 521 |
| C198 | RT: 2.87 | ESI+: 445 |
| C199 | RT: 1.79 | ESI+: 458 |
| C200 | RT: 1.8 | ESI+: 409 |
| C201 | RT: 2.62 | ESI+: 459 |
| C202 | RT: 1.26 | ESI+: 396 |
| C203 | RT: 1.96 | ESI+: 472 |
| C204 | RT: 1.97 | ESI+: 452 |
| C205 | RT: 0.99 | ESI+: 489 |
| C206 | RT: 1.7 | ESI+: 425 |
| C207 | RT: 1.14 | ESI+: 450 |
| C208 | RT: 1.82 | ESI+: 448 |
| C209 | RT: 1.84 | ESI+: 448 |
| C210 | RT: 1.65 | ESI+: 406 |
| C211 | RT: 2.21 | ESI+: 425 |
| C212 | RT: 1.7 | ESI+: 494 |
| C213 | RT: 1.62 | ESI+: 371 |
| C214 | RT: 2.72 | ESI+: 455 |
| C215 | RT: 2.68 | ESI+: 455 |
| C216 | RT: 2.68 | ESI+: 407 |
| C217 | RT: 0.92 | ESI+: 438 |
| C218 | RT: 2.19 | ESI+: 437 |
| C219 | RT: 2.07 | ESI+: 445 |
| C220 | RT: 2.14 | ESI+: 447 |
| C221 | RT: 1.68 | ESI+: 397 |
| C222 | RT: 2.19 | ESI+: 437 |
| C223 | RT: 1.63 | ESI+: 457 |
| C224 | RT: 2.26 | ESI+: 421 |
| C225 | RT: 2.68 | ESI+: 455 |
| C226 | RT: 1.63 | ESI+: 395 |
| C227 | RT: 2.94 | ESI+: 469 |
| C228 | RT: 1.4 | ESI+: 464 |
| C229 | RT: 1.5 | ESI+: 410 |
| C230 | RT: 1.56 | ESI+: 456 |
| C231 | RT: 2.18 | ESI+: 423 |
| C232 | RT: 1.46 | ESI+: 430 |
| C233 | RT: 1.28 | ESI+: 415 |
| C234 | RT: 2.32 | ESI+: 443 |
| C235 | RT: 2.13 | ESI+: 421 |
| C236 | RT: 2.37 | ESI+: 393 |
| C237 | RT: 1.21 | ESI+: 432 |
| C238 | RT: 1.93 | ESI+: 433 |
| C239 | RT: 1.93 | ESI+: 433 |
| C240 | RT: 1.8 | ESI+: 419 |
| C241 | RT: 1.78 | ESI+: 419 |
| C242 | RT: 1.56 | ESI+: 413 |
| C243 | RT: 1.74 | ESI+: 395 |
| C244 | RT: 1.79 | ESI+: 439 |
| C245 | RT: 2.58 | ESI+: 526 |
| C246 | RT: 1.97 | ESI+: 450 |
| C247 | RT: 2.54 | ESI+: 459 |
| C248 | RT: 1.5 | ESI+: 460 |
| C249 | RT: 1.24 | ESI+: 446 |
| C250 | RT: 1.94 | ESI+: 505 |
| C251 | RT: 2.71 | ESI+: 455 |
| C252 | RT: 1.41 | ESI+: 441 |
| C253 | RT: 1.15 | ESI+: 455 |
| C254 | RT: 2.42 | ESI+: 458 |
| C255 | RT: 2.82 | ESI+: 507 |
| C256 | RT: 2.19 | ESI+: 434 |
| C257 | RT: 2.1 | ESI+: 405 |
| C258 | RT: 2.51 | ESI+: 500 |
| C259 | RT: 3 | ESI+: 521 |
| C260 | RT: 1.4 | ESI+: 469 |
| C261 | RT: 1.82 | ESI+: 422 |
| C262 | RT: 1.68 | ESI+: 405 |
| C263 | RT: 1.97 | ESI+: 419 |
| C264 | RT: 0.84 | ESI+: 408 |

TABLE 67-continued

| Ex | DAT | |
|---|---|---|
| C265 | RT: 1.82 | ESI+: 419 |
| C266 | RT: 0.95 | ESI+: 422 |
| C267 | RT: 1.24 | ESI+: 411 |
| C268 | RT: 2.63 | ESI+: 455 |
| C269 | RT: 1.05 | ESI+: 462 |
| C270 | RT: 2.03 | ESI+: 436 |
| C271 | RT: 2.18 | ESI+: 455 |
| C272 | RT: 2.41 | ESI+: 437 |
| C273 | RT: 2.33 | ESI+: 437 |
| C274 | RT: 2.38 | ESI+: 437 |
| C275 | RT: 2.59 | ESI+: 468 |
| C276 | RT: 0.95 | ESI+: 419 |
| C277 | RT: 2.58 | ESI+: 483 |
| C278 | RT: 1.28 | ESI+: 478 |
| C279 | RT: 2.38 | ESI+: 469 |

TABLE 68

| Ex | DAT | |
|---|---|---|
| C280 | RT: 1.78 | ESI+: 397 |
| C281 | RT: 1.18 | ESI+: 455 |
| C282 | RT: 2.24 | ESI+: 455 |
| C283 | RT: 3.22 | ESI+: 487 |
| C284 | RT: 1.69 | ESI+: 470 |
| C285 | RT: 2.73 | ESI+: 461 |
| C286 | RT: 1.49 | ESI+: 465 |
| C287 | RT: 2.95 | ESI+: 435 |
| C288 | RT: 2.59 | ESI+: 483 |
| C289 | RT: 2.56 | ESI+: 477 |
| C290 | RT: 1.23 | ESI+: 450 |
| C291 | RT: 2.02 | ESI+: 447 |
| C292 | RT: 1.83 | ESI+: 485 |
| C293 | RT: 2.38 | ESI+: 489 |
| C294 | RT: 2.22 | ESI+: 456 |
| C295 | RT: 1.4 | ESI+: 455 |
| C296 | RT: 1.61 | ESI+: 497 |
| C297 | RT: 2.73 | ESI+: 496 |
| C298 | RT: 0.9 | ESI+: 405 |
| C299 | RT: 2.68 | ESI+: 468 |
| C300 | RT: 1.39 | ESI+: 410 |
| C301 | RT: 2.1 | ESI+: 464 |
| C302 | RT: 1.61 | ESI+: 397 |
| C303 | RT: 2.27 | ESI+: 473 |
| C304 | RT: 1.68 | ESI+: 451 |
| C305 | RT: 2.19 | ESI+: 439 |
| C306 | RT: 2.25 | ESI+: 463 |
| C307 | RT: 1.61 | ESI+: 427 |
| C308 | RT: 1.92 | ESI+: 411 |
| C309 | RT: 2.25 | ESI+: 439 |
| C310 | RT: 2.17 | ESI+: 473 |
| C311 | RT: 2.12 | ESI+: 437 |
| C312 | RT: 2.07 | ESI+: 425 |
| C313 | RT: 2.03 | ESI+: 465 |
| C314 | RT: 2.14 | ESI+: 449 |
| C315 | RT: 2.11 | ESI+: 449 |
| C316 | RT: 2 | ESI+: 437 |
| C317 | RT: 2.16 | ESI+: 465 |
| C318 | RT: 1.66 | ESI+: 411 |
| C319 | RT: 1.85 | ESI+: 425 |
| C320 | RT: 2.04 | ESI+: 439 |
| C321 | RT: 1.89 | ESI+: 451 |
| C322 | RT: 2.53 | ESI+: 479 |
| C323 | RT: 2.12 | ESI+: 485 |
| C324 | RT: 2.19 | ESI+: 489 |
| C325 | RT: 2.25 | ESI+: 526 |
| C326 | RT: 2.2 | ESI+: 451 |
| C327 | RT: 2.32 | ESI+: 526 |
| C328 | RT: 2.22 | ESI+: 453 |
| C329 | RT: 2.39 | ESI+: 467 |
| C330 | RT: 2.1 | ESI+: 459 |
| C331 | RT: 1.96 | ESI+: 425 |
| C332 | RT: 2.15 | ESI+: 459 |
| C333 | RT: 2.16 | ESI+: 473 |
| C334 | RT: 2.01 | ESI+: 437 |

INDUSTRIAL APPLICABILITY

Since the compound that is an active ingredient of the pharmaceutical of the present invention has a potent agonistic action on a cannabinoid type 2 receptor, and an excellent pharmacological action based thereon, the pharmaceutical composition of the present invention can be used as an agent for preventing or treating diseases related to a cannabinoid type 2 receptor, such as inflammatory diseases, pain, and the like.

The invention claimed is:

1. A compound of formula (I), or a salt thereof:

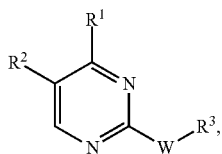

(I)

wherein
R$^1$ is lower alkyl, C$_{3-6}$ cycloalkyl, or halogeno-lower alkyl;
R$^2$ is —C(O)R$^{20}$;
W is —NH—;
R$^3$ is C$_{7-10}$ cycloalkyl which optionally has 1 to 5 substituents selected from the group consisting of lower alkyl, halogen, and —OH, on the ring;
each R$^0$ is the same as or different from each other, each representing H or lower alkyl;
R$^{20}$ is a nitrogen-containing saturated hetero ring group which optionally has 1 to 5 substituents selected from Group G$^2$;
Group G$^2$ is lower alkyl, halogen, halogeno-lower alkyl, —C(O)OR$^0$, —C(O)N(R$^0$)$_2$, —CN, —X—OR$^0$, —O-lower alkylene-OR$^0$, —O-halogeno-lower alkyl, —OC(O)-lower alkyl, —X—N(R$^0$)$_2$, oxo, —X—C$_{3-6}$ cycloalkyl, —X—O—X—C$_{3-6}$ cycloalkyl, —X-phenyl, or —X-morpholinyl;
each X is the same as or different from each other, each representing a bond or lower alkylene.

2. The compound or a salt thereof as described in claim 1, wherein R$^1$ is lower alkyl or C$_{3-6}$ cycloalkyl.

3. The compound or a salt thereof as described in claim 1, wherein R$^1$ is halogeno-lower alkyl.

4. The compound or a salt thereof as described in claim 1, wherein R$^{20}$ is 1-pyrrolidyl, 1-piperidyl, morpholin-4-yl, thiomorpholin-4-yl, or 1,1-dioxidothiomorpholin-4-yl, which optionally has 1 to 5 substituents selected from the group consisting of lower alkyl and halogen.

5. The compound or a salt thereof as described in claim 4, wherein R$^{20}$ is morpholin-4-yl or 1,1-dioxidothiomorpholin-4-yl.

6. The compound or a salt thereof as described in claim 5, wherein R$^3$ is C$_{7-10}$ cycloalkyl which optionally has 1 to 5 substituents selected from the group consisting of lower alkyl, halogen, and OH, on the ring and has a bridge.

7. The compound or a salt thereof as described in claim 1, wherein said compound is selected from the group consisting of:
N-adamantan-1-yl-5-[(4,4-difluoropiperidin-1-yl)carbonyl]-4-(trifluoromethyl)pyrimidin-2-amine,
rac-N-[(1R,2R,4S)-bicyclo[2.2.1]hept-2-yl]-4-isopropyl-5-(morpholin-4-ylcarbonyl)pyrimidin-2-amine,
rac-N-[(1R,2R,4S)-bicyclo[2.2.1]hept-2-yl]-4-cyclopropyl-5-[(1,1-dioxidothiomorpholin-4-yl)carbonyl]pyrimidin-2-amine,
rac-N-[(1R,2R,4S)-bicyclo[2.2.1]hept-2-yl]-4-tert-butyl-5-(morpholin-4-ylcarbonyl)pyrimidin-2-amine,
N-[(1S,2S,4R)-bicyclo[2.2.1]hept-2-yl]-4-isopropyl-5-(morpholin-4-ylcarbonyl)pyrimidin-2-amine,
N-[(1R,2R,4S)-bicyclo[2.2.1]hept-2-yl]-4-isopropyl-5-(morpholin-4-ylcarbonyl)pyrimidin-2-amine,
3-({5-[(3,3,4,4-tetrafluoropyrrolidin-1-yl)carbonyl]-4-(trifluoromethyl)pyrimidin-2-yl}amino)adamantan-1-ol,
rac-N-[(1R,2R,4S)-bicyclo[2.2.1]hept-2-yl]-5-[(1,1-dioxidothiomorpholin-4-yl)carbonyl]-4-(trifluoromethyl)pyrimidin-2-amine,
5-[(1,1-dioxidothiomorpholin-4-yl)carbonyl]-4-(trifluoromethyl)-N-[(1R,2S,4R)-1,7,7-trimethylbicyclo[2.2.1]hept-2-yl]pyrimidin-2-amine,
5-[(1,1-dioxidothiomorpholin-4-yl)carbonyl]-N-(3,5,7-trifluoroadamantan-1-yl)-4-(trifluoromethyl)pyrimidin-2-amine,
N-[(1R,2R,4S)-bicyclo[2.2.1]hept-2-yl]-5-[(1,1-dioxidothiomorpholin-4-yl)carbonyl]-4-(trifluoromethyl)pyrimidin-2-amine,
N-[(1S,2S,4R)-bicyclo[2.2.1]hept-2-yl]-5-[(1,1-dioxidothiomorpholin-4-yl)carbonyl]-4-(trifluoromethyl)pyrimidin-2-amine, and
N-bicyclo[2.2.2]oct-1-yl-5-[(1,1-dioxidothiomorpholin-4-yl)carbonyl]-4-(trifluoromethyl)pyrimidin-2-amine.

8. A pharmaceutical composition, comprising a compound or a salt thereof as described in claim 1 and a pharmaceutically acceptable excipient.

9. A pharmaceutical composition, comprising a compound or a salt thereof as described in claim 4 and a pharmaceutically acceptable excipient.

10. A pharmaceutical composition, comprising a compound or a salt thereof as described in claim 2 and a pharmaceutically acceptable excipient.

11. A pharmaceutical composition, comprising a compound or a salt thereof as described in claim 3 and a pharmaceutically acceptable excipient.

12. The compound according to claim 1 or a salt thereof, wherein said compound is rac-N-[(1R,2R,4S)-bicyclo[2.2.1]hept-2-yl]-4-isopropyl-5-(morpholin-4-ylcarbonyl)pyrimidin-2-amine.

13. The compound according to claim 1 or a salt thereof, wherein said compound is rac-N-[(1R,2R,4S)-bicyclo[2.2.1]hept-2-yl]-4-tert-butyl-5-(morpholin-4-ylcarbonyl)pyrimidin-2-amine.

14. The compound according to claim 1 or a salt thereof, wherein said compound is rac-N-[(1R,2R,4S)-bicyclo[2.2.1]hept-2-yl]-5-[(1,1-dioxidothiomorpholin-4-yl)carbonyl]-4-(trifluoromethyl)pyrimidin-2-amine.

15. The compound according to claim 1 or a salt thereof, wherein said compound is 5-[(1,1-dioxidothiomorpholin-4-yl)carbonyl]-N-(3,5,7-trifluoroadamantan-1-yl)-4-(trifluoromethyl)pyrimidin-2-amine.

16. The compound according to claim 1 or a salt thereof, wherein said compound is N-bicyclo[2.2.2]oct-1-yl-5-[(1,1-dioxidothiomorpholin-4-yl)carbonyl]-4-(trifluoromethyl)pyrimidin-2-amine.

* * * * *